United States Patent [19]

[11] 4,117,127

Okamoto et al.

[45] Sep. 26, 1978

[54] $N^2$-ARYLSULFONYL-L-ARGININAMIDES AND THE PHARMACEUTICALLY ACCEPTABLE SALTS THEREOF

[75] Inventors: Shosuke Okamoto; Akiko Hijikata, both of Kobe; Ryoji Kikumoto, Machida; Yoshikuni Tamao, Yokohama; Kazuo Ohkubo, Machida; Tohru Tezuka, Yokohama; Shinji Tonomura, Tokyo, all of Japan

[73] Assignees: Mitsubishi Chemical Industries Ltd.; Shosuke Okamoto, both of Tokyo, Japan

[21] Appl. No.: 844,188

[22] Filed: Oct. 21, 1977

Related U.S. Application Data

[60] Division of Ser. No. 760,745, Jan. 19, 1977, Pat. No. 4,066,773, which is a continuation-in-part of Ser. No. 653,217, Jan. 28, 1976, Pat. No. 4,055,651, Ser. No. 713,486, Aug. 11, 1976, Pat. No. 4,073,914, Ser. No. 671,436, Mar. 29, 1976, Pat. No. 4,066,758, and Ser. No. 703,704, Jul. 8, 1976, Pat. No. 4,069,323, said Ser. No. 671,436, is a division of Ser. No. 622,390, Oct. 14, 1975, abandoned.

[30] Foreign Application Priority Data

| | | | |
|---|---|---|---|
| Nov. 8, 1974 | [JP] | Japan | 49-128774 |
| Nov. 8, 1974 | [JP] | Japan | 49-128775 |
| Nov. 29, 1974 | [JP] | Japan | 49-136695 |
| Nov. 29, 1974 | [JP] | Japan | 49-136697 |
| Feb. 25, 1975 | [JP] | Japan | 50-023268 |
| Feb. 26, 1975 | [JP] | Japan | 50-023635 |
| Mar. 5, 1975 | [JP] | Japan | 50-026768 |
| Mar. 11, 1975 | [JP] | Japan | 50-029357 |
| Mar. 11, 1975 | [JP] | Japan | 50-029358 |

[51] Int. Cl.² .................... A61K 31/51; C07D 417/12

[52] U.S. Cl. ............................ 424/247; 260/112.5 R; 260/279 R; 260/287 CE; 260/287 D; 260/287 T; 424/177; 424/248.5; 424/250; 424/251; 424/257; 424/258; 544/35; 544/37; 544/38; 544/40; 544/103; 544/104; 544/237; 544/284; 544/347; 544/353

[58] Field of Search .................... 260/112.5 R, 250 P, 260/250 Q, 250 C, 256.5 R, 267, 279 R, 287 D, 287 T, 287 CE; 544/35, 37, 38, 40, 103, 104; 424/177, 247, 248.5, 250, 251, 257, 258

[56] References Cited

U.S. PATENT DOCUMENTS

| | | | |
|---|---|---|---|
| 3,622,615 | 11/1971 | Nicolaides et al. | 560/10 |
| 3,978,045 | 8/1976 | Okamoto et al. | 260/239 B |

*Primary Examiner*—Richard L. Raymond
*Attorney, Agent, or Firm*—Oblon, Fisher, Spivak, McClelland & Maier

[57] ABSTRACT

$N^2$-arylsulfonyl-L-argininamides and the pharmaceutically acceptable salts thereof have been found to be effective as pharmaceutical agents for the inhibition and suppression of thrombosis in mammals.

4 Claims, No Drawings

$N^2$-ARYLSULFONYL-L-ARGININAMIDES AND THE PHARMACEUTICALLY ACCEPTABLE SALTS THEREOF

CROSS-REFERENCE TO RELATED APPLICATIONS

This is a division, of application Ser. No. 760,745, filed Jan. 19, 1977, now U.S. Pat. 4,066,773 which in turn is a continuation-in-part of the following applications:

Ser. No. 653,217 of Jan. 28, 1976, now U.S. Pat. 4,055,651

Ser. No. 713,486 of Aug. 11, 1976, now U.S. Pat. 4,073,914

Ser. No. 671,436 of Mar. 29, 1976, now U.S. Pat. 4,066,758

Ser. No. 703,704 of July 3, 1976, now U.S. Pat. 4,069,323

The Ser. No. 671,436 is a divisional of Ser. No. 622,390 filed Oct. 14, 1975, now abandoned.

BACKGROUND OF THE INVENTION

1. Field of the Invention

This invention relates to the discovery of certain new and useful $N^2$-arylsulfonyl-L-argininamides and the pharmaceutically acceptable salts thereof, which are of especial value in view of their outstanding antithrombotic properties and low toxicities.

2. Description of the Prior Art

In the past, there have been many attempts to obtain new and improved agents for the treatment of thrombosis. The $N^2$-(p-tolysulfonyl)-L-arginine esters have been found to be one type of agent which can be used and these have been found to be effective in dissolving blood clots. (U.S. Pat. No. 3,622,615, issued Nov. 23, 1971). One family of compounds which have been found to be particularly useful as highly specific inhibitors of thrombin for the control of thrombosis is the $N^2$-dansyl-L-argine ester or amide. (Our pending U.S. Application Ser. No. 496,939, filed Aug. 13, 1974 now U.S. Pat. No. 3,978,045). However, there is a continuing need for a highly specific inhibitor of thrombin for the control of thrombosis, which exhibits lower toxicity.

SUMMARY OF THE INVENTION

It has now been discovered that $N^2$-arylsulfonyl-L-argininamides exhibit antithrombotic activity and even lower toxicity levels at the same relative potencies, as compared with the $N^2$-dansyl-L-arginine ester or amide.

An $N^2$-arylsulfonyl-L-argininamide having the formula (I):

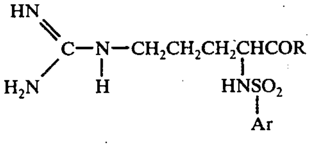

(I)

or a pharmaceutically acceptable salt thereof, wherein R is

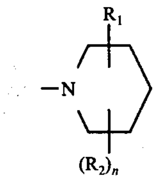

wherein $R_1$ is —$COOR_3$ wherein $R_3$ is hydrogen, $C_1$–$C_{10}$ alkyl, $C_6$–$C_{10}$ aryl, $C_7$–$C_{12}$ aralkyl or 5-indanyl; each $R_2$ independently is hydrogen, $C_1$–$C_{10}$ alkyl, phenyl, $C_1$–$C_5$ alkoxy, $C_2$–$C_6$ alkoxycarbonyl, or carboxy; n is an integer of 1 to 4, $R_1$ is substituted into the piperidine ring at the 2 or 3 position; and $R_2$ is substituted into the piperidine ring at the 2, 3, 4, 5 or 6 position;

and Ar is naphthyl substituted with at least one substitutent selected from the group consisting of halo, nitro, cyano, hydroxy, $C_1$–$C_{10}$ alkyl and $C_2$–$C_{20}$ dialkylamino, and at least one substituent selected from the group consistng of $C_1$–$C_{10}$ alkoxy, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{10}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl and phenyl optionally substituted with at least one hydroxy, $C_1$–$C_5$ alkoxy, or mixtures thereof;

naphthyl substituted with at least one $C_1$–$C_5$ alkoxy and at least one substituent selected from the group consisting of sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl and phenyl optionally substituted with at least one hydroxy, $C_1$–$C_5$ alkoxy or mixtures thereof;

naphthyl substituted with at least one substituent selected from the group consisting of sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxylakyl, $C_1$–$C_{10}$ haloalkyl and phenyl optionally substituted with at least one hydroxy, $C_1$–$C_5$ alkoxy or mixtures thereof;

5,6,7,8-tetrahydronaphthyl substituted with at least one substituent selected from the group consisting of halo, nitro, cyano, hydroxy, $C_1$–$C_{10}$ alkyl, $C_1$–$C_{10}$ alkoxy, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxylalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl and phenyl optionally substituted with at least one hydroxy, $C_1$–$C_5$ alkoxy or mixtures thereof;

$C_7$–$C_{12}$ aralkyl-9,10-dihydroanthryl, 5,6,7,8-tetrahydroanthryl, 9,10-dihydrophenanthryl, 1,2,3,4,5,6,7,8-octahydrophenanthryl, indenyl, indanyl, fluorenyl, acenaphthenyl, phenylthiophenyl, 1,2-ethylenedioxyphenyl, chromanyl, isochromanyl, 2,3-dihydrobenzofuranyl, 1,3-dihydroisobenzofuranyl, 2,3-ethylenedioxynaphthyl, xanthenyl, thioxanthenyl, 1,2-trimethylenedioxyphenyl, 2H-chromenyl, 3,4-dehydro-1-isochromanyl, 4H-chromenyl, indolinyl, isoindolinyl, 1,2,3,4-tetrahydroquinolyl or 1,2,3,4-tetrahydrosoquipolyl group, any of which is unsubstituted or substituted with one or more groups selected from the group consisting of halo, nitro, cyano, hydroxy, $C_1$–$C_{10}$ alkyl, $C_1$–$C_{10}$ alkoxy. $C_2$—$C_{20}$ dialkylamino, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl, oxo and phenyl optionally substituted with at least one hydroxy, $C_1$–$C_5$ alkoxy or mixtures thereof;

naphthoquinony, anthryl, phenanthryl, pentalenyl, heptalenyl, azulenyl, biphenylenyl, αs-indacenyl, s-indacenyl, acenaphthylenyl, phenylcarbonylphenyl, phenoxyphenyl, benzofuranyl, isobenzofuranyl, benzo [b] thienyl, isobenzothienyl, oxanthrenyl, thianthrenyl, dibenzofuranyl, dibenzothienyl, phenoxathiinyl, indolyl, IH-indazolyl, quinolyl, isoquinolyl, phthalazinyl, 1,8-naphthyridinyl, quinoxalinyl, quinazolinyl, cinnolinyl, carbazolyl, acridinyl, phenazinyl, phenothiazinyl, phenoxazinyl or benzimidazolyl group, any of which is unsubstituted or substituted with one or more groups selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl and phenyl optionally substituted with at least one hydroxy, $C_1$–$C_5$ alkoxy or mixtures thereof.

An $N^2$-arylsulfonyl-L-argininamide having the formula (I):

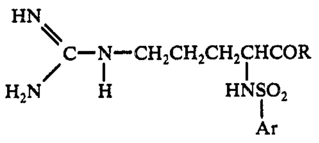

(1)

or a pharmaceutically acceptable salt thereof, wherein R is

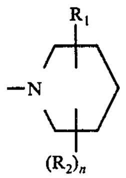

wherein $R_1$ is -$COOR_3$ wherein $R_3$ is hydrogen, $C_1$–$C_{10}$ alkyl, $C_6$–$C_{10}$ aryl, $C_7$–$C_{12}$ aralkyl or 5-indanyl; each $R_2$ independently is hydrogen, $C_1$–$C_{10}$ alkyl, phenyl, $C_1$–$C_5$ alkoxy, $C_2$–$C_6$ alkoxycarbonyl, or carboxy; n is an integer of 1 to 4, $R_1$ is substituted into the piperidine ring at the 2 or 3 position; and $R_2$ is substituted into the piperidine ring at the 2, 3, 4, 5 or 6 position;

and Ar is naphthyl substituted with at last one substituent selected from the group consisting of halo, nitro, cyano, hydroxy, $C_1$–$C_{10}$ alkyl and $C_2$–$C_{20}$ dialkylamino, and at least one substituent selected from the group consisting of $C_1C_{10}$ alkoxy, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{10}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl and phenyl optionally substituted with at least one hydroxy, $C_1$–$C_5$ alkoxy, or mixtures thereof;

naphthyl substituted with at least one $C_1$–$C_5$ alkoxy and at least one substituent selected from the group consisting of sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl and phenyl optionally substituted with at least one hydroxy, $C_1$–$C_5$ alkoxy or mixtures thereof;

naphthyl substituted with at least one substituent selected from the group consisting of sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl and phenyl optionally substituted with at least one hydroxy, $C_1$–$C_5$ alkoxy or mixtures thereof;

5,6,7,8-tetrahydronaphthyl substituted with at least one substituent selected from the group consisting of halo, nitro, cyano, hydroxy, $C_1$–$C_{10}$ alkyl, $C_1$–$C_{10}$ alkoxy, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl and phenyl optionally substituted with at least one hydroxy, $C_1$–$C_5$ alkoxy or mixtures thereof;

$C_7$–$C_{12}$ aralkyl-9,10-dihydroanthryl, 5,6,7,8-tetrahydroanthryl, 9,10-dihydrophenanthryl, 1,2,3,4,5,6,7,8-octahydrophenanthryl, indenyl, indanyl, fluorenyl, acenaphthenyl, phenylthiophenyl, 1,2-ethylenedioxy-phenyl, chromanyl, isochromanyl, 2,3-dihydrobenzofuranyl, 1,3-dihydroisobenzofuranyl, 2,3-ethylenedioxynaphthyl, xanthenyl, thioxanthenyl, 1,2-trimethylenedioxyphenyl, 2H-dhromenyl, 3,4-dehydro-1-isochromanyl, 4H-dhromenyl, indolinyl, isoindolinyl, 1,2,3,4-tetrahydroquinolyl or 1,2,3,4-tetrahydroisoquinolyl group, any of which is unsubstituted or substituted with one or more groups selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino, carbamoyl, $C_3$–$C_{10}$ N,N-dialkylcarbamoyl, amino, $C_1$–$C_{10}$ alkylamino, marcapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl, oxo and phenyl optionally substituted with at least one hydroxy, $C_1$–$C_5$ alkoxy or mixtures thereof;

a phenyl which is unsubstituted or substituted with one or more groups selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxylakyl, $C_1$–$C_{10}$ haloalkyl and phenyl optionally substituted with at least one hydroxy, $C_1$–$C_5$alkoxy or mixtures thereof.

Also encompassed within this invention are pharmaceutically acceptable salts thereof.

This invention also relates to a method for inhibiting activity and suppressing activation of thrombin in vivo in mammals which comprises administering to a mammal a pharmaceutically (antithrombotically) effective amount of an $N^2$-arylnaphthalenesulfonyl-L-argininamide or the pharmaceutically acceptable salts thereof.

DETAILED DESCRIPTION OF THE PREFERRED EMBODIMENTS

This invention relates to a group of $N^2$-arylsulfonyl-L-argininamides of the formula (I):

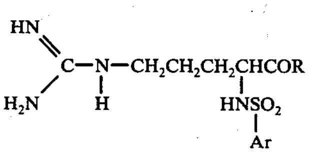

(1)

wherein R is selected from the group consisting of

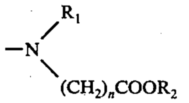

(1)

wherein $R_1$ is selected from the group consisting of $C_2$–$C_{10}$ alkyl, such as ethyl, propyl, butyl, isobutyl, pentyl, hexyl, octyl, decyl or the like, alkenyl of 3–10 (preferably 3–6) carbon atoms, such as allyl, 2-butenyl, 3-butenyl, 2-pentenyl or the like, alkynyl of 3–10 (preferably 3–6) carbon atoms, such as 2-propynyl, 2-butynyl, 3-butynyl or the like, alkoxyalkyl of 2–10 (preferably 2–6) carbon atoms, such as methoxymethyl, ethoxymethyl, propoxymethyl, 2-methoxyethyl, 2-ethoxyethyl, 2-propoxyethyl, 2-methoxypropyl, 3-methoxypropyl, 3-ethoxypropyl, 3-propoxypropyl, 4-methoxybutyl, 4-ethoxybutyl, 4-butoxybutyl, 5-butoxypentyl or the like, alkylthioalkyl of 2–10 (preferably 2–6) carbon atoms, such as methylthiomethyl, ethylthiomethyl, propylthiomethyl, 2-methylthioethyl, 2-ethylthioethyl, 2-propylthioethyl, 3-methylthiopropyl, 2-methylthiopropyl, 3-ethylthiopropyl, 3-propylthiopropyl, 4-methylthiobutyl, 4-ethylthiobutyl, 4-butylthiobutyl, 5-butylthiopentyl or the like, alkylsulfinylalkyl of 2–10 (preferably 2–6) carbon atoms, such as methylsulfinylmethyl, ethylsulfinylmethyl, propylsulfinylmethyl, 2-methylsulfinylethyl, 2-ethylsulfinylethyl, 2-propylsulfinylethyl, 3-methylsulfinylpropyl, 3-ethylsulfinylpropyl or the like, hydroxyalkyl of 1–10 (preferably 1–6) carbon atoms, such as hydroxymethyl, 2-hydroxyethyl, 3-hydroxypropyl, 2-hydroxypropyl, 4-hydroxybutyl, 3-hydroxybutyl, 5-hydroxypentyl or the like, carboxyalkyl of 2–10 (preferably 2–7) carbon atoms, such as carboxymethyl, 2-caboxyethyl, 2-carboxypropyl, 3-carboxypropyl, 1-carboxybutyl, 2-carboxybutyl, 4-carboxybutyl or the like, alkoxycarbonylalkyl of 3–10 (preferably 3–8) carbon atoms, such as methoxycarbonylmethyl, 2-ethoxycarbonylethyl, 2-ethoxycarbonylpropyl, 3-methoxycarbonylpropyl, 1-methoxycarbonylbutyl, 2-ethoxycarbonylbutyl, 4-methoxycarbonylbutyl or the like, alkylcarbonylalkyl of 3 to 10 carbon atoms such as methylcarbonylethyl or the like, haloalkyl of 1–10 (preferably 1–5) carbon atoms such as chloromethyl, 2-chloroethyl, 2-bromoethyl, 2-chloropropyl, 3-chloropropyl, 2-chlorobutyl, 4-chlorobutyl or the like, aralkyl of 7–15 (preferably 7–10) carbon atoms, such as benzyl, phenethyl, 3-phenylpropyl, 4-phenylbutyl, 6-phenylhexyl, 1-phenylethyl, 2-phenylpropyl or the like, -carboxyaralkyl of 8–15 (preferably 8–12) carbon atoms, such as -carboxybenzyl, -carboxyphenethyl or the like $C_3$–$C_{10}$ cycloalkyl, such as cyclopropyl, cyclobutyl, cyclopentyl, cyclohexyl, cycloheptyl, cyclooctyl, cyclononyl or cyclodecyl, $C_4$–$C_{10}$ cycloalkylalkyl, such as cyclopropylmethyl, cyclopentylmethyl, cyclohexylmethyl, 2-cyclohexylethyl, cyclooctylmethyl or the like, furfuryl, tetrahydrofurfuryl, optionally substituted with one or more $C_1$–$C_5$ alkyl, such as methyl, ethyl, propyl, butyl, or the like, and/or $C_1$–$C_5$ alkoxy groups, such as methoxy, ethoxy, propoxy, butoxy or the like, 3-furylmethyl, tetrahydro-3-furylmethyl, optionally substituted with one or more $C_1$–$C_5$ alkyl such as methyl, ethyl, propyl, butyl or the like, and/or $C_1$–$C_5$ alkoxy groups, such as methoxy, ethoxy, propoxy, butoxy or the like, tetrahydro-2(3 or 4)-pyranylmethyl optionally substituted with one or more $C_1$–$C_5$ alkyl such as methyl, ethyl, propyl, butyl or the like, and/or $C_1$–$C_5$ alkoxy groups, such as methoxy, ethoxy, propoxy, butoxy or the like, 1,4-dioxa-2-cyclohexylmethyl optionally substituted with one or more $C_1$–$C_5$ alkyl such as methyl, ethyl, propyl, butyl or the like, and/or $C_{1-C5}$ alkoxy groups, such as methoxy, ethoxy, propoxy, butoxy or the like, 2-thenyl, 3-thenyl, tetrahydro-2-thenyl, optionally substituted with one or more $C_1$–$C_5$ alkyl such as methyl, ethyl, propyl, butyl or the like, and/or $C_1$–$C_5$ alkoxy groups such as methoxy, ethoxy, propoxy butoxy or the like and tetrahydro-3-thenyl; $R_2$ is selected from the group consisting of hydrogen, $C_1$–$C_{10}$ alkyl, such as methyl, ethyl, propyl, butyl, tert-butyl, hexyl, octyl, decyl or the like, $C_6$–$C_{10}$ aryl, such as phenyl, m-tolyl, naphthyl or the like, aralkyl of 7–12 (preferably 7–10) carbon atoms, such as benzyl, phenethyl or the like, or 5-indanyl; and n is an integer of 1, 2 or 3,

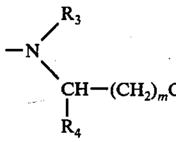

(2)

wherein $R_3$ is selcted from the group consisting of hydrogen, $C_1$–$C_{10}$ alkyl, such as methyl, ethyl, propyl, butyl, isobutyl, pentyl, hexyl, octyl, decyl or the like, alkenyl of 3–10 (preferably 3–6) carbon atoms, such as allyl, 2-butenyl, 3-butenyl, 2-pentenyl or the like, alkynyl of 3–10 (preferably 3–6) carbon atoms, such as 2-propynyl, 2-butynyl, 3-butynyl or the like, alkoxyalkyl of 2–10 (preferably 2–6) carbon atoms, such as methoxymethyl, ethoxynethyl, propoxymethyl, 2-methoxyethyl, 2-ethoxyethyl, 2-propoxyethyl, 2-methoxypropyl, 3-methoxypropyl, 3-ethoxypropyl, 3-propoxypropyl, 4-methoxybutyl, 4-ethoxybutyl, 4-butoxybutyl, 5-butoxypentyl or the like, alkylthioalkyl of 2–10 (preferably 2–6) carbon atoms, such as methylthiomethyl, ethylthiomethyl, propylthiomethyl, 2-methylthioethyl, 2-ethylthioethyl, 2-propylthioethyl, 3-methylthiopropyl, 2-methylthiopropyl, 3-ethylthiopropyl, 3-propylthiopropyl, 4-methylthiobutyl, 4-ethylthiobutyl, 4-butylthiobutyl, 5-butylthiopentyl or the like, alkylsulfinylalkyl of 2–10 (preferably 2–6) carbon atoms, such as methylsulfinylmethyl, ethylsulfinylmethyl, propylsulfinylmethyl, 2-methylsulfinylethyl, 2-ethylsulfinylethyl, 2-propylsulfinylethyl, 3-methylsulfinylpropyl, 3-ethylsulfinylpropyl or the like, hydroxyalkyl of 1–10 (preferably 1–6) carbon atoms, such as hydroxymethyl, 2-hydroxyethyl, 3-hydroxypropyl, 2-hydroxypropyl, 4- hydroxybutyl, 3-hydroxybutyl, 5-hydroxypentyl or the like, carboxyalkyl of 2-10 (preferably 2-7) carboxymethyl, 2-carboxyethyl, 2-carboxypropyl, 3-carboxypropyl, 1-carboxybutyl, 2-carboxybutyl, 4carboxybutyl or the like, alkoxycarbonylalkyl of 3-10 (preferably 3-8) carbon atoms, such as methoxycarbonylmethyl, 2-methoxycarbonylethyl, 2-ethoxycarbonylpropyl, 3-methoxycarbonylpropyl, 1-methoxycarbonylbutyl, 2-ethoxycarbonylbutyl, 4-methoxycarbonylbutyl or the like, alkylcarbonylalkyl of 3 to 10 carbon atoms such as methylcarbonylethyl or the like, haloalkyl or 1-10 (preferably 1-5) carbon atoms such as chloromethyl, 2-chloroethyl, 2-bromoethyl, 2-chloropropyl, 3-chloropropyl, 2-chlorobutyl, 4-chlorobutyl or the like, aralkyl of 7-15 (preferably 7-10) carbon atoms, such as benzyl, phenethyl, 3-phenylpropyl, 4-phenylbutyl, 6-phenylhexyl, 1-phenylethyl, 2-phenylpropyl or the like, α-carboxyaralkyl of 8-15 (preferably 8-12) carbon atoms, such as α-carboxybenzyl, α-carboxyphenethyl or the like, $C_3$-$C_{10}$ cycloalkyl, such as cyclopropyl, cyclobutyl, cyclopentyl, cyclohexyl, cycloheptyl, cyclooctyl, cyclononyl or cyclodecyl, $C_4$-$C_{10}$ cycloalkylalkyl, such as cyclopropylmethyl, cyclopentylmethyl, cyclohexylmethyl, 2-cyclohexylethyl, cyclooctylmethyl or the like, furfuryl, tetrahydrofurfuryl optionally substituted with one or more $C_1$-$C_5$ alkyl such as methyl, ethyl, propyl, butyl or the like, and/or $C_1$-$C_5$ alkoxy groups, such as methoxy, ethoxy, propoxy, butoxy or the like 3-furylmethyl, tetrahydro-3-furylmethyl optionally substituted with one or more $C_1$-$C_5$ alkyl such as methyl, ethyl, propyl, butyl or the like, and/or $C_1$-$C_5$ alkoxy groups, such as methoxy, ethoxy, propoxy, butoxy or the like tetrahydro-2 (3 or 5)-pyranylmethyl optionally substituted with one or more $C_1$-$C_5$ alkyl such as methyl, ethyl, propyl, butyl or the like, and/or $C_1$-$C_5$ alkoxy groups, such as methoxy, ethoxy, propoxy, butoxy or the like, 1,4 -dioxa-2-cyclohexylmethyl optionally substituted with one or more $C_1$-$C_5$ alkyl such as methyl, ethyl, propyl, butyl or the like and/or $C_1$-$C_5$ alkoxy groups, such as methoxy, ethoxy, propoxy, butoxy or the like, 2-thenyl, 3-thenyl, tetrahydro-2-thenyl optionally substituted with one or more $C_1$-$C_5$ alkyl such as methyl, ethyl, propyl, butyl or the like, and/or $C_1$-$C_5$ alkoxy groups, such as methoxy, ethoxy, propoxy, butoxy or the like, and tetrahydro-3-thenyl; $R_4$ is selected from the group consisting of alkyl of 1-10 (preferably 1-5) carbon atoms, such as methyl, ethyl, propyl, isopropyl, butyl, isobutyl, sec-butyl, pentyl or the like, carboxy, alkoxycarbonyl of 2-10 (preferably 2-5) carbon atoms, such as methoxycarbonyl, ethoxycarbonyl, propoxycarbonyl or the like, phenyl optionally substituted with one or more $C_1$-$C_5$ alkyl, such as methyl, ethyl, propyl, butyl or the like, and/or $C_1$-$C_5$ alkoxy groups, such as methoxy, ethoxy, propoxy, butoxy or the like, aralkyl of 7-12 (preferably 7-10) carbon atoms, such as benzyl, phenethyl or the like, and ring substituted benzyl wherein said substituent is alkyl of 1-5 (preferably 1-3) carbon atoms, such as methyl, ethyl, propyl or isopropyl, or alkoxy of 1-5 (preferably 1-3) carbon atoms, such as methoxy, ethoxy, propoxy or isopropoxy; $R_5$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, and 5-indanyl; and m is an integer of 0, 1 or 2,

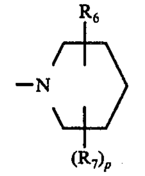

(3)

wherein $R_6$ is —$COOR_8$ wherein $R_8$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, and 5-indanyl; each $R_7$ independently is hydrogen, alkyl of 1-10 (preferably 1-6) carbon atoms, such as methyl, ethyl, propyl, isopropyl, butyl, hexyl, octyl, decyl or the like, phenyl, $C_1$-$C_5$ alkoxy, such as methoxy, ethoxy, propoxy, butoxy or the like, $C_2$-$C_6$ alkoxycarbonyl, such as methoxycarbonyl, ethoxycarbonyl or the like, or carboxy; p is an integer of 1 to 4; $R_6$ is substituted at the 2 or 3-position; and $R_7$ can be substituted at the 2, 3, 4, 5 or 6-position.

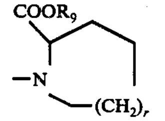

(4)

optionally substituted with one or more $C_1$-$C_5$ alkyl, such as methyl, ethyl, propyl, butyl or the like, or $C_1$-$C_5$ alkoxy groups, such as methoxy, ethoxy, propoxy, butoxy or the like wherein $R_9$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, and 5-indanyl; and r is an integer of 1, 2, 3 or 4,

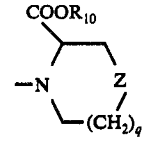

(5)

wherein $R_{10}$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, and 5-indanyl; Z is selected from the group consisting of oxy (—O—), thio (—S—) and sulfinyl (—SO—); q is an integer of 0 or 1, and

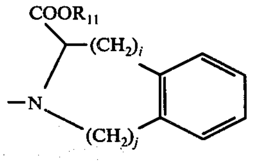

(6)

wherein $R_{11}$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, and 5-indanyl; i is an integer of 0, 1 or 2; j is an integer of 0, 1 or 2; and the sum of i + j is an integer of 1 or 2; and Ar is a phenyl, naphthyl, naphthoquinonyl, anthryl, phenanthryl, pentalenyl, heptalenyl, azulenyl, biphenylenyl, as -indacenyl, S-indacenyl, acenaphthylenyl, phenylcarbonylphenyl, phenoxyphenyl, benzofuranyl, isobenzofuranyl, benzo [b] thienyl, isobenzothienyl, oxanthrenyl, thianthrenyl, dibenzofuranyl, dibenzothienyl, phenoxathiinyl, indolyl, 1H-indazolyl, quinolyl, isoquinolyl, phthalazinyl, 1,8-naphthyridinyl, quinoxalinyl, quinazolinyl, cinnolinyl, carbazolyl, acridinyl, phenazinyl, phenothiazinyl, phenoxazinyl or benzimidazolyl group each of which is unsubstituted or substituted with one or more groups selected from the group consisting of halo, nitro, cyano, hydroxy, alkyl of 1-10 (preferably 1-5) carbon atoms, such as methyl, ethyl, propyl, butyl or the like, alkoxy of 1-10 (preferably 1-5) carbon atoms, such as methoxy, ethoxy, propoxy, butoxy or the like, dialkylamino of 2-20 (preferably 2-10) carbon atoms, such as dimethylamino, diethylamino, dipropylamino or the like, sulfoamino, carbamoyl, N,N-dialkylcarbamoyl of 3-10 (preferably 3-7) carbon atoms, such as N,N-dimethylcarbamoyl, N,N-diethylcarbamoyl or the like, amino, alkylamino of 1-10 (preferably 1-5) carbon atoms, such as methylamino, ethylamino, propylamino, butylamino or the like, mercapto, alkylthio of 1-10 (preferably 1-5) carbon atoms, such as methylthio, ethylthio, propylthio, butylthio or the like, aralkyl of 7-12 (preferably 7-10) carbon atoms, such as benzyl, phenethyl or the like, carboxyl, alkoxycarbonyl of 2-10 (preferably 2-6) carbon atoms, such as methoxycarbonyl, ethoxycarbonyl or the like, carboxyalkyl of 2-10 (preferably 2-6) carbon atoms, such as carboxymethyl, 2-carboxyethyl, 2-carboxypropyl or the like, acylamino such as alkylcarbonylamino of 1-10 (preferably 1-5) carbon atoms, such as acetylamino, propionylamino or the like, alkylcarbonyl of 2-10 (preferably 2-6) carbon atoms, such as acetyl, propionyl or the like, hydroxyalkyl of 1-10 (preferably 1-5) carbon atoms, such as hydroxymethyl, 2-hydroxyethyl, 2-hydroxypropyl or the like, haloalkyl of 1-10 (preferably 1-5) carbon atoms, such as chloromethyl, trifluoromethyl, bromomethyl, 2-chloroethyl or the like, and phenyl optionally substituted with at least one hydroxy and/or $C_1$-$C_5$ alkoxy, such as methoxy, ethoxy, propoxy, butoxy or the like;

or a 5, 6, 7, 8-tetrahydronaphthyl, $C_7$-$C_{12}$ aralkyl, 9, 10-dihydroanthryl, 5, 6, 7, 8-tetrahydroanthryl, 9, 10-dihydrophenanthryl, 1, 2, 3, 4, 5, 6, 7, 8-octahydrophenanthryl, indenyl, indanyl, fluorenyl, acenaphthenyl, phenylthiophenyl, 1, 2-ethylenedioxyphenyl, chromanyl, isochromanyl, 2, 3-dihydrobenzofuranyl, 1, 3-dihydroisobenzofuranyl, 2, 3-ethylenedioxynaphthyl, xanthenyl, thioxanthenyl, 1, 2-trimethylenedioxyphenyl, 2H-chromenyl, 3, 4-dehydro-1-isochromanyl, 4H-chromenyl, indolinyl, isoindolinyl, 1, 2, 3, 4-tetrahydroquinolyl, or 1, 2, 3, 4-tetrahydroisoquinolyl groups each of which is unsubstituted or substituted with one or more groups selected from the group consisting of halo, nitro, cyano, hydroxy, alkyl of 1-10 (preferably 1-5) carbon atoms, such as methyl, ethyl, propyl, butyl or the like, alkoxy of 1-10 (preferably 1-5) carbon atoms, such as methoxy, ethoxy, propoxy, butoxy or the like, dialkylamino of 2-20 (preferably 2-10) carbon atoms, such as dimethylamino, diethylamino, dipropylamino or the like, sulfoamino, carbamoyl, N,N-dialkylcarbamoyl of 3-10 (preferably 3-7) carbon atoms, such as N,N-dimethylcarbamoyl, N,N-diethylcarbamoyl or the like, amino, alkylamino of 1-10 (preferably 1-5) carbon atoms, such as methylamino or the like, mercapto, alkylthio of 1-10 (preferably 1-5) carbon atoms, such as methylthio, ethylthio, propylthio, butylthio or the like, aralkyl of 7-12 (preferably 7-10) carbon atoms, such as benzyl, phenethyl or the like, carboxyl, alkoxycarbonyl of 2-10 (preferably 2-6) carbon atoms, such as methoxycarbonyl, ethoxycarbonyl or the like, carboxyalkyl of 2-10 (preferably 2-6) carbon atoms, such as carboxymethyl, 2-carboxyethyl, 2-caboxypropyl or the like, acylamino such as alkylcarbonylamino of 1-10 (preferably 1-5) carbon atoms, such as acetylamino, propionylamino or the like, alkylcarbonyl of 2-10 (preferably 2-6) carbon atoms, such as acetyl, propionyl, or the like, hydroxyalkyl or 1-10 (preferably 1-5) carbon atoms, such as hydroxymethyl, 2-hydroxyethyl, 2-hydroxypropyl or the like, haloalkyl of 1-10 (preferably 1-5) carbon atoms, such as chloromethyl, trifluoromethyl, bromomethyl, 2-chloroethyl or the like, oxo and phenyl optionally substituted with at least one hydroxy and/or $C_1$-$C_5$ alkoxy, such as methoxy, ethoxy, propoxy, butoxy or the like.

Illustrative of suitable $N^2$-arylsulfonyl-L-argininamides are those shown in the table below. In this table, the prior art reference cited in the second column discloses a method of preparation for the compound listed in the second column. The Example No. listed in the last column refers to an Example of this application which discloses the details of a method by which the product compound of the fifth column of the table may be prepared.

TABLE I
| NO. | ArSO$_2$Cl or ArSO$_3$H or salt thereof (Literature reference) | Starting material: Amino acid ester | Ar | Product 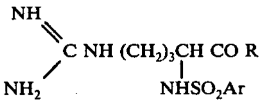 R | Preparation Procedure |
|---|---|---|---|---|---|
| 1 | 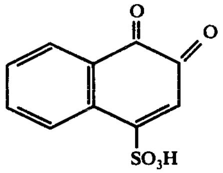 Ger.1,123,315 | 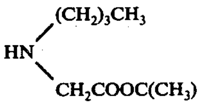 | 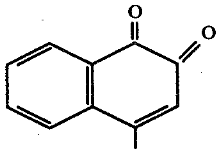 | 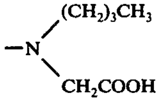 | 1 |
| 2 | 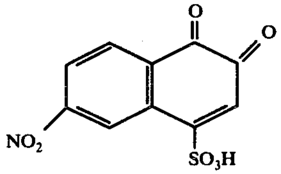 Ger. 1,123,315 | 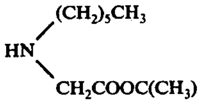 | 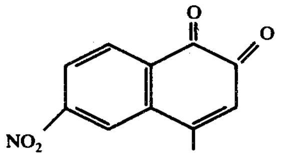 | 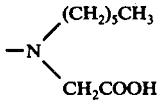 | 1 |
| 3 | 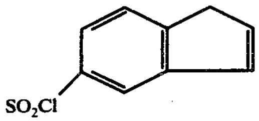 Ber. 54,102(1921) | 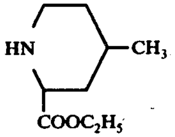 | 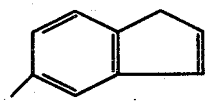 | 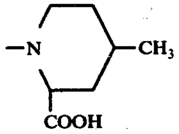 | 2 |
| 4 | 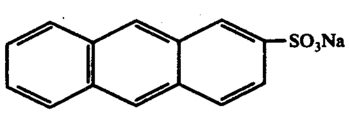 CA 23,1897 | 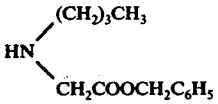 | 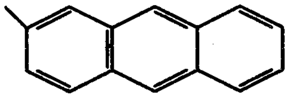 | 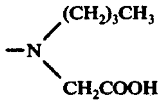 | 2 |
| 5 | 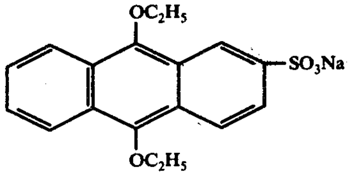 CA 25,5420 | 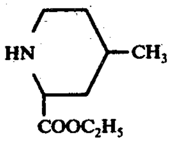 | 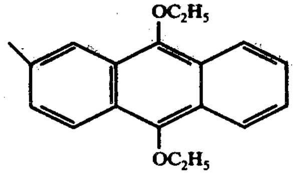 | 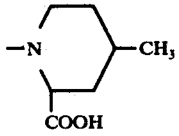 | 2 |

TABLE I-continued
| NO. | ArSO$_2$Cl or ArSO$_3$H or salt thereof (Literature reference) | Starting material: Amino acid ester | Ar | Product 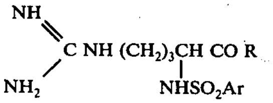 R | Preparation Procedure |
|---|---|---|---|---|---|
| 6 | 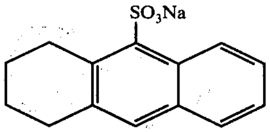 CA 22,413 | 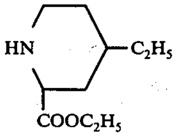 | 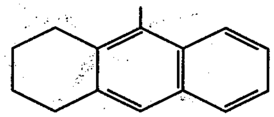 | 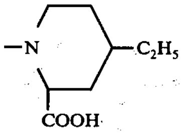 | 2 |
| 7 | 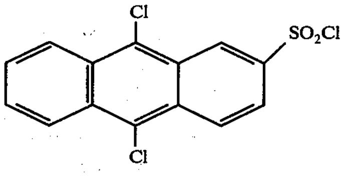 J. Ger. Chem. 6,444(1936) | 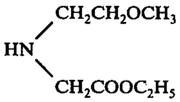 | 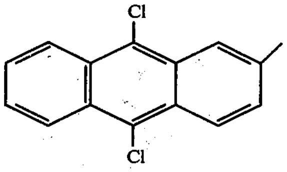 | 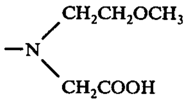 | 2 |
| 8 | 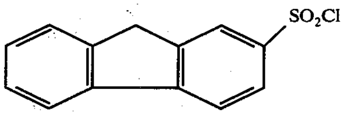 Compt. rend 218,973(1944) | 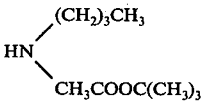 | 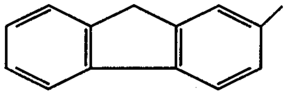 | 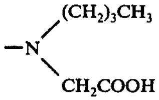 | 1 |
| 9 | 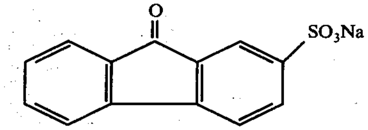 CA 33 4227 | 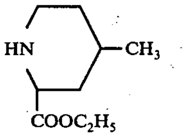 | 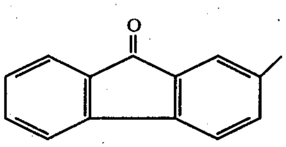 | 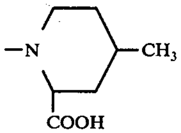 | 2 |
| 10 | 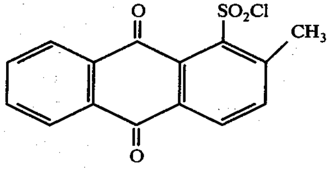 Can. J. Chem 41,100(1963) | 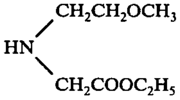 | 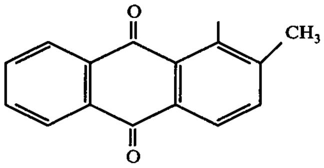 | 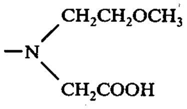 | 2 |

TABLE I-continued
| NO. | $ArSO_2Cl$ or $ArSO_3H$ or salt thereof (Literature reference) | Starting material Amino acid ester | Ar | Product 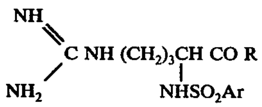 R | Preparation Procedure |
|---|---|---|---|---|---|
| 11 | 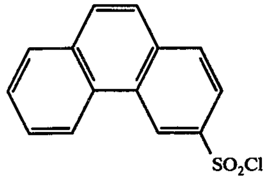 Compt. rend 218,973(1944) | 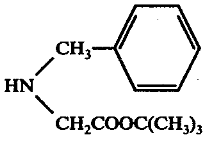 | 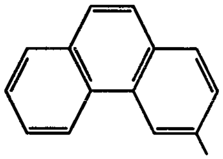 | 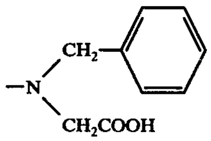 | 1 |
| 12 | 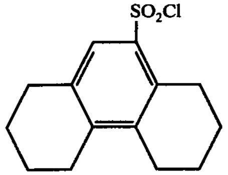 CA 49,5414 | 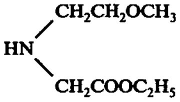 | 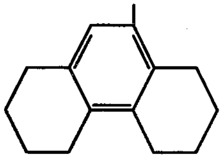 | 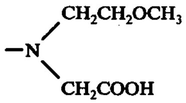 | 2 |
| 13 | 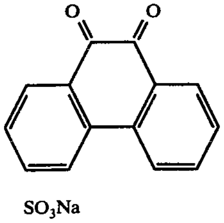 Naturwisserschaften 49,57(1962) | 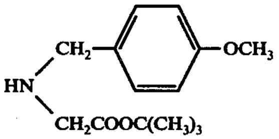 | 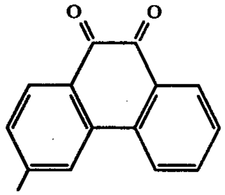 | 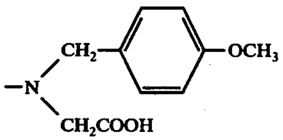 | 1 |
| 14 | 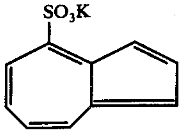 Z. Chem. 3,426(1963) | 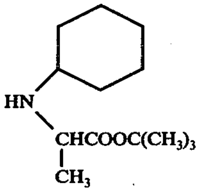 | 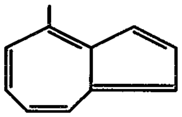 | 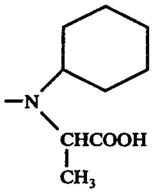 | 1 |

TABLE I-continued
| NO. | ArSO2Cl or ArSO3H or salt thereof (Literature reference) | Starting material: Amino acid ester | Ar | Product 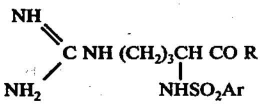 R | Preparation Procedure |
|---|---|---|---|---|---|
| 15 | 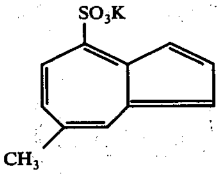 Z. Chem. 3,426(1963) | 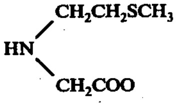 | 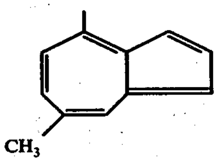 | 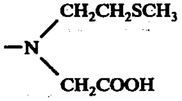 | 1 |
| 16 | 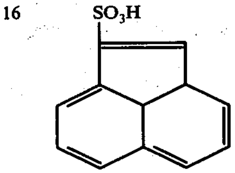 Ger. 1,219,477 | 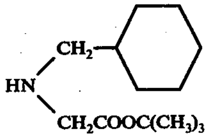 | 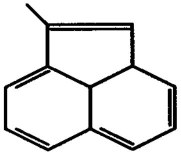 | 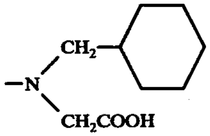 | 1 |
| 17 | 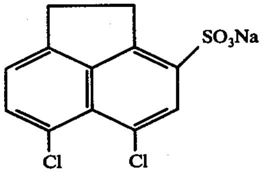 Kogyo. Kaga Ku. Zashi 62,703(1967) | 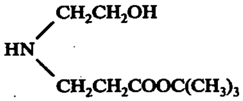 | 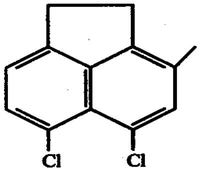 | 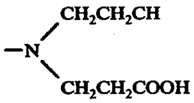 | 1 |
| 18 | 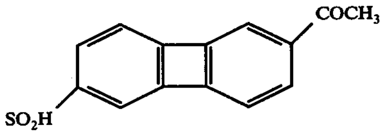 J.Chem. Soc. 1970,2500 | 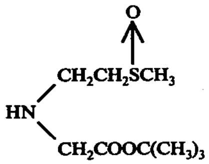 | 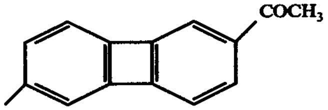 | 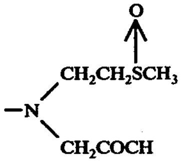 | 1 |
| 19 | 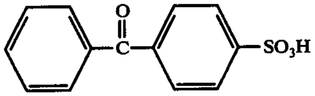 Ber 31,1663 | 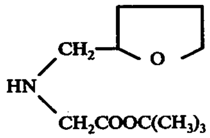 | 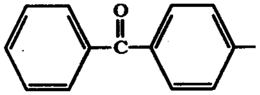 | 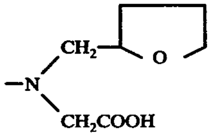 | 1 |

TABLE I-continued
| NO. | ArSO₂Cl or ArSO₃H or salt thereof (Literature reference) | Starting material: Amino acid ester | Starting material: Ar | Product 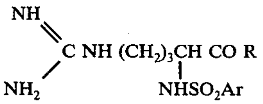 R | Preparation Procedure |
|---|---|---|---|---|---|
| 20 | 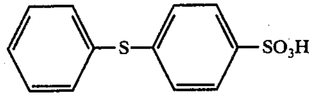 Ber 26,906 | 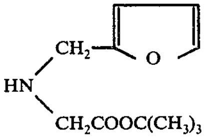 | 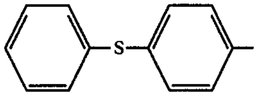 | 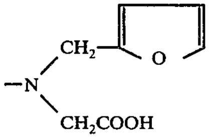 | 1 |
| 21 | 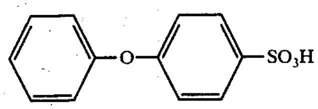 Beilstein 11I,135 | 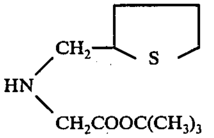 | 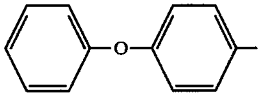 | 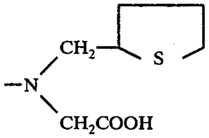 | 1 |
| 22 | 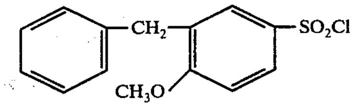 mp 88–9° | 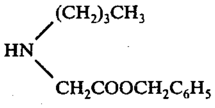 | 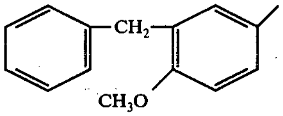 | 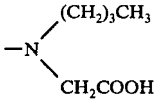 | 3 |
| 23 | 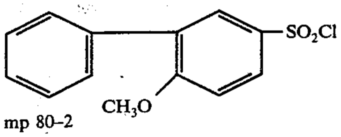 mp 80–2 | 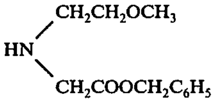 | 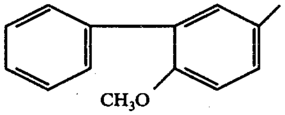 | 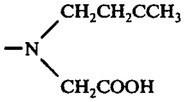 | 3 |
| 24 | 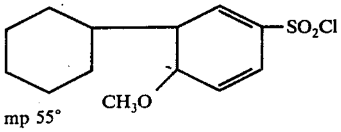 mp 55° | 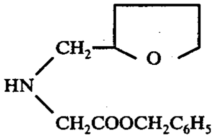 | 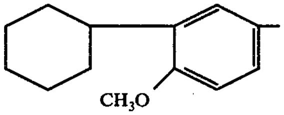 | 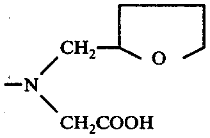 | 3 |
| 25 | 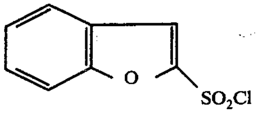 Ger 56780 (CA68,127or | 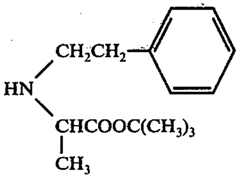 | 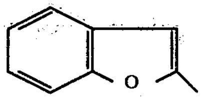 | 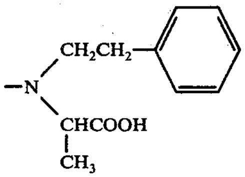 | 1 |

TABLE I-continued
| NO. | ArSO$_2$Cl or ArSO$_3$H or salt thereof (Literature reference) | Starting material: Amino acid ester | Ar | Product 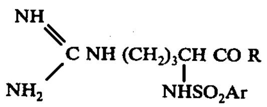 R | Preparation Procedure |
|---|---|---|---|---|---|
| 26 | 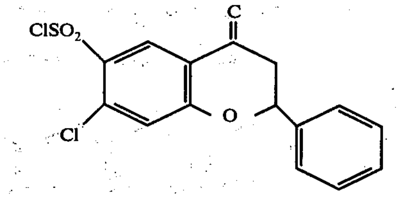 Helv. chem. Acta 46,72781963 | 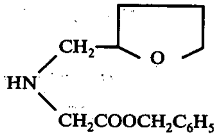 | 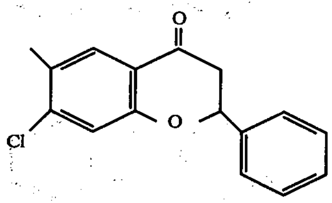 | 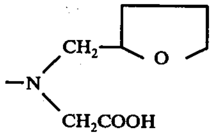 | 3 |
| 27 | 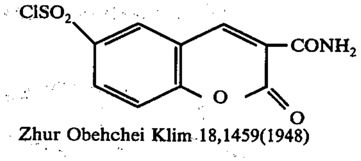 Zhur Obehchei Klim 18,1459(1948) | 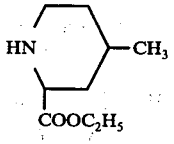 | 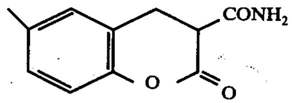 | 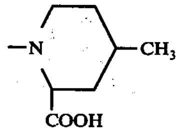 | 2 |
| 28 | 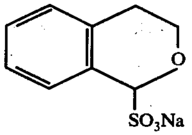 Per 84,1254(1956) | 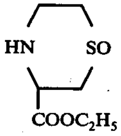 | 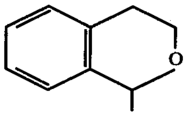 | 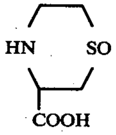 | 2 |
| 29 | 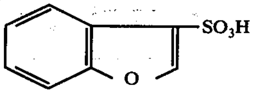 CA.47,10519 | 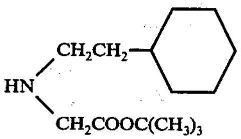 | 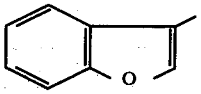 | 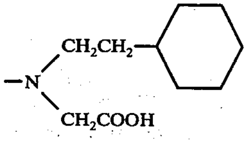 | 1 |
| 30 | 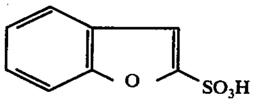 CA.32,2938 | 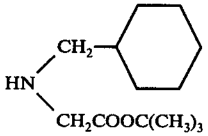 | 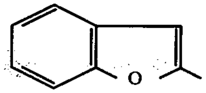 | 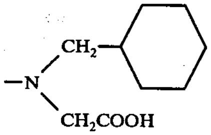 | 1 |

TABLE I-continued
| NO. | ArSO2Cl or ArSO3H or salt thereof (Literature reference) | Starting material: Amino acid ester | Ar | Product 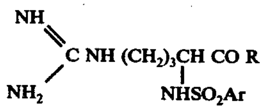 R | Preparation Procedure |
|---|---|---|---|---|---|
| 31 | 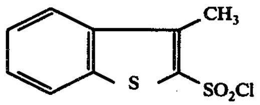 Monatsh.92,677(1961) | 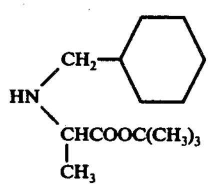 | 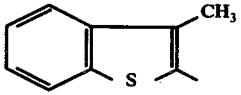 | 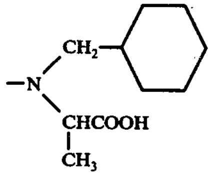 | 1 |
| 32 | 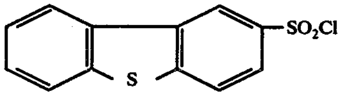 Conept.rend 198,2260(1934) | 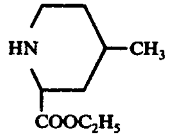 | 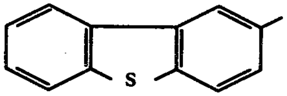 | 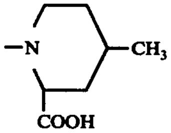 | 2 |
| 33 | 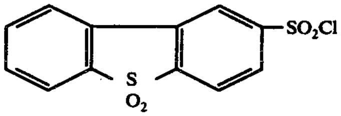 Compt. rend 198,2260(1934) | 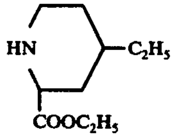 | 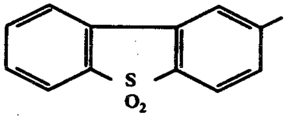 | 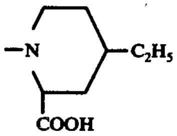 | 2 |
| 34 | 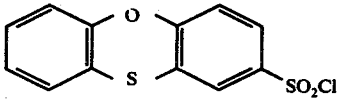 J.Am.Chem.Soc.58,717(1936) | 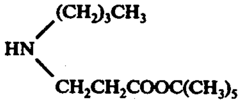 | 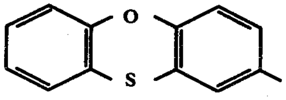 | 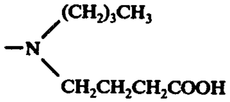 | 1 |
| 35 | 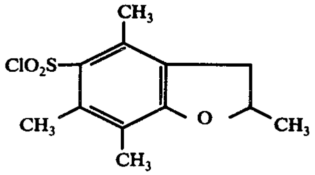 Montash. 85,235(1954) | 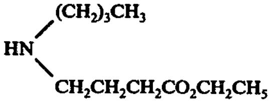 | 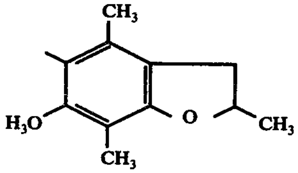 | 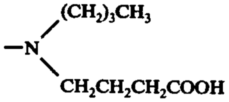 | 3 |

TABLE I-continued
| NO. | ArSO$_2$Cl or ArSO$_3$H or salt thereof (Literature reference) | Starting material: Amino acid ester | Ar | Product 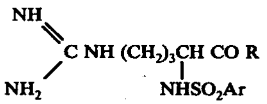 R | Preparation Procedure |
|---|---|---|---|---|---|
| 36 | 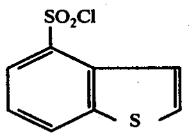 J.Chem.Eng.Data 12,610(1967) | 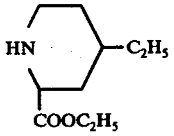 | 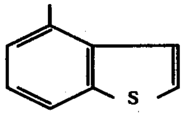 | 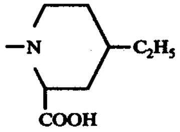 | 2 |
| 37 | 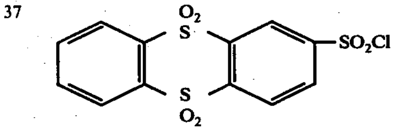 J.Ger.Chem. 10,1077(1940) | 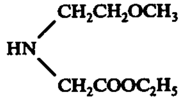 | 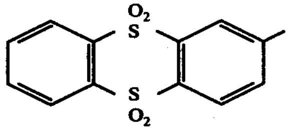 | 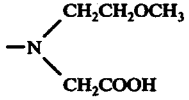 | 2 |
| 38 | 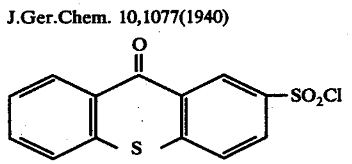 J.Pharm.Soc.Japan 73,1878(1953) | 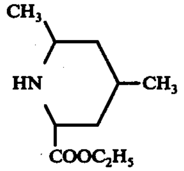 | 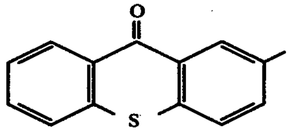 | 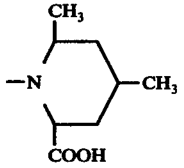 | 2 |
| 39 | 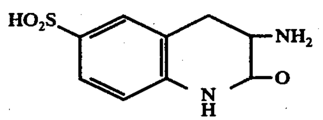 J.Pharm.Soc.Japan 76,103(1958) | 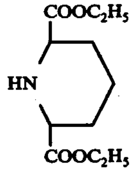 | 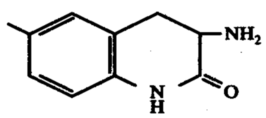 | 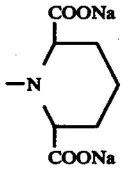 | 2 |
| 40 | 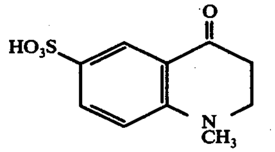 J.Chem.Soc 1958,3830 | 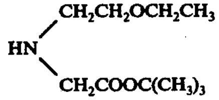 | 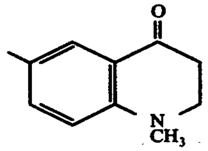 | 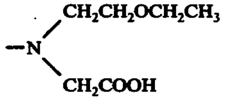 | 1 |

TABLE I-continued
| NO. | ArSO2Cl or ArSO3H or salt thereof (Literature reference) | Starting material: Amino acid ester | Starting material: Ar | Product 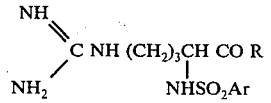 R | Preparation Procedure |
|---|---|---|---|---|---|
| 41 | 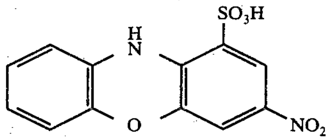 J.Chem.Soc 1958,1499 | 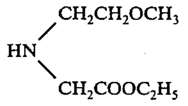 | 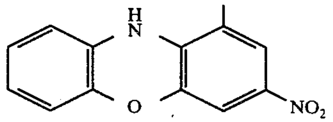 | 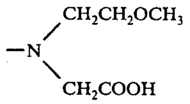 | 2 |
| 42 | 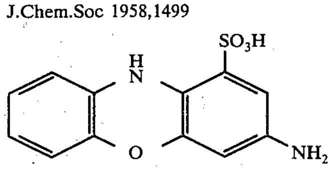 | 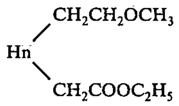 | 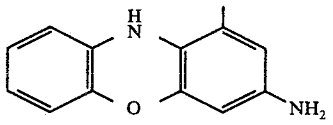 | 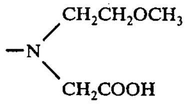 | 2 |
| 43 | 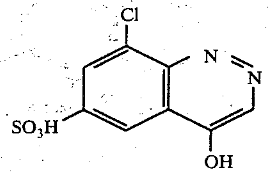 J. Chem Soc 1968,687 | 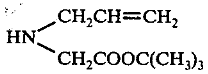 | 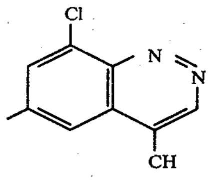 | 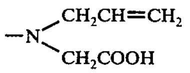 | 1 |
| 44 | 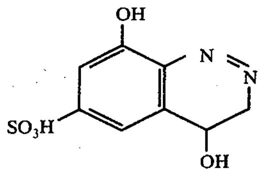 J. Chem. Soc 1968,687 | 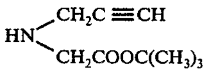 | 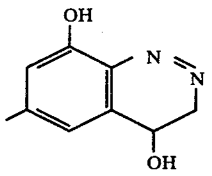 | 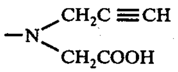 | 1 |
| 45 | 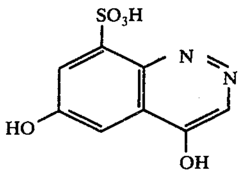 J. Chem. Soc 1968,687 | 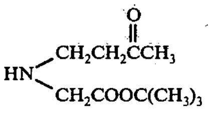 | 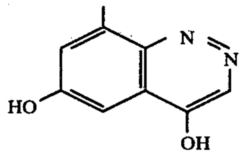 | 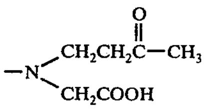 | 1 |

TABLE I-continued
| NO. | ArSO$_2$Cl or ArSO$_3$H or salt thereof (Literature reference) | Starting material: Amino acid ester | Ar | Product 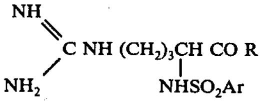 R | Preparation Procedure |
| --- | --- | --- | --- | --- | --- |
| 46 | 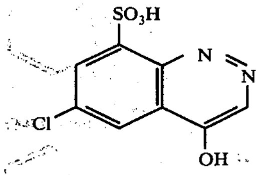 J. Chem. Soc. 1968,687 | 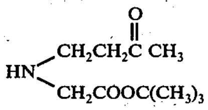 | 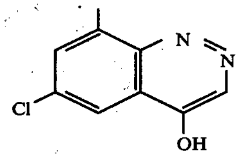 | 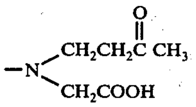 | 1 |
| 47 | 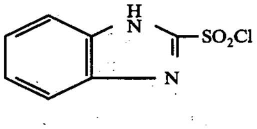 J. Chem. Soc. 72,4890(1950) | 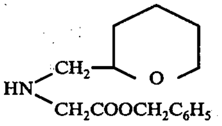 | 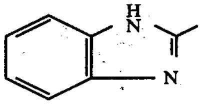 | 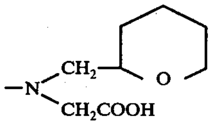 | 3 |
| 48 | 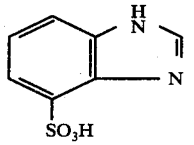 U.S. Pat. No. 2,476,541 | 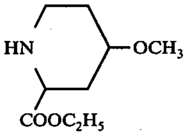 | 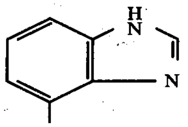 | 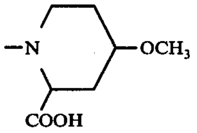 | 2 |
| 49 | 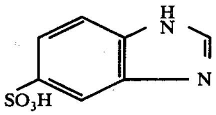 Zhur Obschei Khem 23,842 | 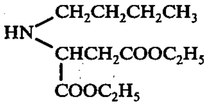 | 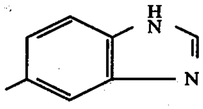 | 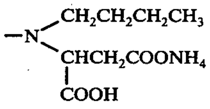 | 2 |
| 50 | 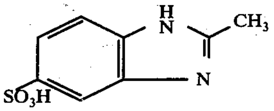 Zhur Obschei Khem 23,842 | 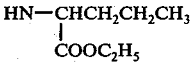 | 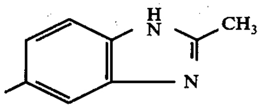 | 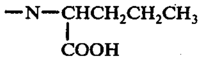 | 2 |
| 51 | 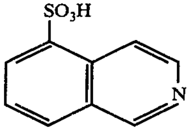 J. Am. Chem. Soc. 75,2095(1853) | 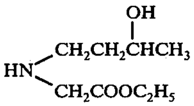 | 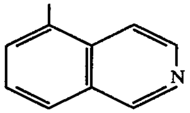 | 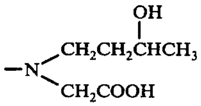 | 2 |

TABLE I-continued
| NO. | $ArSO_2Cl$ or $ArSO_3H$ or salt thereof (Literature reference) | Starting material: Amino acid ester | Ar | Product 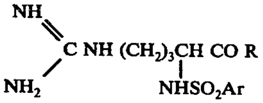 R | Preparation Procedure |
|---|---|---|---|---|---|
| 52 | 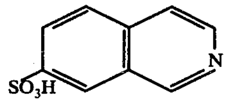 Brit 590,645(1747) | 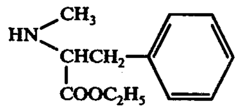 | 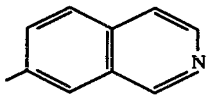 | 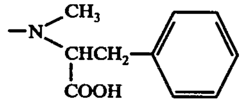 | 2 |
| 53 | 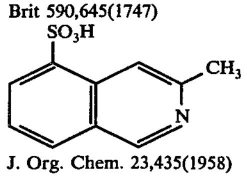 J. Org. Chem. 23,435(1958) | 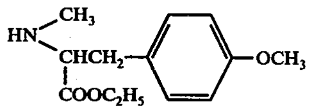 | 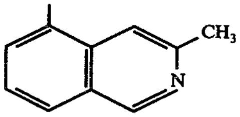 | 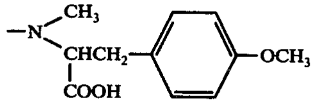 | 2 |
| 54 | 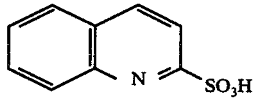 U.S. Pat. No. 2,768,669 | 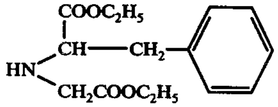 | 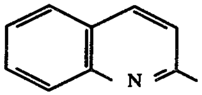 | 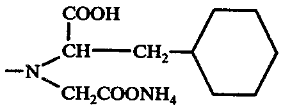 | 2 |
| 55 | 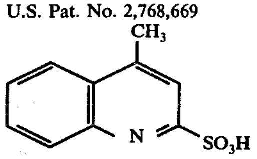 Gazz. Chem. ital. 81,764(1959) | 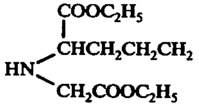 | 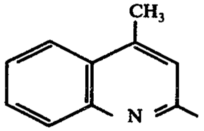 | 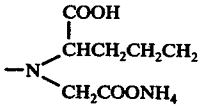 | 2 |
| 56 | 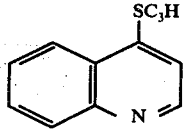 Pharm. Bull.(Japan)5,297(1954) | 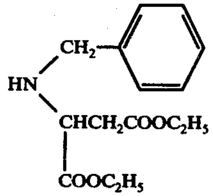 | 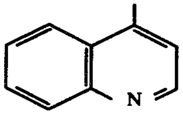 | 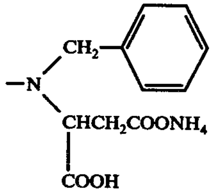 | 2 |
| 57 | 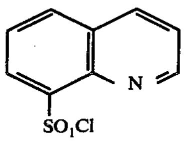 (Aldrich) | 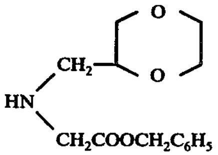 | 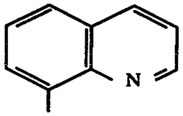 | 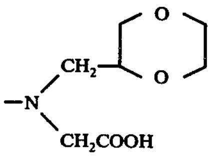 | 3 |

TABLE I-continued
| NO. | ArSO$_2$Cl or ArSO$_3$H or salt thereof (Literature reference) | Starting material Amino acid ester | Ar | Product 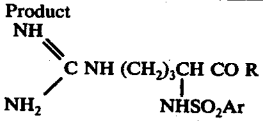 R | Preparation Procedure |
|---|---|---|---|---|---|
| 58 | 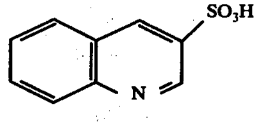 Pharmazie 20,549 | 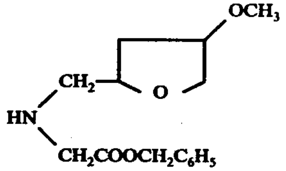 | 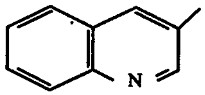 | 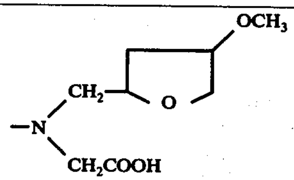 | 3 |
| 59 | 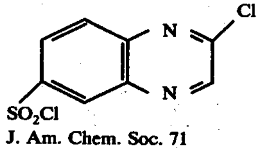 J. Am. Chem. Soc. 71 | 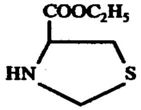 | 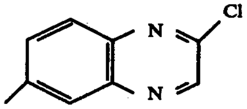 | 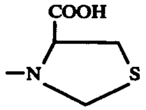 | 2 |
| 60 | 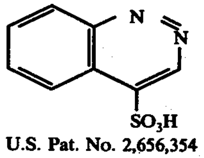 U.S. Pat. No. 2,656,354 | 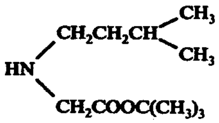 | 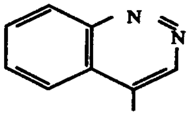 | 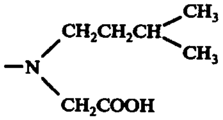 | 1 |
| 61 | 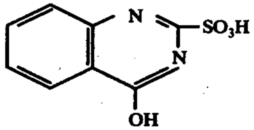 | 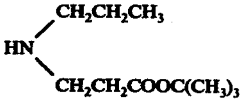 | 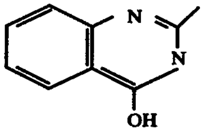 | 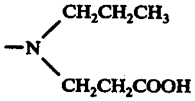 | 1 |
| 62 | 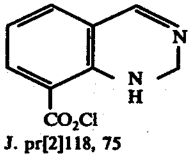 J. pr[2]118, 75 | 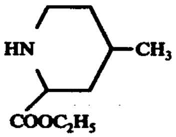 | 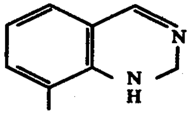 | 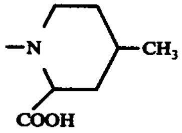 | 2 |
| 63 | 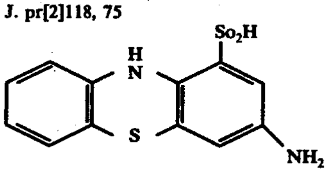 Photophysik Photochem 58, 3 (1963) | 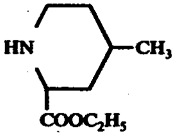 | 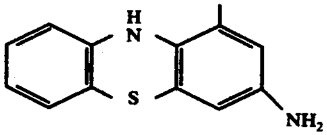 | 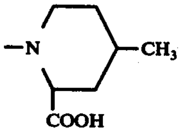 | 2 |

TABLE I-continued
| NO. | ArSO$_2$Cl or ArSO$_3$H or salt thereof (Literature reference) | Starting material Amino acid ester | Ar | Product 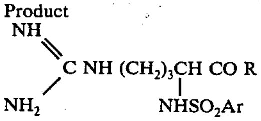 R | Preparation Procedure |
|---|---|---|---|---|---|
| 64 | 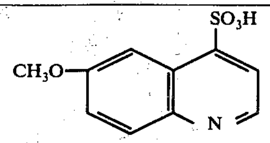 | 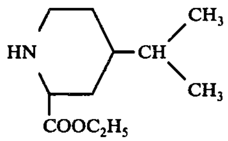 | 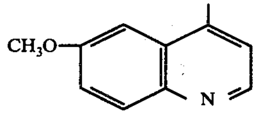 | 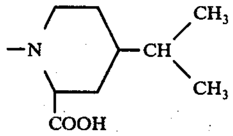 | 2 |
| 65 | J. Chem. 16, 1873 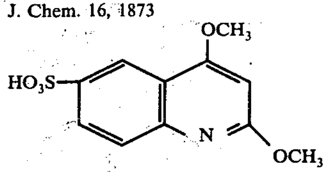 | 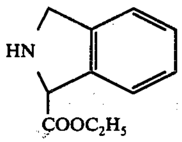 | 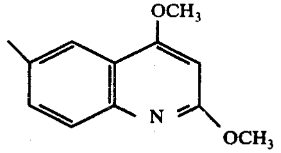 | 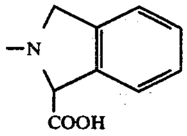 | 2 |
| 66 | Ber., 86, 951 (1953) 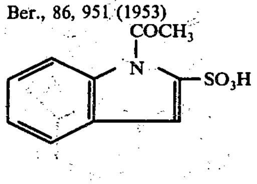 | 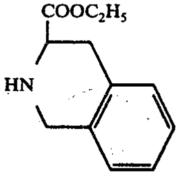 | 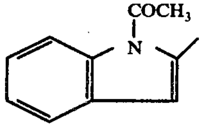 | 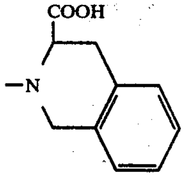 | 2 |
| 67 | Ber 86, 951 (1963) 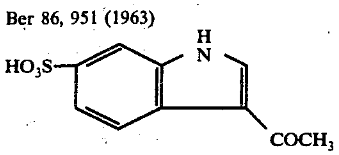 | 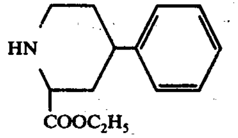 | 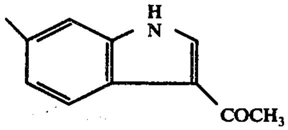 | 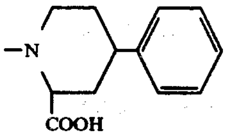 | 2 |
| 68 | Ber 86, 951 (1953) 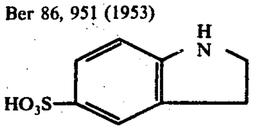 | 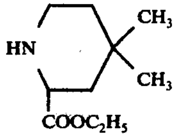 | 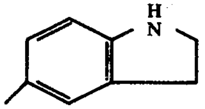 | 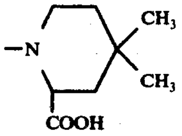 | 2 |
| 69 | Zhur Obschei Khim 30, 1218 (1960) 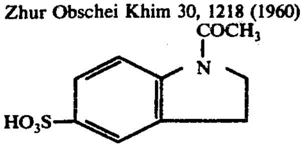 | 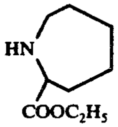 | 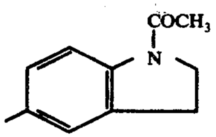 | 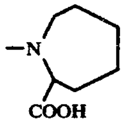 | 2 |

TABLE I-continued
| NO. | ArSO$_2$Cl or ArSO$_3$H or salt thereof (Literature reference) | Starting material Amino acid ester | Ar | Product 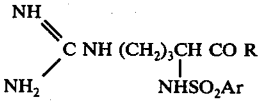 R | Preparation Procedure |
|---|---|---|---|---|---|
| 70 | Zhur Obschei Kim 30, 1218 (1960) 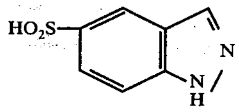 | 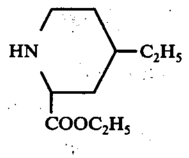 | 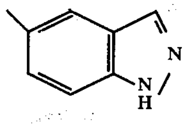 | 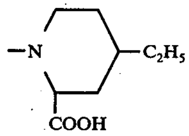 | 2 |
| 71 | Bull. Soc Chem France 1950, 466 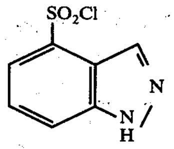 | 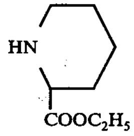 | 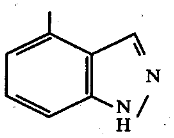 | 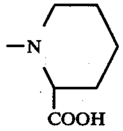 | 2 |
| 72 | Bull. Soc. Chem France 1950, 466 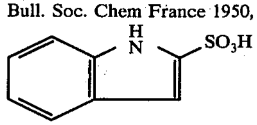 | 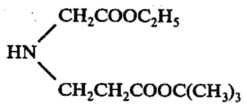 | 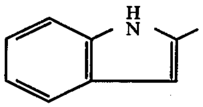 | 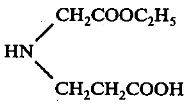 | 1 |
| 73 | Zhur. Obschei Khim 22, 866 (1952) 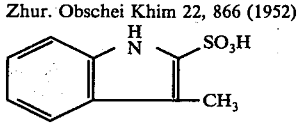 | 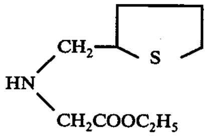 | 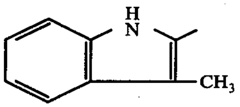 | 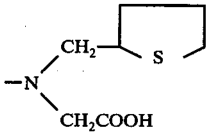 | 2 |
| 74 | Zhur Obschei Khim 22, 866 (1952) 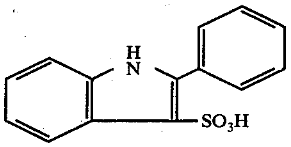 | 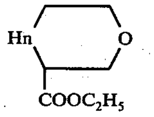 | 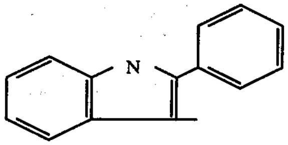 | 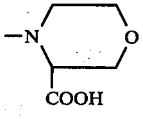 | 2 |
| 75 | Zhur Obschei Khim 23, 866 (1952) 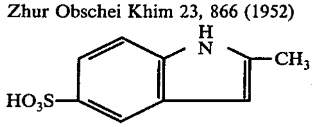 | 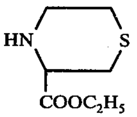 | 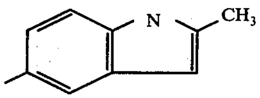 | 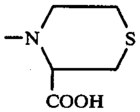 | 2 |
| | Zhur Obschei Khim 23, 866 (1952) | | | | |

TABLE I-continued
| NO. | ArSO2Cl or ArSO3H or salt thereof (Literature reference) | Starting material Amino acid ester | Ar | Product 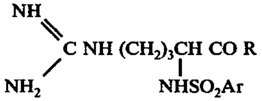 R | Preparation Procedure |
|---|---|---|---|---|---|
| 76 | 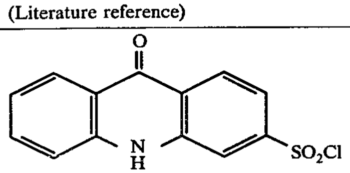 | 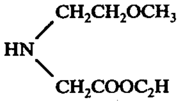 | 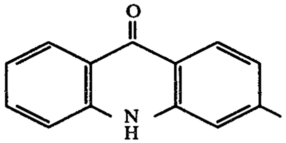 | 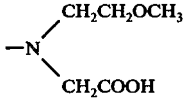 | 2 |
| 77 | 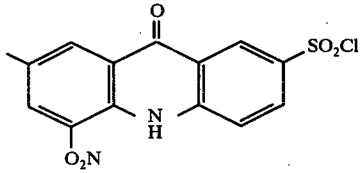 | 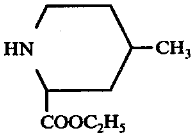 | 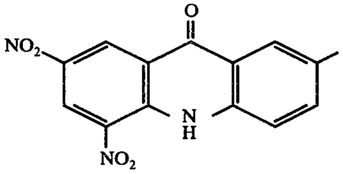 | 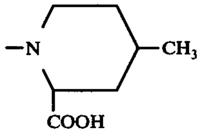 | 2 |
| 78 | CA 62, 14675G 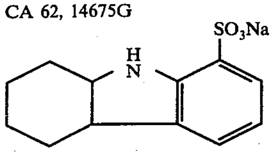 | 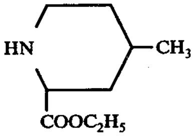 | 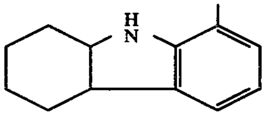 | 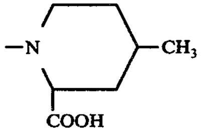 | 2 |
| 79 | CA 26 4723 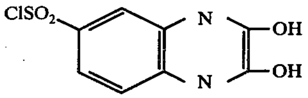 | 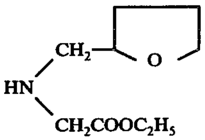 | 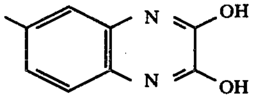 | 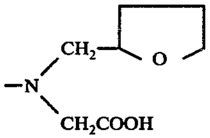 | 2 |
| 80 | Japanese Patent Published 39-26975 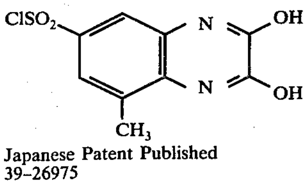 | 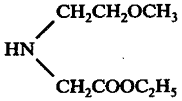 | 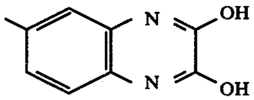 | 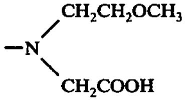 | 2 |
| 81 | Japanese Patent Published 39-26975 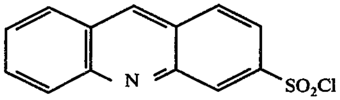 J. Am. Chem. Soc. 57,1533(1935) | 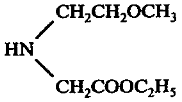 | 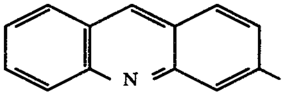 | 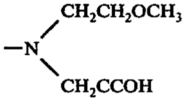 | 2 |

TABLE I-continued
| NO. | ArSO$_2$Cl or ArSO$_3$H or salt thereof (Literature reference) | Starting material Amino acid ester | Ar | Product 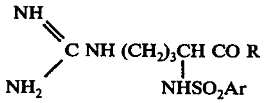 R | Preparation Procedure |
|---|---|---|---|---|---|
| 82 | 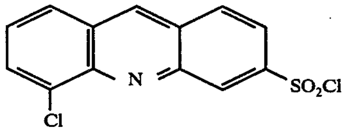 J. Am. Chem. Soc. 59,15338(1935) | 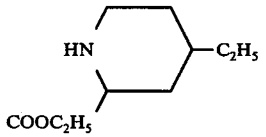 | 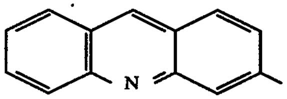 | 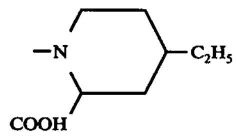 | 2 |
| 83 | 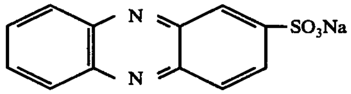 CA 45 90636 | 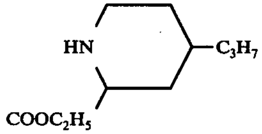 | 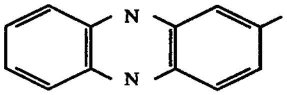 | 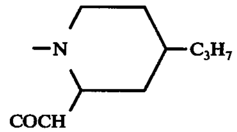 | 2 |
| 84 | 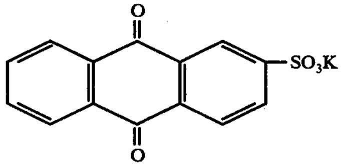 Org. Synth II. 539 | 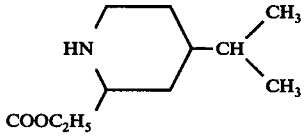 | 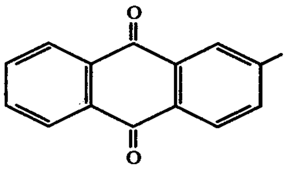 | 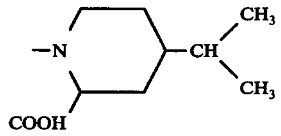 | 2 |
| 85 | 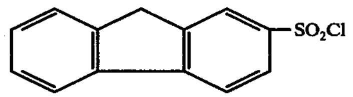 (No. 8) | 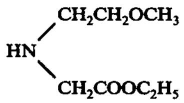 | 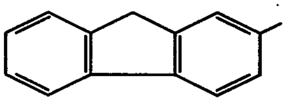 | 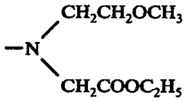 | 3 |
| 86 | " | 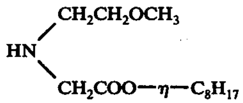 | 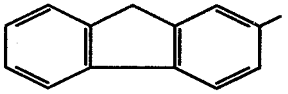 | 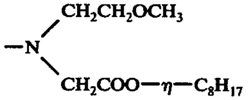 | 3 |
| 87 | " | 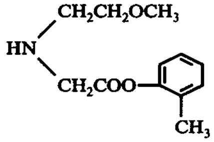 | 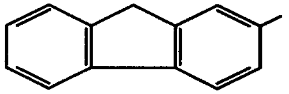 | 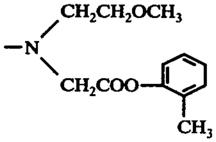 | 6 |

TABLE I-continued

| NO. | ArSO2Cl or ArSO3H or salt thereof (Literature reference) | Starting material<br>Amino acid ester | Product 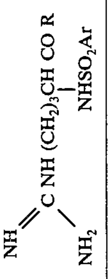<br>Ar | R | Preparation Procedure |
|---|---|---|---|---|---|
| 88 | " | 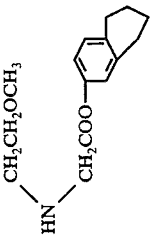 | 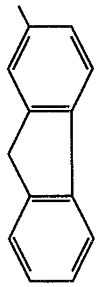 | 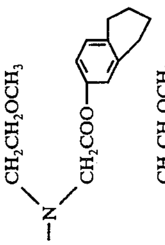 | 6 |
| 89 | " | 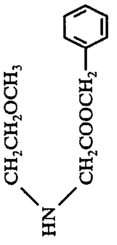 | 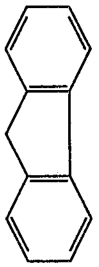 | 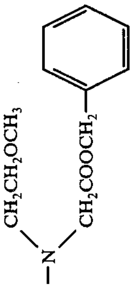 | 3 |

Also illustrative of suitable $N^2$-arylsulfonyl-L-argininamides are those shown in the table below. In this table, the Example No. listed in the sixth column refers to the Example of this application by which the compound in the first column was prepared.

Table 2

| Sample No. | Compound<br>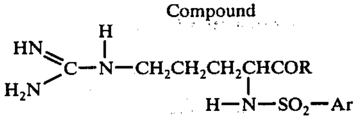 (I)<br>Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) (cm$^{-1}$) |
|---|---|---|---|---|---|---|---|---|---|---|
| 1 | 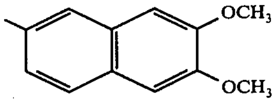 | 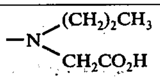 | — | 8 | 1 | powder | 52.76<br>52.68 | 6.35<br>6.21 | 13.38<br>13.30 | 3,360<br>3,160<br>1,620 |
| 2 | " | 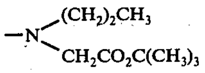 | ½ $H_2SO_3$ | | 1 | 134-6 | 52.25<br>52.07 | 6.82<br>6.73 | 11.29<br>10.89 | 3,360<br>3,180<br>1,740<br>1,375 |
| 3 | " | 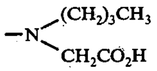 | — | 0.3 | 1 | powder | 53.62<br>53.48 | 6.56<br>6.43 | 13.03<br>12.98 | 3,360<br>3,140<br>1,622 |
| 4 | " | 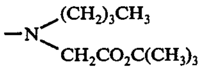 | ½ $H_2SO_3$ | | 1 | 164-6 | 52.98<br>52.69 | 7.00<br>6.98 | 11.04<br>10.86 | 3,390<br>3,165<br>1,735<br>1,370 |
| 5 | " | 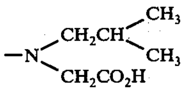 | — | 2 | 1 | powder | 53.62<br>53.43 | 6.56<br>6.51 | 13.03<br>13.12 | 3,360<br>3,160<br>1,620 |
| 6 | " | 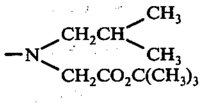 | ½ $H_2SO_3$ | | 1 | " | 52.98<br>52.59 | 7.00<br>6.79 | 11.04<br>10.89 | 3,390<br>3,170<br>1,737<br>1,370 |
| 7 | " | 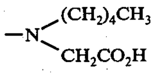 | — | 5 | 1 | " | 54.43<br>54.38 | 6.76<br>6.79 | 12.70<br>12.56 | 3,350<br>3,180<br>1,630 |
| 8 | " | 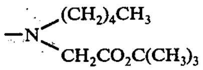 | ½ $H_2SO_3$ | | 1 | 195-6 | 53.69<br>53.40 | 7.15<br>7.12 | 10.80<br>10.56 | 3,380<br>3,180<br>1,738<br>1,375 |
| 9 | " | 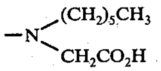 | — | 1.5 | 1 | powder | 55.21<br>54.98 | 6.95<br>7.02 | 12.38<br>12.47 | 3,360<br>3,200<br>1,622 |
| 10 | " | 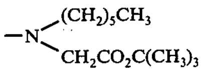 | ½ $H_2SO_3$ | | 1 | 198-200 | 54.37<br>54.30 | 7.30<br>7.27 | 10.57<br>10.36 | 3,360<br>3,160<br>1,730<br>1,368 |

Table 2-continued

Compound 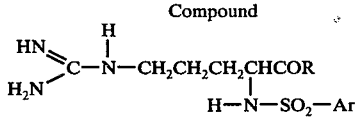 (I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 11 | " | 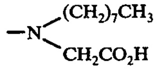 | — | | 1 | powder | 56.64<br>56.41 | 7.30<br>7.17 | 11.80<br>11.51 | 3,360<br>3,180<br>1,620 |
| 12 | " | 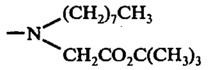 | ½ $H_2SO_3$ · | | 1 | 172–174 | 55.64<br>55.31 | 7.59<br>7.63 | 10.14<br>10.18 | 3,380<br>3,180<br>1,740<br>1,375 |
| 13 | " | 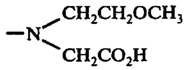 | — | 0.5 | 3 | powder | 51.20<br>50.93 | 6.17<br>6.02 | 12.98<br>12.63 | 3,380<br>3,180<br>1,630 |
| 14 | " | 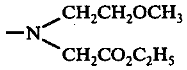 | 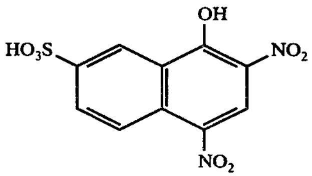 | 1.5 | 3 | 185 | 47.67<br>47.64 | 4.92<br>4.81 | 11.12<br>11.12 | 3,375<br>3,200<br>1,740 |
| 15 | " | 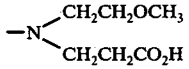 | — | 2.5 | 3 | powder | 52.07<br>52.21 | 6.37<br>6.04 | 12.67<br>12.51 | 3,380<br>3,200<br>1.620 |
| 16 | " | 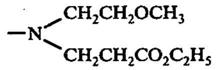 | — | | 3 | " | 53.69<br>53.53 | 6.76<br>6.69 | 12.04<br>12.38 | 3,380<br>3,200<br>1,740 |
| 17 | " | 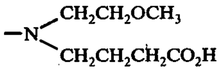 | — | 2.5 | 1· | " | 52.90<br>52.71 | 6.57<br>6.43 | 12.34<br>12.46 | 3,350<br>3,160<br>1,640 |
| 18 | " | 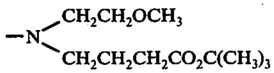 | ½ $H_2SO_3$ | | 1 | " | 52.40<br>52.16 | 6.96<br>7.13 | 10.54<br>10.28 | 3,340<br>3,160<br>1,736<br>1,380 |
| 19 | " | 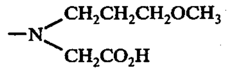 | — | 5 | 1 | " | 52.07<br>51.91 | 6.37<br>6.19 | 12.65<br>12.38 | 3,360<br>3,160<br>1,620 |
| 20 | " | 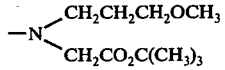 | ½ $H_2SO_3$ | | 1 | " | 51.68<br>51.43 | 6.82<br>6.66 | 10.76<br>10.58 | 3,380<br>3,160<br>1,740<br>1,370 |

Table 2-continued

| Sample No. | Compound 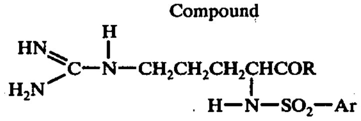 (I) Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) (cm⁻¹) |
|---|---|---|---|---|---|---|---|---|---|---|
| 21 | " | 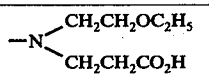 | — | 4 | 1 | " | 52.90<br>52.59 | 6.57<br>6.41 | 12.34<br>12.16 | 3,360<br>3,160<br>1,640 |
| 22 | " | 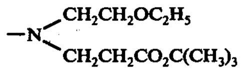 | ½ $H_2SO_3$ | | 1 | powder | 52.98<br>52.73 | 7.00<br>7.00 | 11.04<br>10.82 | 3,377<br>3,160<br>1,740<br>1,368 |
| 23 | 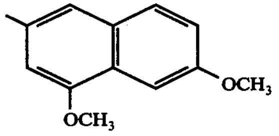 | 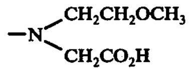 | — | 4 | 4 | " | 51.20<br>51.31 | 6.17<br>6.01 | 12.98<br>12.67 | 3,360<br>3,180<br>1,610 |
| 24 | " | 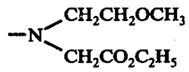 | 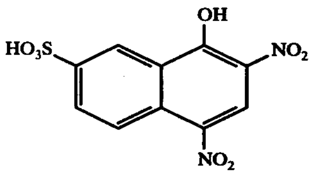 | | 4 | 225-7 | 47.67<br>47.62 | 4.92<br>4.84 | 11.12<br>11.18 | 3,375<br>3,200<br>1,742 |
| 25 | " | 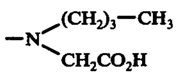 | — | 2 | 1 | powder | 53.62<br>53.58 | 6.56<br>6.48 | 13.03<br>12.94 | 3,380<br>3,200<br>1,630 |
| 26 | " | 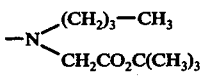 | ½ $H_2SO_3$ | | 1 | 224 | 52.98<br>52.73 | 7.00<br>7.00 | 11.04<br>10.82 | 3,360<br>3,160<br>1,740<br>1,370 |
| 27 | 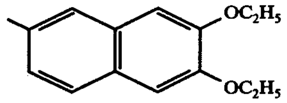 | 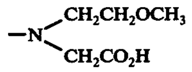 | — | 15 | 1 | powder | 52.89<br>52.77 | 6.57<br>6.80 | 12.34<br>12.59 | 3,380<br>3,200<br>1,625 |
| 28 | " | 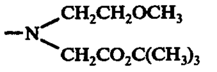 | ½ $H_2SO_3$ | | 1 | " | 52.39<br>52.10 | 6.97<br>6.84 | 10.54<br>10.21 | 3,370<br>3,150<br>1,740<br>1,370 |

Table 2-continued

| Sample No. | Compound 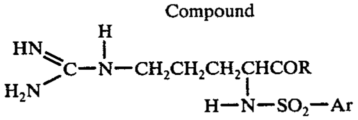 (I) Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 29 | " | 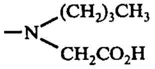 | — | | 1 | powder | 55.20<br>55.00 | 6.95<br>6.81 | 12.38<br>12.21 | 3,360<br>3,150<br>1,620 |
| 30 | " | 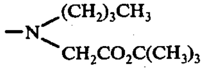 | ½ $H_2SO_3$ | | 1 | " | 54.36<br>54.25 | 7.30<br>7.11 | 10.57<br>10.81 | 3,370<br>3,200<br>1,735<br>1,370 |
| 31 | 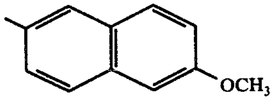 | 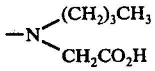 | — | 0.5 | 1 | " | 54.43<br>54.21 | 6.55<br>6.50 | 13.80<br>13.79 | 3,360<br>3,180<br>1,632 |
| 32 | " | 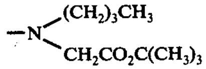 | ½ $H_2SO_3$ | | 1 | " | 53.63<br>53.50 | 7.00<br>6.79 | 11.58<br>11.40 | 3,380<br>3,200<br>1,740<br>1,370 |
| 33 | " | 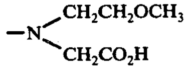 | — | | 1 | " | 51.86<br>51.64 | 6.13<br>6.09 | 13.75<br>13.84 | 3,370<br>3,200<br>1,625 |
| 34 | " | 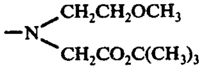 | ½ $H_2SO_3$ | | 1 | " | 55.21<br>55.11 | 6.95<br>6.75 | 12.38<br>12.27 | 3,380<br>3,180<br>1,738<br>1,368 |
| 35 | 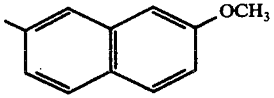 | 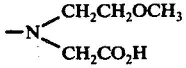 | — | 0.5 | 3 | " | 51.86<br>51.72 | 6.13<br>6.11 | 13.75<br>13.63 | 3,370<br>3,160<br>1,620 |
| 36 | " | 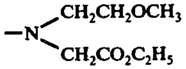 | 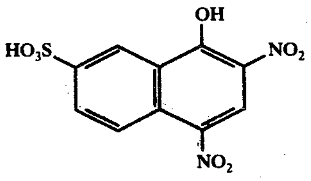 | | 3 | 158-160 | 47.94<br>47.83 | 4.85<br>4.80 | 11.51<br>11.43 | 3,375<br>3,200<br>1,740 |
| 37 | " | 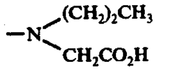 | — | | 1 | powder | 53.53<br>53.40 | 6.33<br>6.21 | 14.19<br>14.04 | 3,375<br>3,150<br>1,620 |

Table 2-continued

Compound

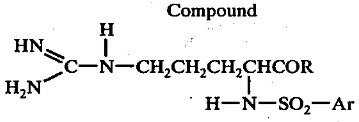 (I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 38 | " | 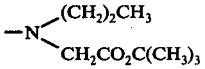 | ½ $H_2SO_3$ | | 1 | " | 52.86<br>52.77 | 6.83<br>6.66 | 11.86<br>11.75 | 3,380<br>3,200<br>1,740<br>1,370 |
| 39 | " | 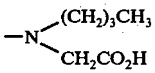 | — | 0.5 | 1 | " | 54.43<br>54.22 | 6.55<br>6.31 | 13.80<br>13.59 | 3,380<br>3,150<br>1,620 |
| 40 | " | 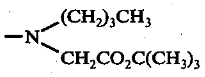 | ½ $H_2SO_3$ | | 1 | 131-137 (dec.) | 53.63<br>53.40 | 7.00<br>7.10 | 11.58<br>11.40 | 3,380<br>3,160<br>1,750<br>1,640 |
| 41 | " | 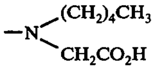 | — | | 1 | powder | 55.26<br>55.21 | 6.76<br>6.65 | 13.43<br>13.29 | 3,360<br>1,630 |
| 42 | " | 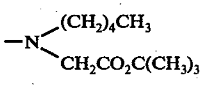 | ½ $H_2SO_3$ | | 1 | 169-175 (dec.) | 54.35<br>54.27 | 7.17<br>7.00 | 11.32<br>11.08 | 3,350<br>3,180<br>1,740<br>1,640 |
| 43 | 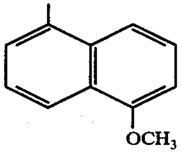 | 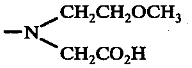 | — | 2.5 | 1 | powder | 51.86<br>51.77 | 6.13<br>6.00 | 13.75<br>13.72 | 3,365<br>3,200<br>1,620 |
| 44 | " | 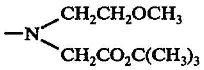 | ½ $H_2SO_3$ | | 1 | " | 51.47<br>51.20 | 6.65<br>6.35 | 11.54<br>11.24 | 3,370<br>3,200<br>1,740<br>1,370 |
| 45 | " | 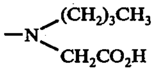 | — | | 1 | " | 54.43<br>54.28 | 6.55<br>6.31 | 13.80<br>13.70 | 3,375<br>3,200<br>1,622 |
| 46 | " | 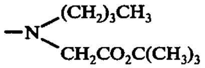 | ½ $H_2SO_3$ | | 1 | " | 53.63<br>53.53 | 7.00<br>7.08 | 11.58<br>11.40 | 3,380<br>3,200<br>1,740<br>1,370 |
| 47 | " | 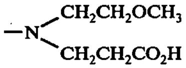 | — | | 1 | " | 52.76<br>52.47 | 6.35<br>6.01 | 13.38<br>13.09 | 3,375<br>3,180<br>1,620 |

Table 2-continued

Compound 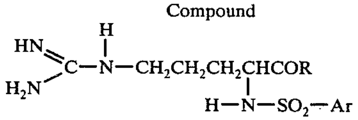 (I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 48 | " | 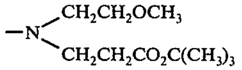 | ½ $H_2SO_3$ | | 1 | " | 52.24<br>52.00 | 6.82<br>6.55 | 11.28<br>11.00 | 3,380<br>3,200<br>1,740<br>1,368 |
| 49 | 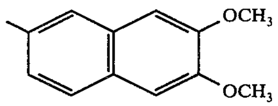 | 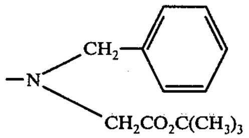 | 0.5 $H_2SO_3$ | | 1 | 189-191 (dec.) | 55.68<br>55.36 | 6.33<br>6.35 | 10.47<br>10.45 | 3,360<br>3,160<br>1,730 |
| 50 | " | 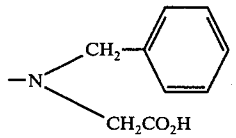 | — | 2.5 | 1 | powder | 56.73<br>56.43 | 5.82<br>5.80 | 12.25<br>12.19 | 3,370<br>3,200<br>1,615 |
| 51 | " | 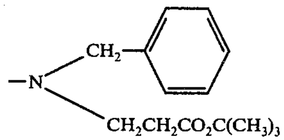 | 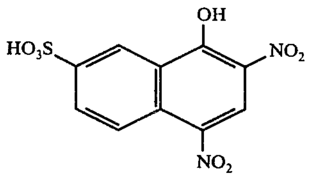 | | 1 | 132-135 (dec.) | 52.78<br>52.61 | 5.17<br>5.15 | 10.26<br>10.23 | 3,360<br>3,180<br>1,720 |
| 52 | " | 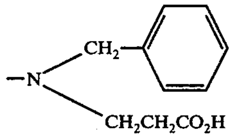 | — | 10 | 1 | powder | 57.42<br>57.19 | 6.02<br>6.10 | 11.96<br>11.73 | 3,360<br>3,160<br>1,620 |
| 53 | " | 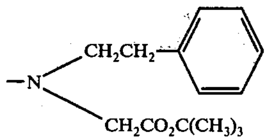 | 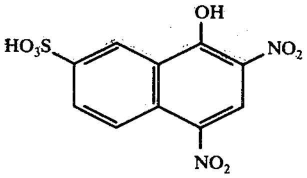 | | 1 | 157-158 (dec.) | 52.78<br>52.63 | 5.17<br>5.14 | 10.26<br>10.09 | 3,380<br>3,220<br>1,750 |

Table 2-continued

Compound

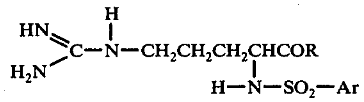 (I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 54 | " | 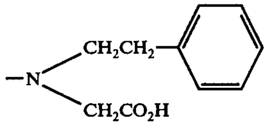 | — | 3.0 | 1 | powder | 57.42<br>57.09 | 6.02<br>6.06 | 11.96<br>11.74 | 3,360<br>3,200<br>1,590 |
| 55 | " | 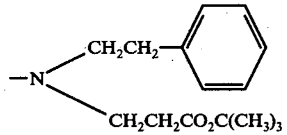 | 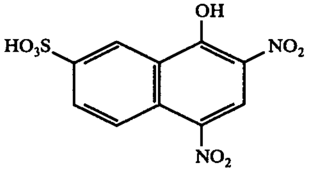 | | 1 | 155-157 (dec.) | 53.25<br>53.13 | 5.30<br>5.21 | 10.11<br>10.03 | 3,380<br>3,180<br>1,720 |
| 56 | " | 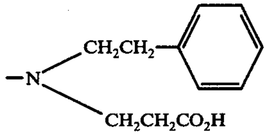 | — | 50 | 1 | powder | 58.08<br>57.93 | 6.22<br>6.04 | 11.68<br>11.54 | 3,200-3,380 (broad)<br>1,620 |
| 57 | 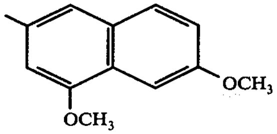 | 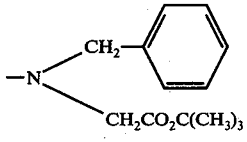 | 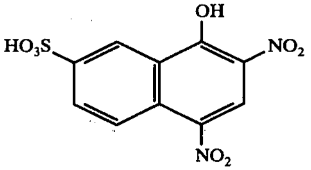 | | 1 | 153-156 (dec.) | 52.28<br>52.14 | 5.03<br>4.98 | 10.41<br>10.36 | 3,400<br>1,080<br>1,740 |
| 58 | " | 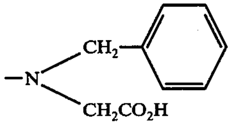 | — | 6.5 | 1 | powder | 56.73<br>56.58 | 5.82<br>5.73 | 12.25<br>12.14 | 3,000-3,400 (broad)<br>1,600 |

Table 2-continued
| Sample No. | Ar | Compound 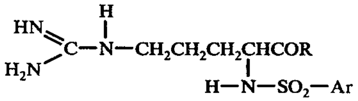 (I) R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) (cm$^{-1}$) |
|---|---|---|---|---|---|---|---|---|---|---|
| 59 | 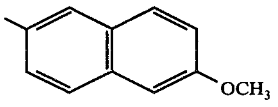 | 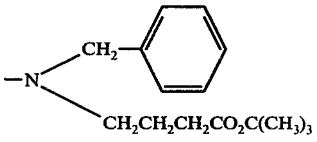 | 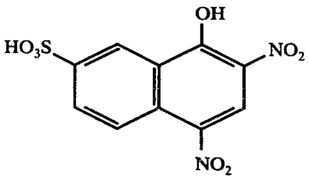 | | 1 | 144–148 (dec.) | 53.67<br>53.69 | 5.26<br>5.24 | 10.43<br>10.39 | 3,360<br>3,200<br>1,720 |
| 60 | " | 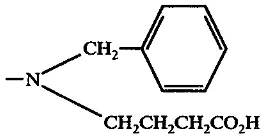 | — | 50 | 1 | powder | 59.04<br>59.14 | 6.19<br>6.15 | 12.30<br>12.28 | 3,040–3,360 (broad)<br>1,610 |
| 61 | " | 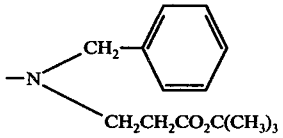 | 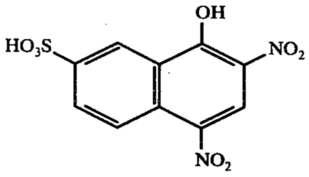 | | 1 | 155–158 (dec.) | 53.19<br>54.97 | 5.12<br>5.06 | 10.59<br>10.48 | 3,400<br>3,200<br>1,730 |
| 62 | " | 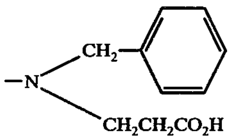 | — | 15 | 1 | powder | 58.37<br>58.19 | 6.00<br>5.98 | 12.61<br>12.49 | 3,300 (broad)<br>1,640 |
| 63 | 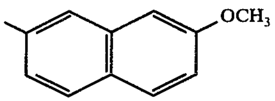 | 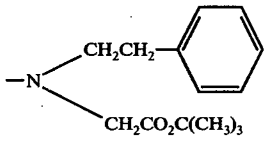 | 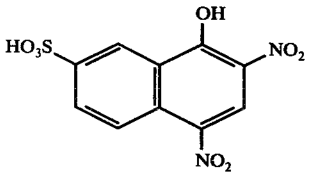 | | 1 | 147–150 (dec.) | 59.19<br>59.23 | 5.12<br>5.07 | 10.59<br>10.54 | 3,400<br>3,230<br>1,750 |

Table 2-continued
Compound
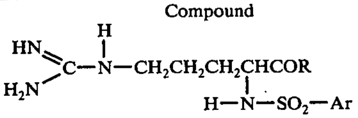 (I)
| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 64 | " | 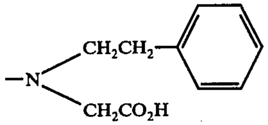 | — | 20 | 1 | powder | 58.37 | 6.00 | 12.61 | 3,200 (broad) |
| | | | | | | | 58.21 | 5.93 | 12.46 | 1,620 |
| 65 | 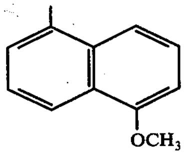 | 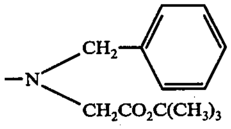 | — | | 1 | " | 60.29 | 6.58 | 11.72 | 3,365<br>3,170<br>1,730 |
| | | | | | | | 60.21 | 6.56 | 11.64 | |
| 66 | " | 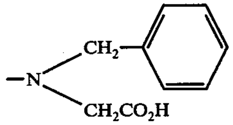 | — | 2.0 | 1 | " | 57.66 | 5.77 | 12.93 | 3,360<br>3,160<br>1,610 |
| | | | | | | | 57.48 | 5.74 | 12.84 | |
| 67 | 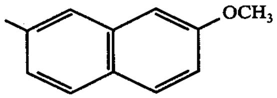 | 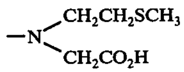 | — | 1 | 1 | " | 50.25 | 5.95 | 13.32 | 3,350<br>1,620<br>1,380<br>1,150 |
| | | | | | | | 50.45 | 6.01 | 13.15 | |
| 68 | 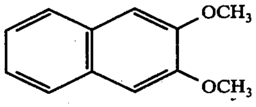 | 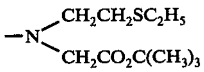 | $\frac{1}{2}$ $H_2SO_3$ | | 1 | " | 50.43 | 6.65 | 10.50 | 3,350<br>1,745<br>1,650<br>1,360 |
| | | | | | | | 50.57 | 6.58 | 10.71 | |
| 69 | " | 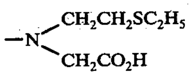 | — | 5 | 1 | 171-2 | 50.60 | 6.19 | 12.29 | 3,400<br>1,635<br>1,260<br>1,160 |
| | | | | | | | 50.51 | 6.30 | 12.40 | |
| 70 | " | 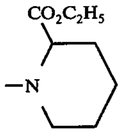 | — | | 3 | powder | 55.40 | 6.62 | 12.43 | 3,220<br>1,750<br>1,640 |
| | | | | | | | 55.65 | 6.81 | 12.19 | |

Table 2-continued

Compound

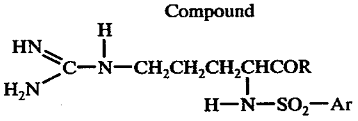 (I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 71 | " | 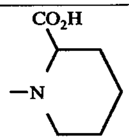 | — | 5 | 2 | " | 53.82<br>53.66 | 6.21<br>5.96 | 13.08<br>12.81 | 3,350<br>1,625<br>1,155 |
| 72 | 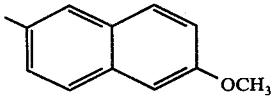 | 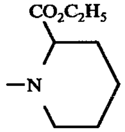 | 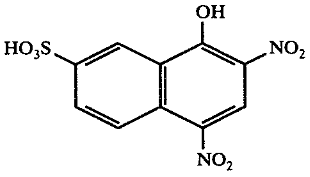 | | 2 | 192–193 | 49.58<br>49.24 | 4.87<br>4.70 | 11.56<br>11.85 | 3,210<br>1,747<br>1,638 |
| 73 | " | 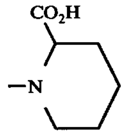 | — | 3 | 2 | powder | 54.64<br>56.88 | 6.18<br>6.31 | 13.85<br>13.83 | 3,200 (broad)<br>1,620<br>1,150 |
| 74 | 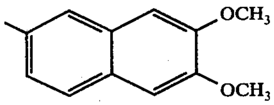 | 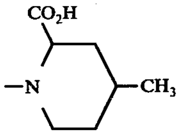 | — | 0.4 | 2 | " | 54.63<br>54.50 | 6.42<br>6.09 | 12.74<br>12.81 | 3,370<br>1,625<br>1,158 |
| 75 | 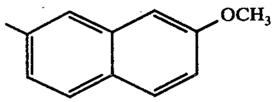 | 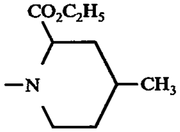 | 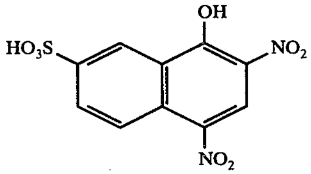 | | 2 | 188–190 | 50.17<br>50.01 | 5.03<br>4.78 | 11.38<br>11.56 | 3,200<br>1,740<br>1,635 |
| 76 | " | 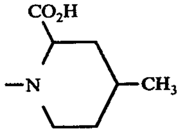 | — | 0.15 | 2 | powder | 55.47<br>55.49 | 6.40<br>6.33 | 13.98<br>13.51 | 3,250 (broad)<br>1,625 |

Table 2-continued
| Sample No. | Compound 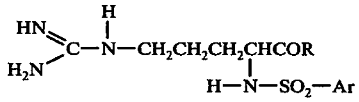 (I) Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 77 | 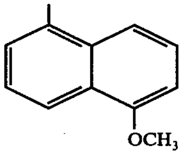 | 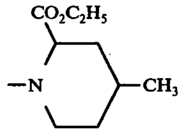 | — | | 2 | " | 57.02<br>56.81 | 6.81<br>6.91 | 12.79<br>12.78 | 3,200<br>1,740<br>1,635 |
| 78 | " | 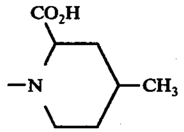 | — | | 2 | powder | 55.47<br>55.31 | 6.40<br>6.68 | 13.48<br>13.21 | 3,350<br>1,620<br>1,150 |
| 79 | 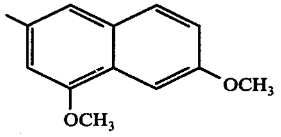 | 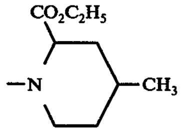 | 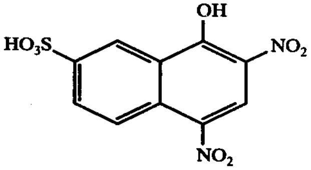 | | 2 | 222-3 | 49.82<br>49.57 | 5.09<br>4.88 | 11.99<br>11.68 | 3,200<br>1,745<br>1,630 |
| 80 | " | 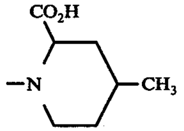 | — | 0.35 | 2 | powder | 54.63<br>54.55 | 6.42<br>6.42 | 12.74<br>12.58 | 3,350 (broad)<br>1,620<br>1,150 |
| 81 | 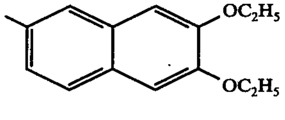 | 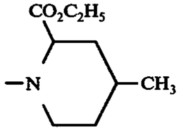 | 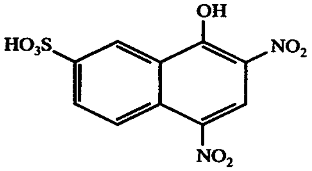 | | 2 | 154-6 | 50.92<br>51.28 | 5.37<br>5.21 | 10.66<br>10.59 | 3,400<br>1,735<br>1,635 |

Table 2-continued
| Compound 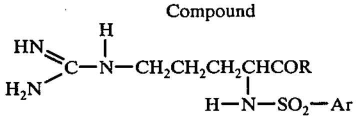 (I)<br>Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 82 | " | 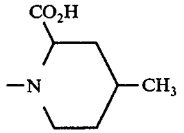 | — | | 2 | powder | 56.13 | 6.80 | 12.12 | 3,300 (broad)<br>1,610 |
| | | | | | | | 56.11 | 6.85 | 11.95 | 1,255 |
| 83 | 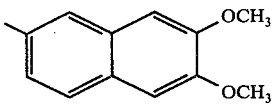 | 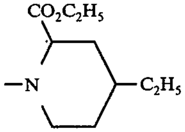 | 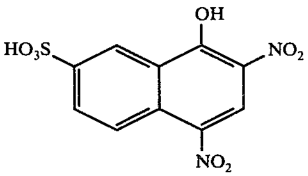 | | 2 | 179-180 | 50.38 | 5.23 | 10.82 | 3,380<br>1,735 |
| | | | | | | | 50.34 | 5.18 | 11.05 | 1,635 |
| 84 | " | 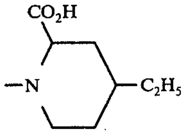 | — | | 2 | powder | 55.40 | 6.62 | 12.43 | 3,360<br>1,620 |
| | | | | | | | 55.71 | 6.48 | 12.53 | 1,150 |
| 85 | 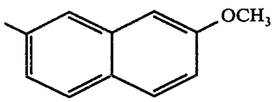 | 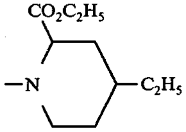 | 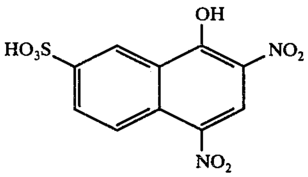 | | 2 | 125 (soften) | 50.73 | 5.18 | 11.19 | 3,380<br>1,735 |
| | | | | | | | 50.58 | 5.11 | 10.93 | 1,638 |
| 86 | " | 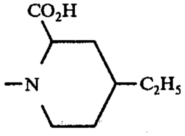 | — | | 2 | powder | 56.26 | 6.61 | 13.12 | 3,360<br>1,620 |
| | | | | | | | 56.41 | 6.48 | 13.27 | 1,158 |
| 87 | 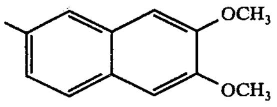 | 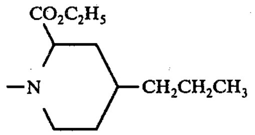 | — | | 2 | " | 57.50 | 7.15 | 11.56 | 3,330<br>2,960 |
| | | | | | | | 57.56 | 7.08 | 11.71 | 1,740<br>1,640 |

Table 2-continued
Compound
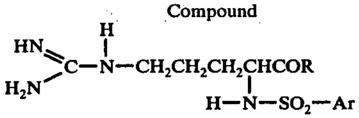 (I)
| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 88 | " | 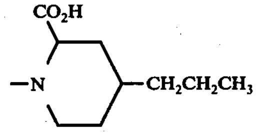 | — | 0.5 | 2 | " | 56.13<br>56.11 | 6.80<br>6.81 | 12.12<br>11.96 | 3,400<br>1,620 |
| 89 | " | 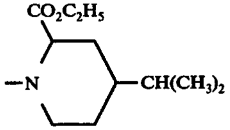 | — | | 2 | " | 57.50<br>57.15 | 7.15<br>7.21 | 11.56<br>11.62 | 3,360<br>2,960<br>1,735 |
| 90 | " | 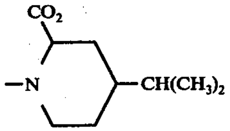 | — | | 2 | " | 56.13<br>56.21 | 6.80<br>6.81 | 12.12<br>12.03 | 3,400<br>1,620<br>1,150 |
| 91 | " | 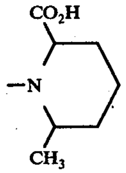 | — | | 2 | " | 54.63<br>54.54 | 6.42<br>6.40 | 12.74<br>12.68 | 3,350<br>1,620<br>1,150 |
| 92 | " | 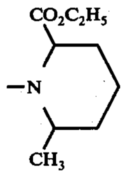 | — | | 2 | powder | 56.13<br>56.08 | 6.80<br>6.91 | 12.12<br>12.08 | 3,250<br>1,740<br>1,640 |
| 93 | 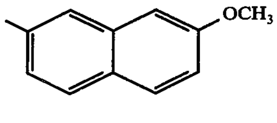 | 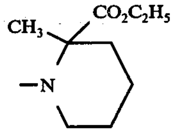 | — | | 2 | " | 57.02<br>56.86 | 6.81<br>6.83 | 12.79<br>12.68 | 3,230<br>1,740<br>1,650 |

Table 2-continued

Compound

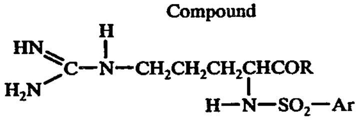 (I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 94 | " | 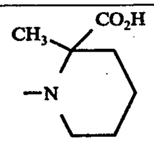 | — | | 2 | " | 54.63<br>54.59 | 6.42<br>6.38 | 12.74<br>12.68 | 3,250<br>1,620<br>1,160 |
| 95 | 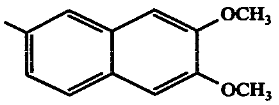 | 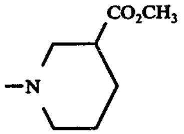 | 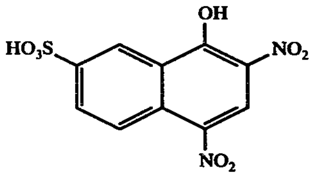 | | 2 | 161-163 | 48.97<br>49.05 | 4.71<br>4.73 | 11.76<br>11.58 | 3,340<br>1,738<br>1,635 |
| 96 | " | 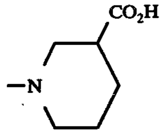 | — | | 2 | powder | 53.82<br>53.68 | 6.21<br>6.08 | 13.08<br>12.85 | 3,370<br>1,635<br>1,255<br>1,155 |
| 97 | 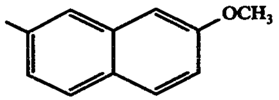 | 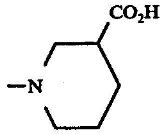 | — | | 2 | " | 54.64<br>54.58 | 6.18<br>6.09 | 13.85<br>13.93 | 3,370<br>1,640<br>1,260<br>1,155 |
| 98 | 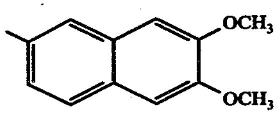 | 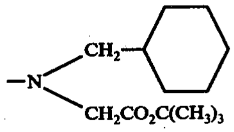 | 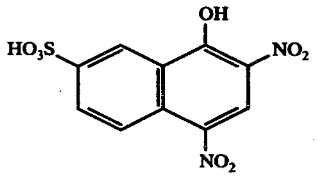 | | 1 | 165-168 (dec.) | 51.94<br>51.50 | 5.64<br>5.41 | 10.34<br>10.10 | 3,390<br>3,220<br>1,740 |
| 99 | " | 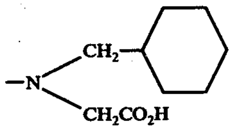 | — | | 1 | powder | 56.13<br>56.00 | 6.81<br>6.73 | 12.12<br>12.01 | 3,350 (broad)<br>1,640 |

Table 2-continued

| Sample No. | Compound 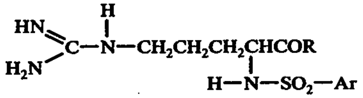 (I) Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) (cm⁻¹) |
|---|---|---|---|---|---|---|---|---|---|---|
| 100 | " | 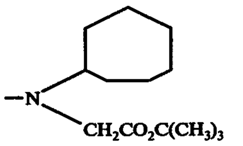 | 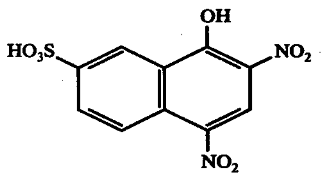 | | 1 | 178–181 (dec.) | 51.94<br>52.24 | 5.64<br>5.60 | 10.34<br>10.28 | 3,400<br>3,200<br>1,735 |
| 101 | " | 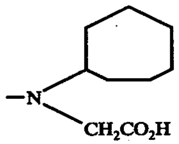 | — | | 1 | powder | 56.13<br>56.28 | 6.81<br>6.59 | 12.12<br>12.31 | 3,350 (broad)<br>1,640 |
| 102 | 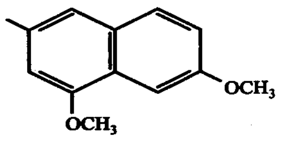 | 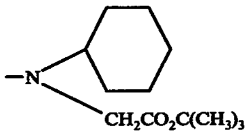 | 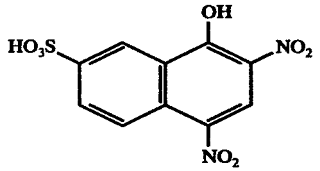 | | 1 | 162–165 (dec.) | 51.43<br>51.28 | 5.50<br>5.21 | 10.50<br>10.21 | 3,370<br>3,200<br>1,730 |
| 103 | " | 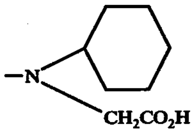 | — | | 1 | powder | 55.40<br>55.28 | 6.62<br>6.32 | 12.43<br>12.03 | 3,300 (broad)<br>1,610 (broad) |
| 104 | 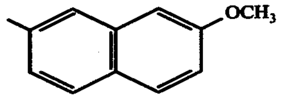 | 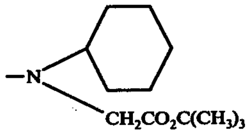 | 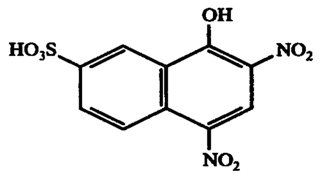 | | 1 | 158–160 (dec.) | 52.75<br>52.56 | 5.56<br>5.43 | 11.04<br>10.97 | 3,405<br>3,220<br>1,740 |

Table 2-continued
| Sample No. | Ar | Compound 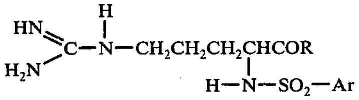 (I) R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 105 | " | 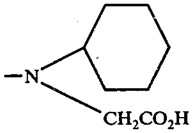 | — | | 1 | powder | 56.26 | 6.61 | 13.13 | 3,320 (broad) |
| | | | | | | | 56.01 | 6.49 | 13.21 | 1,640 |
| 106 | " | 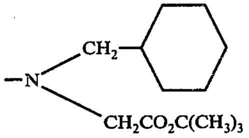 | 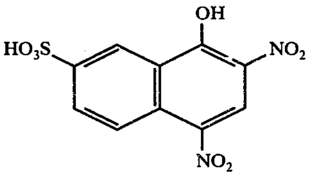 | | 1 | 160-163 (dec.) | 52.33 | 5.60 | 10.68 | 3,400 3,210 1,730 |
| | | | | | | | 52.03 | 5.30 | 10.28 | |
| 107 | " | 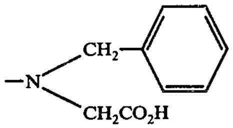 | — | | 1 | powder | 57.02 | 6.81 | 12.79 | 3,350 (broad) |
| | | | | | | | 57.39 | 6.21 | 12.38 | 1,620 |
| 108 | 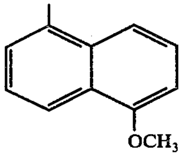 | 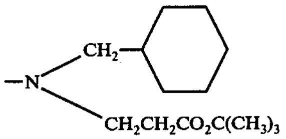 | 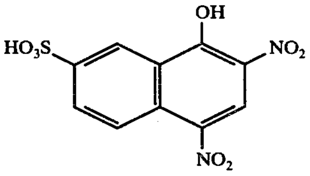 | | 1 | 152-155 (dec.) | 52.83 | 5.73 | 10.52 | 3,390 3,205 1,730 |
| | | | | | | | 52.53 | 5.72 | 10.29 | |
| 109 | " | 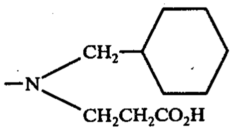 | — | | 1 | powder | 57.73 | 7.00 | 12.47 | 3,370 |
| | | | | | | | 57.51 | 7.23 | 12.28 | 1,630 |

Table 2-continued

Compound

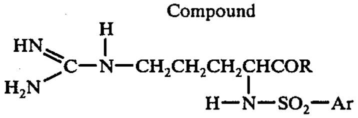

(I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) (cm⁻¹) |
|---|---|---|---|---|---|---|---|---|---|---|
| 110 | 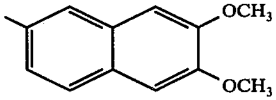 | 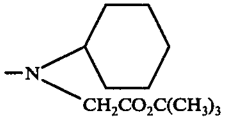 | 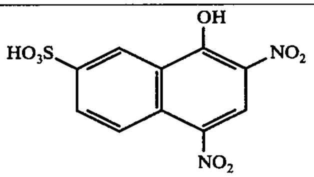 | | 1 | 170-172 (dec.) | 51.43<br>51.09 | 5.50<br>5.45 | 10.50<br>10.28 | 3,380<br>3,220<br>1,740 |
| 111 | " | 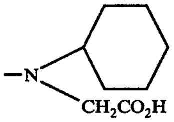 | — | 5 | 1 | powder | 55.40<br>55.30 | 6.62<br>6.28 | 12.43<br>12.11 | 3,400-3,200<br>(broad)<br>1,600 |
| 112 | " | 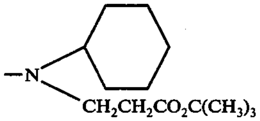 | 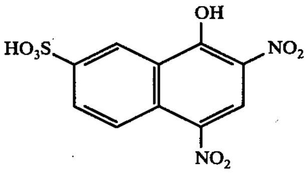 | | 1 | 155-158 (dec.) | 51.94<br>52.29 | 5.64<br>5.63 | 10.34<br>10.00 | 3,380<br>3,200<br>1,730 |
| 113 | 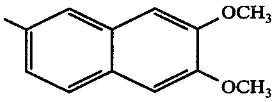 | 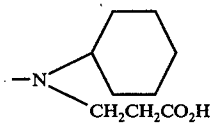 | — | | 1 | powder | 56.13<br>56.40 | 6.81<br>6.61 | 12.12<br>12.00 | 3,200-3,400<br>(broad)<br>1,600 |
| 114 | " | 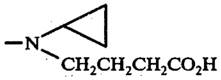 | — | | 1 | " | 54.63<br>54.40 | 6.42<br>6.30 | 12.74<br>12.50 | 3,200-3,400<br>(broad)<br>1,600 |
| 115 | " | 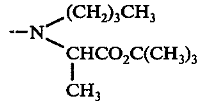 | 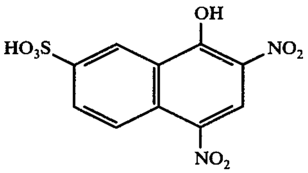 | | 1 | 165-170 (dec.) | 50.81<br>50.68 | 5.58<br>5.43 | 10.64<br>10.31 | 3,380<br>3,200<br>1,740 |

Table 2-continued

Compound 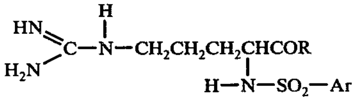 (I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 116 | " | 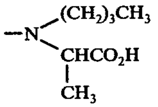 | — | | 1 | powder | 54.43<br>54.70 | 6.76<br>6.71 | 12.70<br>12.35 | 3,400<br>1,590 |
| 117 | " | 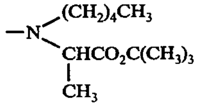 | 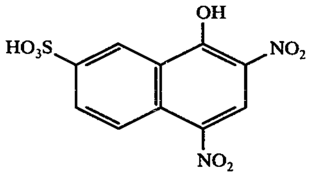 | | 1 | 164–166 | 51.33<br>51.60 | 5.71<br>5.38 | 10.48<br>10.25 | 3,360<br>3,200<br>1,735 |
| 118 | " | 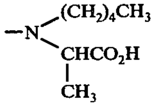 | — | 2.0 | 1 | powder | 55.21<br>55.00 | 6.95<br>6.30 | 12.38<br>12.40 | 3,400–3,200<br>(broad)<br>1,570 |
| 119 | " | 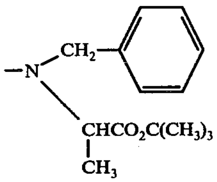 | 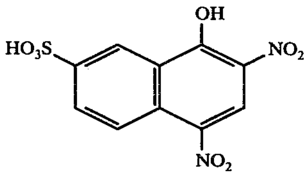 | | 1 | 168–172 | 52.77<br>52.54 | 5.17<br>4.98 | 10.26<br>10.21 | 3,380<br>3,180<br>1,740 |
| 120 | 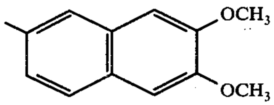 | 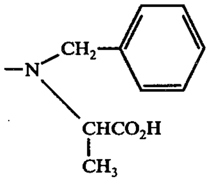 | — | 2.5 | 1 | powder | 57.42<br>57.35 | 6.02<br>5.84 | 11.96<br>12.00 | 3,350–3,160<br>(broad)<br>1,600 |

Table 2-continued
Compound 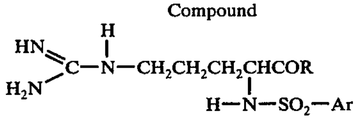 (I)
| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 121 | " | 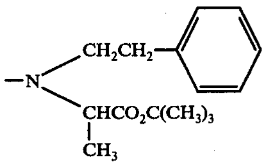 | 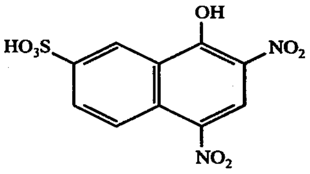 | | 1 | 130–135 | 53.25<br>53.08 | 5.30<br>5.29 | 10.11<br>10.29 | 3,400<br>3,200<br>1,730 |
| 122 | " | 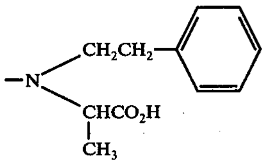 | — | 1.5 | 1 | powder | 58.08<br>57.84 | 6.22<br>6.13 | 11.68<br>11.46 | 3,360<br>3,160<br>1,600 |
| 123 | " | 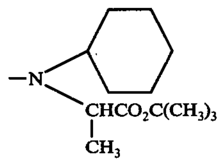 | 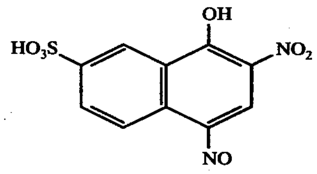 | | 1 | 158–163 (dec.) | 51.95<br>51.80 | 5.64<br>5.38 | 10.34<br>10.30 | 3,360<br>3,200<br>1,740 |
| 124 | " | 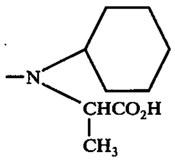 | — | | 1 | powder | 56.14<br>55.98 | 6.81<br>6.79 | 12.13<br>12.35 | 3,380–3,200 (broad)<br>1,625 |
| 125 | 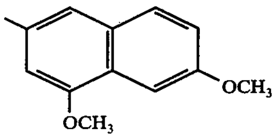 | 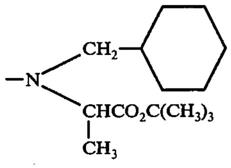 | 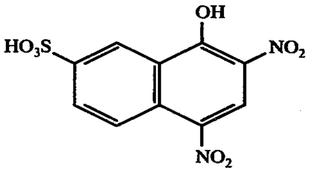 | | 1 | 160–163 (dec.) | 52.44<br>52.39 | 5.76<br>5.58 | 10.19<br>10.00 | 3,400<br>3,200<br>1,740 |

Table 2-continued
Compound
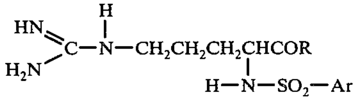 (I)
| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 126 | " | 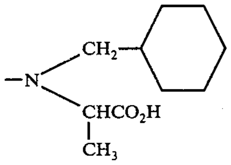 | — | 4.5 | 1 | powder | 56.84<br>56.72 | 6.99<br>6.80 | 11.84<br>11.76 | 3,380-3,250 (broad)<br>1,595 |
| 127 | 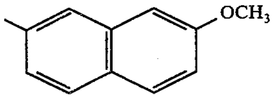 | 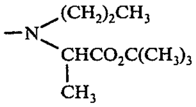 | 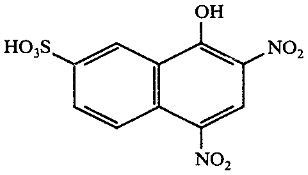 | | 1 | 160-165 (dec.) | 50.62<br>50.39 | 5.40<br>5.28 | 11.17<br>11.15 | 3,400<br>3,210<br>1,740 |
| 128 | " | 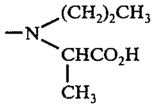 | — | | 1 | powder | 54.43<br>54.27 | 6.55<br>6.28 | 13.80<br>13.59 | 3,280<br>1,590 |
| 129 | 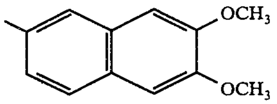 | 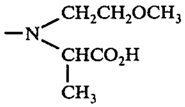 | — | 5 | 1 | " | 52.07<br>51.89 | 6.37<br>6.39 | 12.65<br>12.51 | 3,360<br>3,200<br>1,600 |
| 130 | 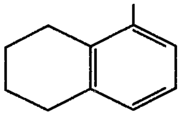 | 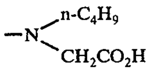 | — | 20 | 5 | 210-213 | 54.86<br>54.72 | 7.33<br>7.21 | 14.54<br>14.27 | 3,350<br>1,630 |
| 131 | 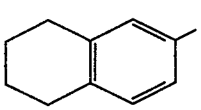 | 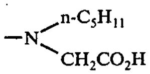 | — | | 5 | 120-130 | 55.73<br>55.82 | 7.52<br>7.50 | 14.13<br>14.01 | 3,350<br>1,630 |

Table 2-continued
| Sample No. | Compound (I) 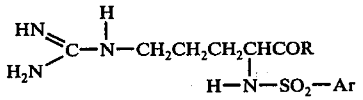 Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 132 | 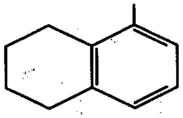 | 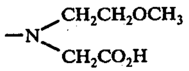 | — | 10 | 5 | 108–110 | 52.15 | 6.88 | 14.48 | 3,300 (broad) |
| | | | | | | | 52.21 | 6.71 | 14.52 | 1,630 |
| 133 | 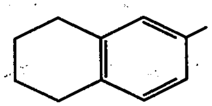 | 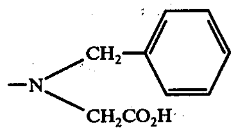 | — | 30 | 5 | powder | 58.23 | 6.45 | 13.58 | 3,300 (broad) |
| | | | | | | | 58.01 | 6.35 | 13.46 | 1,635 |
| 134 | 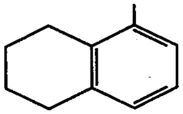 | 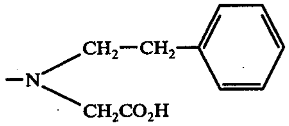 | — | | 5 | powder | 58.96 | 6.66 | 13.22 | 3,200 (broad) |
| | | | | | | | 58.91 | 6.79 | 13.15 | 1,635 |
| 135 | 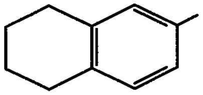 | 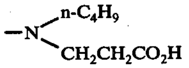 | — | | 5 | " | 55.73 | 7.52 | 14.13 | 3,300 (broad) |
| | | | | | | | 55.81 | 7.40 | 14.10 | 1,630 |
| 136 | " | 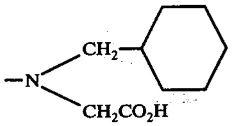 | — | | 5 | 170–173 | 57.56 | 7.54 | 13.43 | 3,335 |
| | | | | | | | 57.41 | 7.39 | 13.50 | 1,630 |
| 137 | 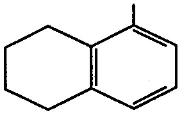 | 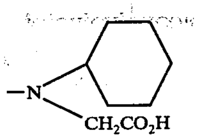 | — | | 5 | powder | 56.78 | 7.35 | 13.80 | 3,200 (broad) |
| | | | | | | | 56.85 | 7.29 | 13.71 | 1,630 |

Table 2-continued
Compound
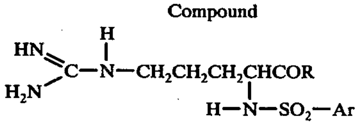 (I)
| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) (cm$^{-1}$) |
|---|---|---|---|---|---|---|---|---|---|---|
| 138 | 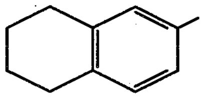 | 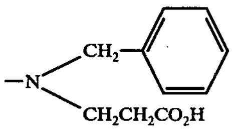 | — | | 5 | " | 58.96 | 6.66 | 13.22 | 3,300 (broad) |
| | | | | | | | 58.79 | 6.51 | 13.19 | 1,630 |
| 139 | 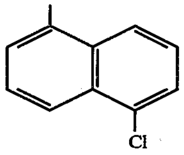 | 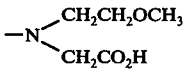 | — | | 5 | 142–145 | 49.07 | 5.49 | 13.63 | 3,150 |
| | | | | | | | 48.90 | 5.38 | 13.42 | 1,620 |
| 140 | 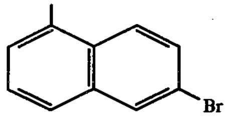 | 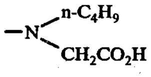 | — | | 5 | powder | 47.47 | 5.43 | 12.58 | 3,150 |
| | | | | | | | 47.29 | 5.31 | 12.39 | 1,630 |
| 141 | 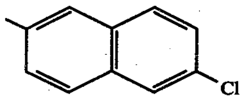 | 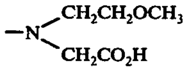 | — | | 5 | powder | 49.07 | 5.49 | 13.63 | 3,150 |
| | | | | | | | 49.12 | 5.28 | 13.59 | 1,630 |
| 142 | 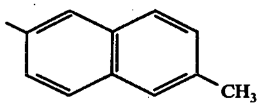 | 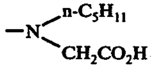 | — | | 5 | 123–130 | 57.01 | 6.98 | 13.85 | 3,300 |
| | | | | | | | 56.88 | 6.71 | 13.65 | 1,635 |
| 143 | 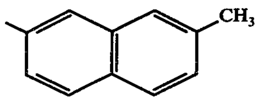 | 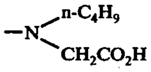 | — | 0.3 | 5 | powder | 56.19 | 6.77 | 14.25 | 3,300 3,150 |
| | | | | | | | 56.00 | 6.50 | 14.00 | 1,630 |
| 144 | " | 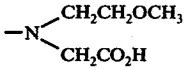 | — | 0.2 | 5 | " | 53.53 | 6.33 | 14.19 | 3,300 (broad) |
| | | | | | | | 53.24 | 6.19 | 13.99 | 1,630 |

Table 2-continued

| Sample No. | Ar | Compound 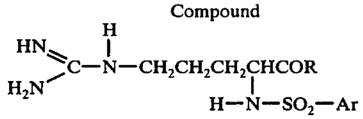 (I)<br>R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 145 | " | 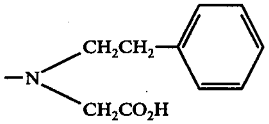 | — | | 5 | " | 60.09<br>57.79 | 6.16<br>6.02 | 12.93<br>12.61 | 3,300 (broad)<br>1,630 |
| 146 | " | 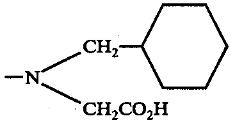 | — | 14 | 5 | " | 58.73<br>58.66 | 7.01<br>6.90 | 13.17<br>12.91 | 3,380<br>1,635 |
| 147 | 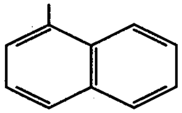 | 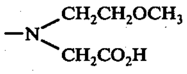 | — | | 5 | 147-150 | 52.59<br>52.31 | 6.10<br>6.01 | 14.61<br>14.33 | 3,380<br>1,640 |
| 148 | 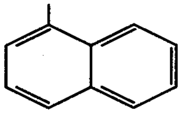 | 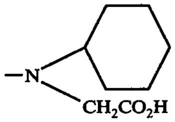 | — | | 5 | powder | 57.23<br>56.98 | 6.61<br>6.33 | 13.91<br>13.81 | 3,300 (broad)<br>1,630 |
| 149 | 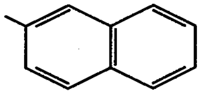 | 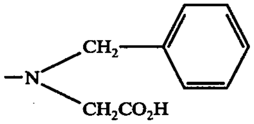 | — | | 5 | " | 58.69<br>58.79 | 5.71<br>5.55 | 13.69<br>13.39 | 3,300 (broad)<br>3,150<br>1,630 |
| 150 | " | 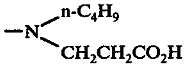 | — | | 5 | " | 56.19<br>55.95 | 6.77<br>6.58 | 14.25<br>13.97 | 3,190 (broad)<br>1,620 |
| 151 | 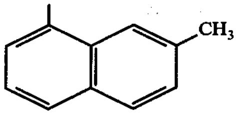 | 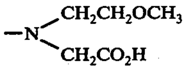 | — | 20 | 5 | 130-135 | 53.53<br>53.28 | 6.33<br>6.19 | 14.19<br>13.97 | 3,350<br>1,640 |

Table 2-continued

| Sample No. | Compound 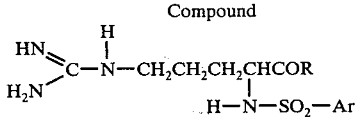 (I) Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 152 | 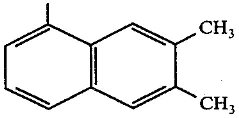 | 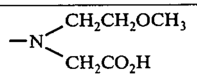 | — | 10 | 5 | 152–157 | 54.42<br>54.28 | 6.55<br>6.32 | 13.80<br>13.59 | 3,350<br>1,635 |
| 153 | 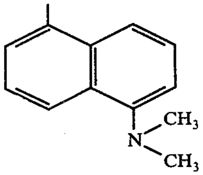 | 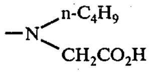 | — | 4 | 5 | powder | 55.36<br>55.10 | 6.97<br>6.76 | 16.14<br>16.07 | 3,380<br>1,630 |
| 154 | " | 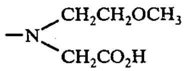 | — | | 5 | " | 52.86<br>52.71 | 6.56<br>6.29 | 16.08<br>16.07 | |
| 155 | 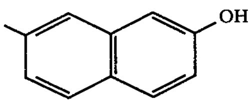 | 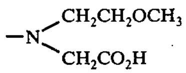 | — | | 5 | powder | 50.90<br>50.81 | 5.90<br>5.70 | 14.13<br>13.89 | 3,180 (broad)<br>1,630 |
| 156 | 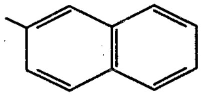 | 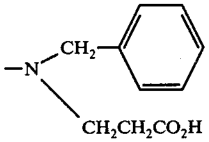 | — | | 5 | " | 59.41<br>59.22 | 5.95<br>5.73 | 13.33<br>13.28 | 3,170 (broad)<br>1,620 |
| 157 | " | 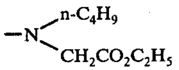 | HCl | | 6 | " | 53.17<br>52.89 | 6.69<br>6.52 | 12.92<br>12.74 | |
| 158 | " | 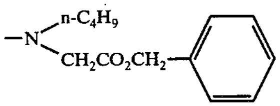 | HCl | | 6 | " | 57.66<br>57.31 | 6.34<br>6.14 | 11.59<br>11.16 | |

Table 2-continued

Compound

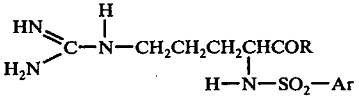

(I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) (cm$^{-1}$) |
|---|---|---|---|---|---|---|---|---|---|---|
| 159 | " | 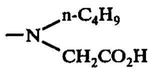 | — | | 5 | " | 55.33<br>55.26 | 6.54<br>6.62 | 14.67<br>14.58 | 3,200 (broad)<br>1,630 |
| 160 | 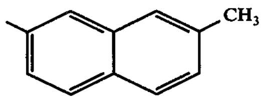 | 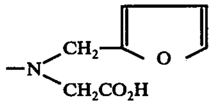 | — | 0.25 | 1 | " | 55.47<br>55.75 | 6.40<br>6.19 | 13.48<br>13.26 | 3,350 (broad)<br>1,630<br>1,380 |
| 161 | " | 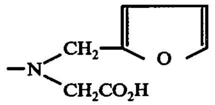 | — | 0.2 | 5 | " | 55.05<br>55.28 | 7.12<br>7.00 | 13.38<br>13.12 | 3,200 (broad)<br>1,635<br>1,380 |
| 162 | 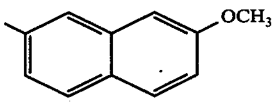 | 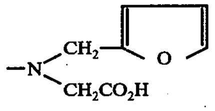 | — | 0.2 | 1 | powder | 54.22<br>53.98 | 5.50<br>5.55 | 13.18<br>13.24 | 3,320 (broad)<br>1,630<br>1,380 |
| 163 | " | 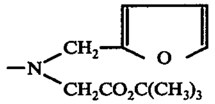 | — | | 1 | " | 57.22<br>57.23 | 6.35<br>6.36 | 11.92<br>12.08 | 3,400 (broad)<br>1,740<br>1,620 |
| 164 | " | 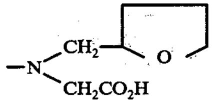 | — | 0.15 | 1 | " | 53.82<br>53.78 | 6.21<br>6.19 | 13.08<br>12.86 | 3,360 (broad)<br>1,625<br>1,380 |
| 165 | " | 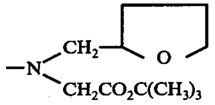 | — | | 1 | " | 56.83<br>56.95 | 6.98<br>6.83 | 11.84<br>11.98 | 3,400 (broad)<br>1,735<br>1,630 |

Table 2-continued

| Sample No. | Compound 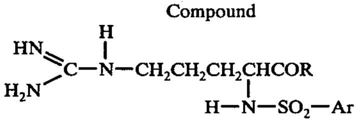 (I) Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 166 | 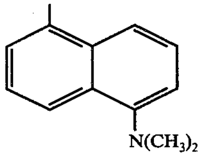 | 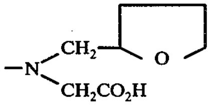 | $CH_3CO_2H$ | | 5 | " | 53.28<br>53.13 | 6.62<br>6.82 | 13.81<br>13.71 | 3,320 (broad)<br>1,630<br>1,140 |
| 167 | 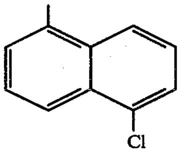 | 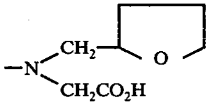 | — | | 5 | " | 51.15<br>50.86 | 5.60<br>5.66 | 12.97<br>12.87 | 3,320 (broad)<br>1,630<br>1,380 |
| 168 | 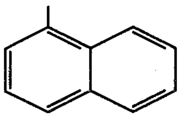 | 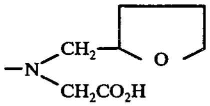 | — | | 5 | " | 54.64<br>53.36 | 6.18<br>6.00 | 13.85<br>13.58 | 3,350 (broad)<br>1,640<br>1,390 |
| 169 | 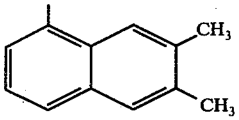 | 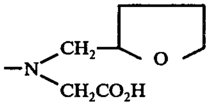 | — | | 5 | " | 56.27<br>55.98 | 6.61<br>6.78 | 13.12<br>13.24 | 3,350 (broad)<br>1,630<br>1,380<br>1,140 |
| 170 | 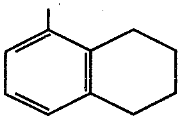 | 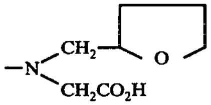 | — | | 5 | " | 54.21<br>54.36 | 6.92<br>6.93 | 13.74<br>13.76 | 3,300 (broad)<br>1,625<br>1,380<br>1,160 |
| 171 | 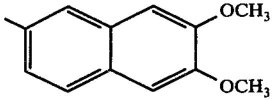 | 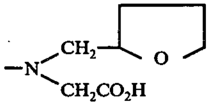 | — | | 1, 2 | " | 53.08<br>52.86 | 6.24<br>6.33 | 12.38<br>12.41 | 3,300 (broad)<br>1,640<br>1,160 |

Table 2-continued

| Sample No. | Compound<br>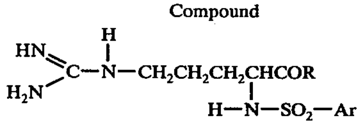 (I)<br>Ar | R | Addition moiety | Concentration required to prolong the coagulation time by a factor of two (μM) | Preparation process (Ex. No.) | m.p. (° C) | Elementary analysis Upper: Calculated (%) Lower: Found (%)<br>C | H | N | I.R. (KBr) (cm⁻¹) |
|---|---|---|---|---|---|---|---|---|---|---|
| 172 | " | 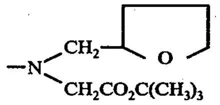 | — | | 1 | " | 56.02<br>55.83 | 6.97<br>6.88 | 11.27<br>11.28 | 3,400 (broad)<br>1,745<br>1,620 |
| 173 | 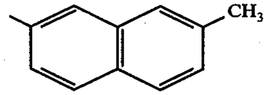 | 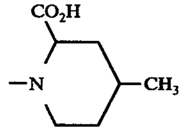 | — | 0.2 | 3 | " | 57.23<br>56.89 | 6.61<br>6.50 | 13.91<br>13.70 | 3,390 (broad)<br>1,625 |
| 174 | " | 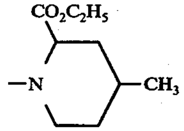 | $CH_3COOH$ | | 3 | " | 56.83<br>56.72 | 6.98<br>6.81 | 11.84<br>11.56 | 3,400 (broad)<br>1,735<br>1,640 |
| 175 | " | 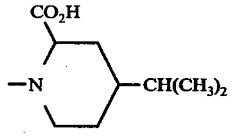 | — | 0.1 | 2 | " | 58.73<br>58.52 | 7.01<br>6.77 | 13.17<br>13.00 | 3,380 (broad)<br>1,620 |
| 176 | " | 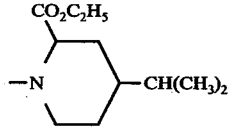 | ½ $H_2SO_3$ | | 2 | " | 55.98<br>55.69 | 7.05<br>7.21 | 11.66<br>11.38 | 3,400 (broad)<br>1,730<br>1,635 |
| 177 | 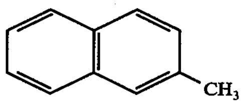 | 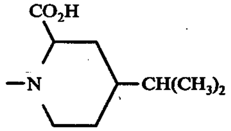 | — | | 3 | " | 58.73<br>58.81 | 7.02<br>7.03 | 13.17<br>13.17 | 3,300 (broad)<br>1,615<br>1,380 |

Table 2-continued

| Sample No. | Ar | Compound 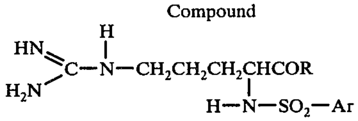 (I) R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 178 | " | 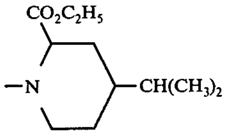 | $CH_3COOH$ | | 3 | " | 58.13<br>57.98 | 7.32<br>7.56 | 11.30<br>11.28 | 3,380 (broad)<br>1,730<br>1,630 |
| 179 | 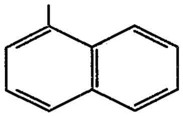 | 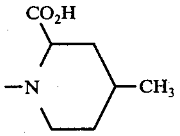 | — | 1 | 3 | " | 56.42<br>56.38 | 6.38<br>6.52 | 14.31<br>14.53 | 3,350 (broad)<br>1,620<br>1,160 |
| 180 | " | 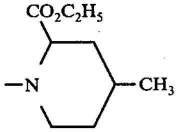 | $CH_3COOH$ | | 3 | " | 56.13<br>56.08 | 6.80<br>6.83 | 12.12<br>12.12 | 3,400 (broad)<br>1,740<br>1,630 |
| 181 | 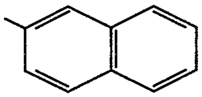 | 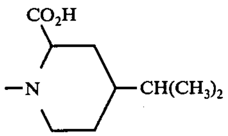 | — | 0.5 | 3 | " | 58.00<br>57.83 | 6.82<br>6.77 | 13.53<br>13.63 | 3,350 (broad)<br>1,620<br>1,160 |
| 182 | " | 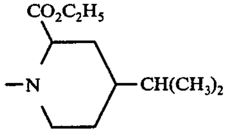 | $CH_3COOH$ | | 3 | " | 57.50<br>57.61 | 7.15<br>7.11 | 11.56<br>11.81 | 3,350 (broad)<br>1,730<br>1,620 |
| 183 | 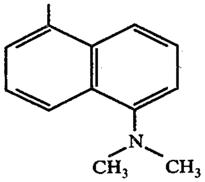 | 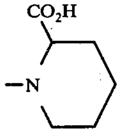 | — | 0.35 | 3 | " | 55.58<br>55.62 | 6.61<br>6.81 | 16.21<br>16.03 | 3,350 (broad)<br>1,620<br>1,140 |

Table 2-continued

Compound

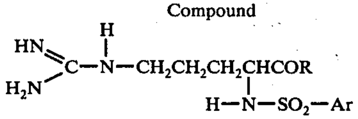 (I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) (cm[-1]) |
|---|---|---|---|---|---|---|---|---|---|---|
| 184 | 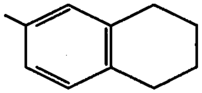 | 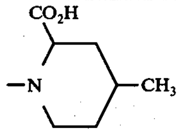 | — | | 3 | " | 55.96<br>56.12 | 7.15<br>7.28 | 14.19<br>14.07 | 3,350 (broad)<br>1,620<br>1,150 |
| 185 | " | 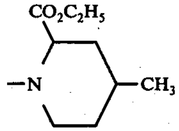 | $CH_3COOH$ | | 3 | " | 55.74<br>55.90 | 7.45<br>7.51 | 12.04<br>12.18 | 3,400 (broad)<br>1,730<br>1,625 |
| 186 | 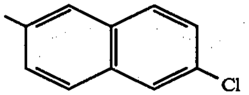 | 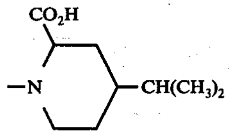 | — | | 3 | " | 54.38<br>54.08 | 6.21<br>5.91 | 12.69<br>12.39 | 3,300 (broad)<br>1,625 |
| 187 | 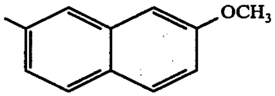 | 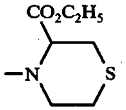 | — | | 2 | " | 52.25<br>52.36 | 6.03<br>5.98 | 12.70<br>12.51 | 3,400<br>1,735<br>1,640<br>1,160 |
| 188 | " | 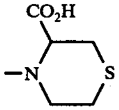 | — | | 2 | " | 50.46<br>50.61 | 5.58<br>5.63 | 13.38<br>13.40 | 3,380<br>1,620<br>1,380<br>1,155 |
| 189 | " | 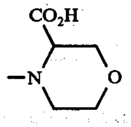 | — | 2 | 3 | " | 52.06<br>52.31 | 5.76<br>5.81 | 13.80<br>13.51 | 3,320<br>1,620<br>1,390<br>1,155 |
| 190 | " | 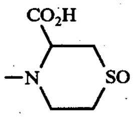 | — | | 2 | " | 48.96<br>49.13 | 5.42<br>5.38 | 12.98<br>12.75 | 3,350<br>1,620<br>1,380<br>1,150 |

Table 2-continued

Compound

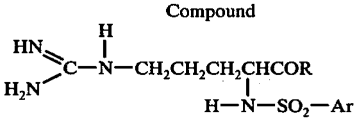

(I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 191 | 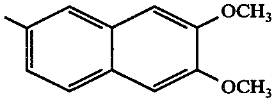 | 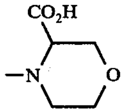 | — | 5 | 2 | " | 51.38<br>51.45 | 5.81<br>5.86 | 13.03<br>13.12 | 3,350<br>1,630<br>1,255<br>1,150 |
| 192 | 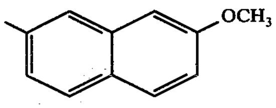 | 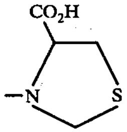 | — | | 2 | " | 49.50<br>49.31 | 5.34<br>5.40 | 13.75<br>13.68 | 3,350<br>3,200<br>1,622 |
| 193 | 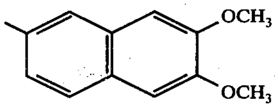 | 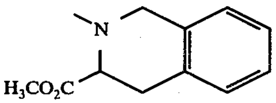 | — | | 2 | " | 58.27<br>58.45 | 5.90<br>6.03 | 11.72<br>11.53 | 3,350<br>1,740<br>1,640<br>1,260<br>1,160 |
| 194 | " | 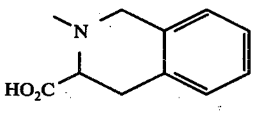 | — | 2 | 2 | " | 57.62<br>57.68 | 5.70<br>5.55 | 12.00<br>11.73 | 3,300 (broad)<br>1,620<br>1,250<br>1,150 |
| 195 | " | 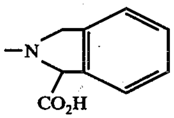 | — | 1.5 | 3 | " | 56.93<br>57.12 | 5.49<br>5.43 | 12.30<br>12.14 | 3,360<br>1,625<br>1,260<br>1,150 |
| 196 | " | 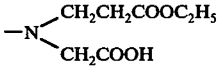 | — | 6.5 | 1 | " | 54.63<br>54.28 | 6.42<br>6.31 | 12.74<br>12.53 | 3,350 (broad)<br>1,740 |
| 197 | " | 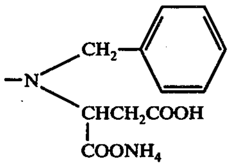 | — | | 2 | " | 53.86<br>54.16 | 5.92<br>5.62 | 13.00<br>12.70 | 3,100 (broad)<br>1,620 |

Table 2-continued

| Sample No. | Ar | Compound 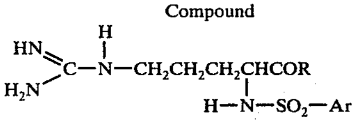 (I) R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 198 | " | 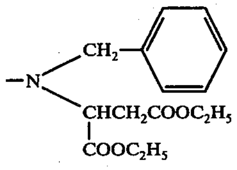 | ½ $H_2SO_3$ | | 2 | " | 54.53<br>54.23 | 6.10<br>5.80 | 9.64<br>9.34 | 1,720<br>1,630 (broad) |
| 199 | 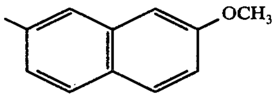 | 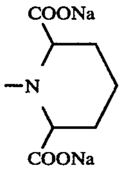 | — | | 2 | " | 48.55<br>48.31 | 4.93<br>4.64 | 11.80<br>11.53 | 3,300 (broad)<br>1,620 |
| 200 | 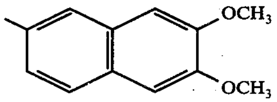 | 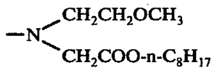 | HCl | 2 | 6 | " | 54.10<br>53.81 | 7.32<br>7.13 | 10.18<br>9.93 | 3,180 (broad)<br>1,740<br>1,630 |
| 201 | " | 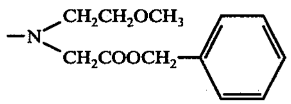 | — | | 2 | " | 57.22<br>56.98 | 6.24<br>6.18 | 11.12<br>11.31 | 3,300<br>3,150<br>1,740<br>1,650 |
| 202 | " | 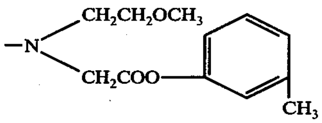 | HCl | 20 | 6 | " | 54.09<br>53.83 | 6.05<br>5.97 | 10.51<br>10.36 | 3,250<br>3,100<br>1,740<br>1,640 |
| 203 | " | 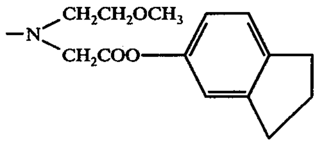 | HCl | 30 | 6 | " | 55.53<br>55.37 | 6.12<br>6.01 | 10.12<br>10.01 | 3,350<br>3,150<br>1,740<br>1,650 |

Table 2-continued

| Sample No. | Compound 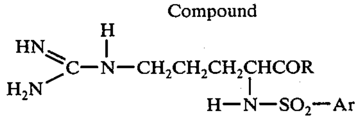 (I) Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 204 | 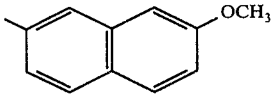 | 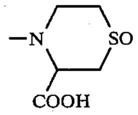 | — | 4.5 | 2 | " | 48.96<br>49.13 | 5.42<br>5.36 | 12.98<br>13.01 | 3,350<br>1,620<br>1,380 |
| 205 | " | 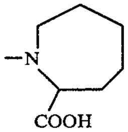 | — | 2.5 | 2 | " | 54.64<br>54.63 | 6.42<br>6.56 | 12.74<br>13.01 | 3,360<br>2,940<br>1,620<br>1,380 |
| 206 | 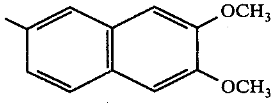 | 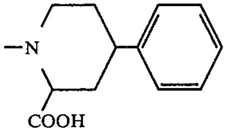 | — | 12 | 2 | " | 59.89<br>59.65 | 4.52<br>4.63 | 11.64<br>11.81 | 3,360<br>1,620<br>1,255<br>1,150 |
| 207 | " | 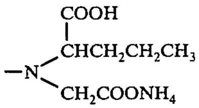 | — | 55 | 2 | " | 50.15<br>49.91 | 6.41<br>6.35 | 14.04<br>13.83 | 3,280<br>1,620 |
| 208 | " | 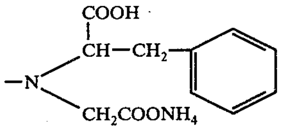 | — | | 2 | " | 53.85<br>53.61 | 5.93<br>5.76 | 13.00<br>12.84 | 3,320<br>1,610 |
| 209 | " | 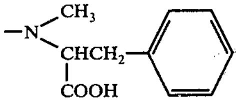 | — | 2 | 2 | " | 57.42<br>57.37 | 6.02<br>5.86 | 11.96<br>11.74 | 3,300 (broad)<br>1,600 |
| 210 | 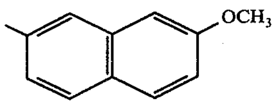 | 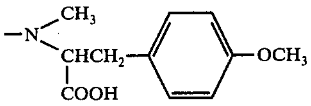 | — | | 2 | " | 57.41<br>57.33 | 6.03<br>5.94 | 11.96<br>11.73 | 3,300<br>1,610 |

Table 2-continued

Compound

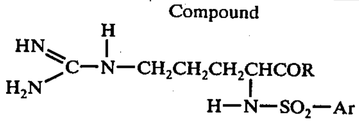 (I)

| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 211 | " | 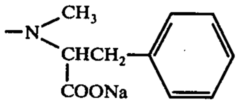 | — | 2.5 | 2 | " | 53.98<br>53.74 | 5.38<br>5.33 | 11.66<br>11.74 | 3,350<br>1,630 |
| 212 | 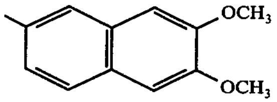 | 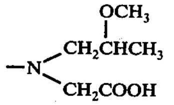 | — | 6.5 | 2 | " | 52.06<br>52.40 | 6.38<br>6.37 | 12.65<br>12.73 | 3,350 (broad)<br>1,620 |
| 213 | " | 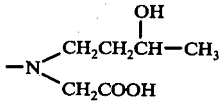 | — | | 2 | " | 52.07<br>51.95 | 6.37<br>6.27 | 12.65<br>12.84 | 3,350 (broad)<br>1,620 |
| 214 | " | 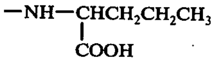 | — | 15 | 2 | " | 52.75<br>52.68 | 6.36<br>6.34 | 13.38<br>13.41 | 3,380 (broad)<br>1,620 |
| 215 | " | 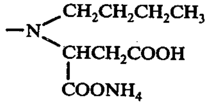 | — | | 2 | " | 50.97<br>50.67 | 6.58<br>6.61 | 13.72<br>13.39 | 3,200 (broad)<br>1,610 (broad) |
| 216 | " | 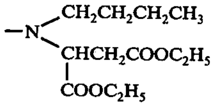 | ½ $H_2SO_3$ | | 2 | " | 52.01<br>51.77 | 6.69<br>6.50 | 10.11<br>10.00 | 1,725<br>1,620 |
| 217 | 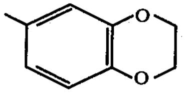 | 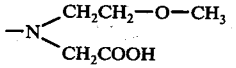 | — | | 5 | " | 46.81<br>46.63 | 6.00<br>5.94 | 14.37<br>14.23 | 3,400<br>3,300<br>1,630 |
| 218 | 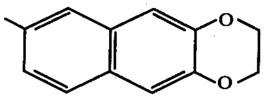 | 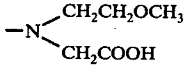 | — | | 5 | " | 51.38<br>51.24 | 5.82<br>5.79 | 13.03<br>12.87 | 3,380<br>3,300<br>1,630 |

Table 2-continued

| Sample No. | Compound 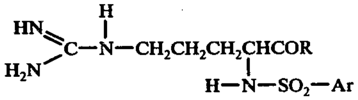 (I) Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 219 | 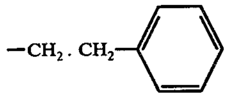 | 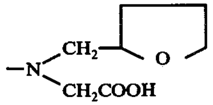 | — | | 1 | " | 52.15<br>52.03 | 6.88<br>6.73 | 14.48<br>14.68 | 3,355<br>1,630<br>1,380<br>1,305 |
| 220 | 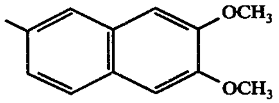 | 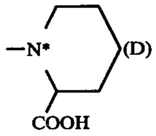 | $2H_2O$ | 2 | 2 | 195–198 | 50.42<br>50.48 | 6.54<br>6.16 | 12.25<br>12.31 | 3,320<br>1,620 |
| 221 | " | 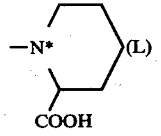 | ½ $H_2O$ | 15 | 2 | 229–233 | 52.94<br>52.73 | 6.30<br>6.15 | 12.87<br>12.93 | 3,350<br>1,620 |
| 222 | 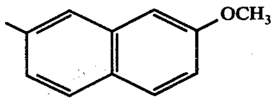 | 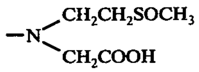 | — | 6.5 | 1 | powder | 48.78<br>48.54 | 5.77<br>5.76 | 12.93<br>13.15 | 3,320<br>1,620<br>1,390 |
| 223 | 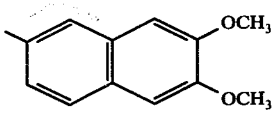 | 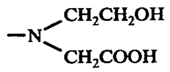 | — | | 1 | " | 50.27<br>50.11 | 5.95<br>5.87 | 13.33<br>13.34 | 3,390<br>1,630<br>1,260<br>1,160 |
| 224 | 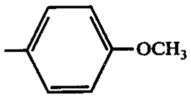 | 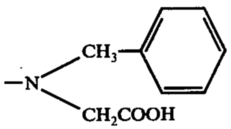 | — | | 5 | " | 53.76<br>53.66 | 5.95<br>5.83 | 14.25<br>14.19 | 3,400<br>3,200<br>1,635 |

Table 2-continued
Compound
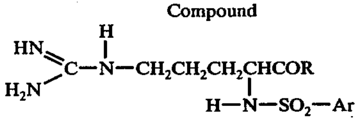 (I)
| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) (cm⁻¹) |
|---|---|---|---|---|---|---|---|---|---|---|
| 225 | 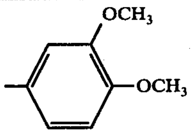 | 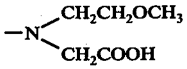 | — | | 5 | " | 46.62<br>46.53 | 6.38<br>6.21 | 14.31<br>14.43 | 3,350<br>3,150<br>1,630 |
| 226 | 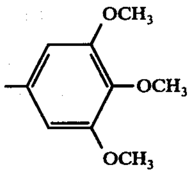 | 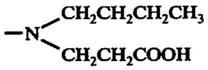 | — | | 5 | " | 49.71<br>49.84 | 7.02<br>7.26 | 13.18<br>13.36 | 3,250 (broad)<br>3,150<br>1,630 |
| 227 | " | 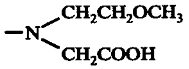 | — | | 5 | " | 46.24<br>46.31 | 6.40<br>6.53 | 13.48<br>13.41 | 3,320<br>3,150<br>1,630 |
| 228 | 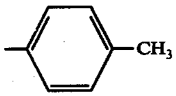 | 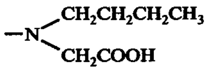 | HCl | | 1 | " | 47.74<br>47.53 | 6.75<br>6.51 | 14.65<br>14.41 | 3,340<br>3,180<br>1,640 |
| 229 | 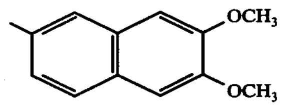 | 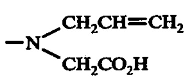 | | | 1 | | 52.95<br>52.79 | 6.00<br>5.87 | 13.43<br>13.28 | 3,350<br>3,150<br>1,620 |
| 230 | " | 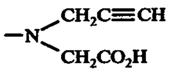 | | | 1 | | 53.16 | 5.64 | 13.48 | |
| 231 | 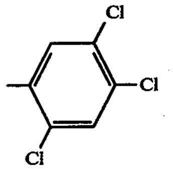 | 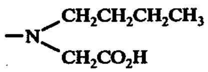 | | | 5 | | 40.71<br>40.60 | 4.95<br>4.78 | 13.19<br>13.03 | 3,360<br>3,150<br>1,620 |

Table 2-continued
Compound
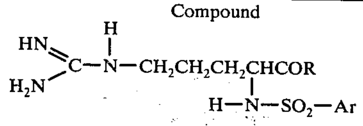
(I)
| Sample No. | Ar | R | Addition moiety | Concentration required to prolong the coagulation time by a factor of two (μM) | Preparation process (Ex. No.) | m.p. (° C) | Elementary analysis Upper: Calculated (%) Lower: Found (%) C | H | N | I.R. (KBr) (cm$^{-1}$) |
|---|---|---|---|---|---|---|---|---|---|---|
| 232 | 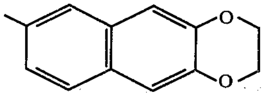 | 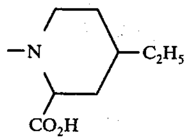 | — | | 3 | " | 55.59<br>55.54 | 6.29<br>6.14 | 12.47<br>12.35 | 3,350<br>3,150<br>1,625 |
| 233 | 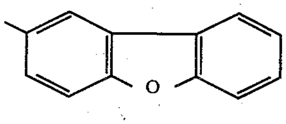 | 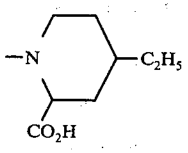 | — | | 3 | " | 57.43<br>57.26 | 6.13<br>6.04 | 12.88<br>12.71 | 3,350<br>3,130<br>1,615 |
| 234 | 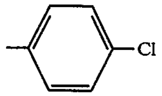 | 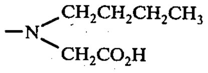 | — | | 5 | " | 46.80<br>46.61 | 6.11<br>6.05 | 15.16<br>15.23 | 3,375<br>3,150<br>1,630 |
| 235 | 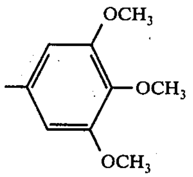 | 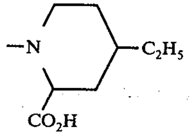 | — | | 3 | " | 50.82<br>50.71 | 6.86<br>6.69 | 12.89<br>12.57 | 3,360<br>3,120<br>1,620 |

The pharmaceutically acceptable salts of the above compounds are of course also included within the scope of this invention.

For the preparation of the compounds of this invention, various methods can be employed depending upon the particular starting materials and/or intermediates involved. Successful preparation of these compounds is possible by way of several synthetic routes which are outlined below.

(a) Condensation of an L-argininamide with an arylsulfonyl halide

This process may be illustrated as follows:

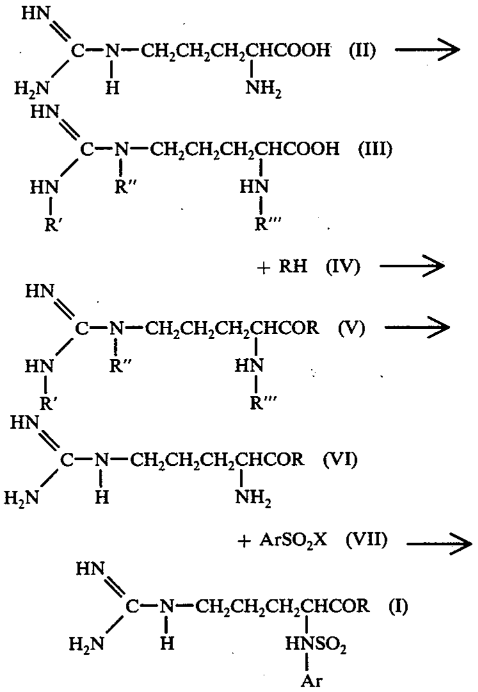

In the above formulas, R and Ar are as defined herein above; X is halogen; R''' is a protective group for the α-amino group, such as benzyloxycarbonyl or tert-butoxycarbonyl; R' and R'' are selected from the group consisting of hydrogen and protective groups for the guanidino group, such as nitro, tosyl, trityl, oxycarbonyl and the like; and at least one of R' and R'' is a protective group for the guanidino group. The $N^2$-arylsulfonyl-L-argininamide (I) is prepared by the condensation of an L-argininamide (VI) with a substantially equimolar amount of an arylsulfonyl halide (VII), preferably a chloride. The condensation reaction is generally effected in a suitable reaction-inert solvent in the presence of an excess of a base, such as an organic base (triethylamine, pyridine) or a solution of an inorganic base (sodium hydroxide, potassium carbonate), at a temperature of 0° C to the boiling temperature of the solvent for a period of 10 minutes to 15 hours.

The preferred solvents for the condensation include benzene-diethyl ether, diethyl ether-water and dioxane-water.

After the reaction is complete, the formed salt is extracted with water, and the solvent is removed by such standard means as evaporation under reduced pressure to give the $N^2$-arylsulfonyl-L-argininamide (I), which can be purified by trituration or recrystallization from a suitable solvent, such as diethyl ether-tetrahydrofuran, diethyl ether-methanol and water-methanol, or may be chromatographed on silica gel. The L-argininamides (VI) starting materials required for the condensation reaction can be prepared by protecting the guanidino and α-amino groups of L-arginine (II) via nitration, acetylation, formylation, phthaloylation, trifluoroacetylation, p-methoxybenzyloxycarbonylation, benzoylation, benzyloxycarbonylation, tert-butoxycarbonylation or tritylation and then condensing the formed $N^G$-substituted-$N^2$-substituted-L-arginine (III) with a corresponding amino acid derivative (IV) by such a conventional process as the acid chloride method, azide method, mixed anhydride method, activated ester method or carbodiimide method, and thereafter selectively removing the protective groups from the formed $N^G$-substituted-$N^2$-substituted-L-argininamide (V).

The amino acid derivatives (IV) which are the starting materials for the preparation of the $N^G$-substituted-$N^2$-substituted-L-argininamides (V) are represented by the following formulas:

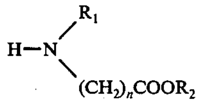
(VIII)

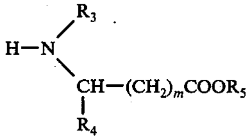
(IX)

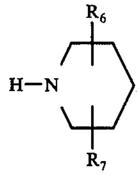
(X)

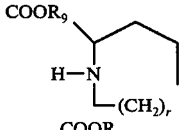
(XI)

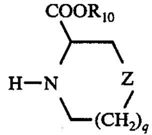
(XII)

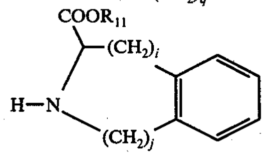
(XIII)

In the above formulas, $R_1$, $R_2$, $R_3$, $R_4$, $R_5$, $R_6$, $R_7$, $R_9$, $R_{10}$, $R_{11}$, Z, n, m, r, q, i, and j are as defined herein above.

The amino acid derivatives of the above formula (VIII) or (IX) can be prepared by the condensation of a haloacetate, 3-halopropionate or 4-halobutyrate with an appropriate amine having the formula $R_1NH_2$ or $R_3NH_2$. (See, J. Org. Chem., 25 728-732 (1960)).

The condensation reaction is generally carried out without a solvent or in a solvent, such as benzene or ether, in the presence of an organic base, such as triethylamine or pyridine, at a temperature of 0° C to 80° C for a period of 10 minutes to 20 hours. After the reaction is complete, the formed amino acid derivative is separated by such conventional means as extraction with a suitable solvent or evaporation of the reaction solvent and thereafter purified by distillation under reduced pressure.

Among the amino acid derivatives, amino acid tert-butyl ester derivatives are preferred, because they are easily converted to other ester derivatives by acidolysis in the presence of a corresponding alcohol employing an inorganic acid (HCl, $H_2SO_4$, etc.) or an organic acid (toluenesulfonic acid, trifluoroacetic acid, etc.).

In accordance with the process employed for preparing 2-piperidinecarboxylic acid derivatives (X), the following scheme is illustrative:

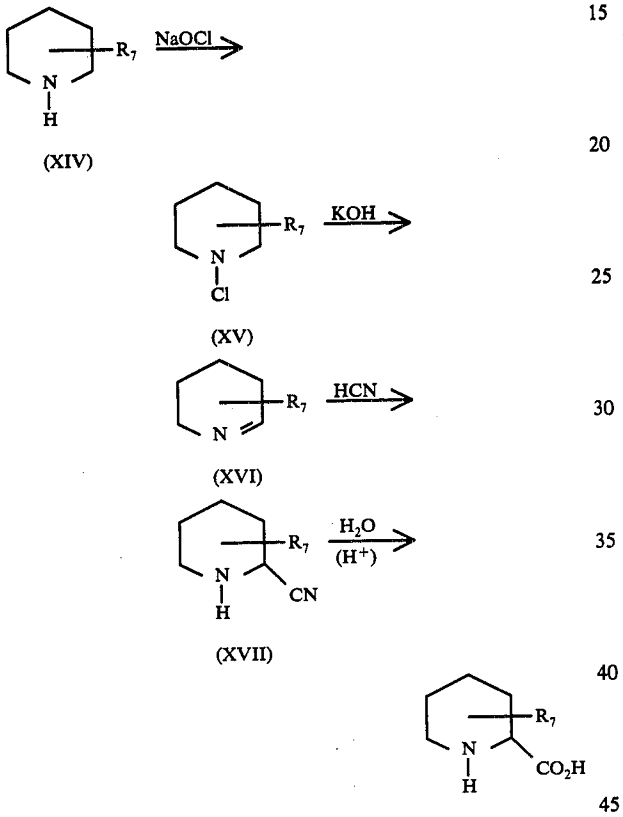

(XIV)
(XV)
(XVI)
(XVII)
(XVIII)

In the first reaction of the aforementioned scheme, an appropriately substituted piperidine (XIV) is contacted with an aqueous sodium hypochlorite solution at a temperature of −5° to 0° C. The resultant product (XV) is isolated by extraction with a solvent, e.g., diethyl ether, and then treated with potassium hydroxide in a lower alkanol solvent to give the 1,2-dehydropiperidine (XVI). The action of cyanogenating agents, e.g., hydrogen cyanide or sodium cyanide converts the 1,2-dehydropiperidines (XVI) to the corresponding 2-cyano analogs (XVII). Hydrolysis of the 2-cyanopiperidines (XVII) to yield the 2-piperidinecarboxylic acids (XVIII) is effected by treatment of the 2-cyanopiperidines (XVII) with an inorganic acid, such as hydrochloric acid or sulfuric acid.

The arylsulfonyl halides (VII) which are the starting materials for the preparation of the $N^2$-arylsulfonyl-L-argininamides (I) can be prepared by halogenating the requisite arylsulfonic acids or their salts, e.g., sodium salts, by conventional methods well known to those skilled in the art.

In practice, halogenation is carried out without a solvent or in a suitable solvent e.g., halogenated hydrocarbons or DMF in the presence of a halogenating agent, e.g., phosphorous oxychloride, thionyl chloride, phosphorous trichloride, phosphorous tribromide or phosphorous pentachloride, at a temperature of −10° C to 200° C for a period of 5 minutes to 5 hours. After the reaction is complete, the reaction product is poured into ice water and then extracted with a solvent such as ether, benzene, ethyl acetate, chloroform or the like.

The arylsulfonyl halide can be purified by recrystallization from a suitable solvent such as hexane, benzene or the like.

(b) Removal of the $N^G$-substituent from an $N^G$-substituted-$N^2$-arylsulfonyl-L-argininamide This process may be illustrated as follows:

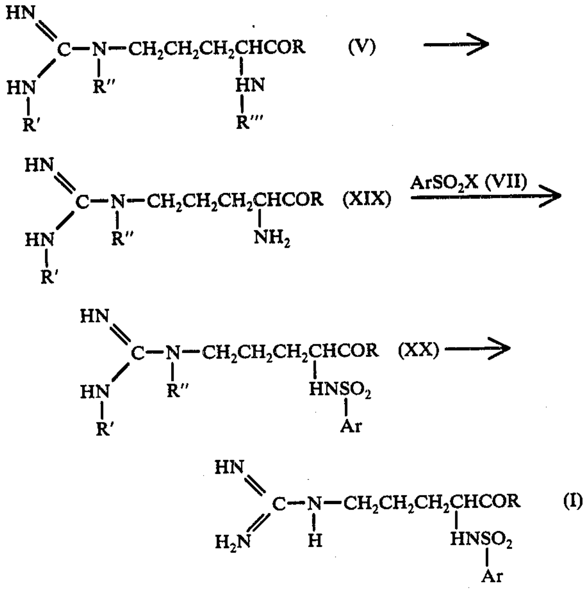

(V)
(XIX)
(XX)
(I)

In the above formulas, R, Ar, X, R′, R″ and R‴ are as defined herein above.

The $N^2$-arylsulfonyl-L-argininamide (I) is prepared by removing the $N^G$-substituent from an $N^G$-substituted-$N^2$-arylsulfonyl-L-argininamide (XX) by means of acidolysis or hydrogenolysis.

The acidolysis is generally effected by contacting the $N^G$-substituted-$N^2$-arylsulfonyl-L-argininamide (XX) and an excess of an acid such as hydrogen fluoride, hydrogen chloride, hydrogen bromide or trifluoroacetic acid, without a solvent or in a solvent, such as an ether (tetrahydrofuran, dioxane), an alcohol (methanol, ethanol) or acetic acid at a temperature of −10° C to 100° C, and preferably at room temperature for a period of 30 minutes to 24 hours.

The products are isolated by evaporation of the solvent and the excess acid, or by trituration with a suitable solvent followed by filtration and drying.

Because of the use of the excess acid, the products are generally the acid addition salts of the $N^2$-arylsulfonyl-L-argininamides (I), which can be easily converted to a free amide by neutralization.

The removal of the nitro group and the oxycarbonyl group, e.g., benzyloxycarbonyl, p-nitrobenzyloxycarbonyl, is readily accomplished by the hydrogenolysis.

At the same time, the benzyl ester moiety which can be included in the R group is converted to the carboxyl group by the hydrogenolysis.

The hydrogenolysis is effected in a reaction-inert solvent, e.g., methanol, ethanol, tetrahydrofuran or dioxane, in the presence of a hydrogen-activating catalyst, e.g., Raney nickel, palladium or platinum, in a hydrogen atmosphere at a temperature of 0° C to the boiling temperature of the solvent for a period of 2 hours to 120 hours.

The hydrogen pressure is not critical, and atmospheric pressure is sufficient.

The $N^2$-arylsulfonyl-L-argininamides (I) are isolated by filtration of the catalyst followed by evaporation of the solvent.

The $N^2$-arylsulfonyl-L-argininamides can be purified in the same manner as described above.

The $N^G$-substituted-$N^2$-arylsulfonyl-L-argininamides (XX) starting materials can be prepared by condensing an $N^G$-substituted-$N^2$-substituted-L-arginine (III) (generally the $N^G$-substituent is nitro or acyl, and the $N^2$-substituent is a protective group for the amino group, such as benzyloxycarbonyl, tert-butoxycarbonyl, or the like) and a corresponding amino acid derivative (IV), selectively removing only the $N^2$-substituent of an $N^G$-substituted-$N^2$-substituted L-argininamide (V) by means of catalytic hydrogenolysis or acidolysis, and then condensing the thus obtained $N^G$-substituted-L-argininamide (XIX) with an arylsulfonyl halide (VII), preferably a chloride in the presence of a base in a solvent. These reaction conditions are as described above in the condensation of an L-argininamide with an arylsulfinyl halide, and the removal of the $N^G$-substituent from an $N^G$-substituted-$N^2$-arylsulfonyl-L-argininamide.

(c) Condensation of an $N^2$-arylsulfonyl-L-arginyl halide with an amino acid derivative This process may be illustrated as follows:

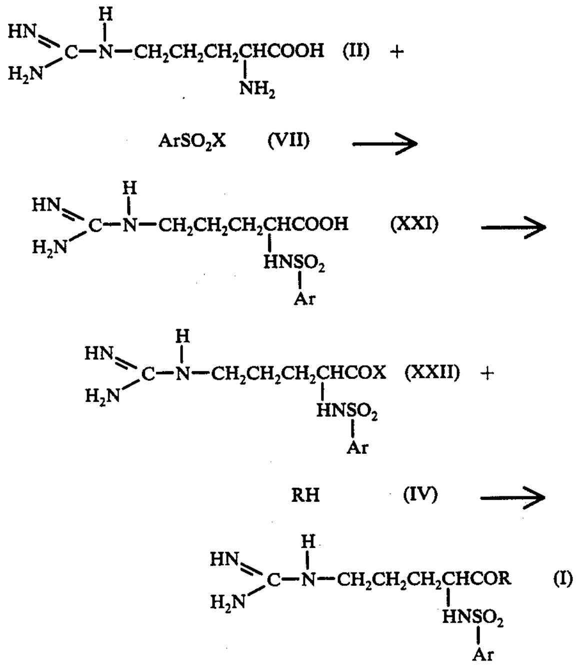

In the above formulas, R, Ar and X are as defined herein above.

The $N^2$-arylsulfonyl-L-argininamide (I) is prepared by the condensation of an $N^2$-arylsulfonyl-L-arginyl halide (XXII), preferably a chloride with at least an quimolar amount of an amino acid derivative (IV). The condensation reaction can be carried out without an added solvent in the presence of a base. However, satisfactory results will be obtained with the use of a solvent such as basic solvents (dimethylformamide, dimethylacetamide, etc.) or halogenated solvents (chloroform, dichloromethane, etc.).

The amount of the solvent to be used is not critical and may vary from about 5 to 100 times the weight of the $N^2$-arylsulfonyl-L-arginyl halide (XXII).

Preferred condensation reaction temperatures are in the range of from −10° C to room temperature. The reaction time is not critical, but varies with the amino acid derivative (IV) employed. In general, a period of from 5 minutes to 10 hours is operable. The obtained $N^2$-arylsulfonyl-L-argininamide can be isolated and purified in the same manner as described above.

The $N^2$-arylsulfonyl-L-arginyl halide (XXII) starting materials required for the condensation reaction can be prepared by reacting an $N^2$-arylsulfonyl-L-arginine (XXI) with at least an equimolar amount of a halogenating agent such as thionyl chloride, phosphorous oxychloride, phosphorus trichloride, phosphorous pentachloride or phosphorus tribromide. The halogenation can be carried out with or without an added solvent. The preferred solvents are chlorinated hydrocarbons such as chloroform and dichloromethane, and ethers such as tetrahydrofuran and dioxane.

The amount of the solvent to be used is not critical and may vary from about 5 to 100 times the weight of the $N^2$-arylsulfonyl-L-arginine (XXI).

Preferred reaction temperature are in the range of −10° C to room temperature. The reaction time is not critical, but varies with the halogenating agent and reaction temperature. In general, a period of 15 minutes to 5 hours is operable.

The $N^2$-arylsulfonyl-L-arginines (XXI) which are the starting materials for the preparation of the $N^2$-arylsulfonyl-L-arginyl halides (XXII) can be prepared by the condensation of L-arginine (II) with a substantially equimolar amount of arylsulfonyl halides (VII), by a method similar to that described in the condensation of an L-argininamide with an arylsulfonyl halide.

(d) Guanidylation of an $N^2$-arylsulfonyl-L-ornithinamide or an acid addition salt thereof This process may be illustrated as follows:

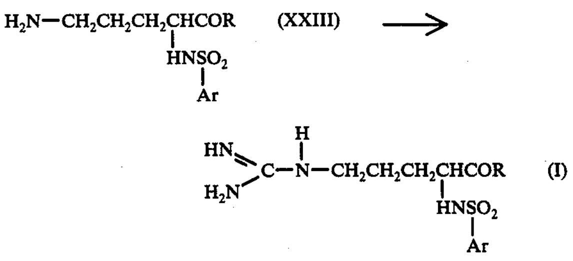

In the above formulas, R and Ar are as defined herein above.

The $N^2$-arylsulfonyl-L-argininamide (I) is prepared by guanidylating an $N^2$-arylsulfonyl-L-ornithinamide (XXIII) with an ordinary guanidylating agent such as an O-alkylisourea, S-alkylisothiourea, 1-guanyl-3,5-dimethylpyrazole or carbodiimide. The preferred guanidylating agents are the O-alkylisourea and the S-alkylisothiourea.

The guanidylation of the $N^2$-arylsulfonyl-L-ornithinamide (XXIII) with the O-alkylisourea or S-alkylisothiourea is generally effected in a solvent in the presence of a base at a temperature of from 0° C to the boiling temperature of the solvent for a period of from 30 minutes to 50 hours.
Examples of the preferred bases are triethylamine, pyridine, sodium hydroxide and sodium methoxide. The base is used in an amount of 0.01 to 0.1 equivalent to the $N^2$-arylsulfonyl-L-ornithinamide.

Examples of the preferred solvents are water, water-ethanol and water-dioxane.

After the reaction is complete, the $N^2$-arylsulfonyl-L-argininamide (I) is isolated by evaporation of the solvent followed by removal of the excess base and the formed salt by a water wash.

It is well recognized in the art that an ester derivative of the $N^2$-arylsulfonyl-L-argininamide (I) wherein $R_2$, $R_5$, $R_8$, $R_9$, $R_{10}$ or $R_{11}$ is alkyl, aralkyl, aryl or 5-indanyl, can be prepared from a carboxylic acid derivative of the $N^2$-arylsulfonyl-L-argininamide wherein $R_2$, $R_5$, $R_8$, $R_9$, $R_{10}$ or $R_{11}$ is hydrogen, by the conventional esterification methods well known to those skilled in the art. It is also well recognized in the art that the carboxylic acid derivative can be prepared from the ester derivative by the conventional hydrolysis or acidolysis methods. The conditions under which esterification, hydrolysis or acidolysis would be carried out will be each apparent to those skilled in the art.

The $N^2$-arylsulfonyl-L-argininamide (I) of this invention forms acid addition salts with any of a variety of inorganic and organic acids. Some of the $N^2$-arylsulfonyl-L-argininamides containing a free carboxyl group, wherein $R_2$, $R_5$, $R_8$, $R_9$, $R_{10}$ or $R_{11}$ is hydrogen, forms salt with any of a variety of inorganic and organic bases.

The product of the reactions described above can be isolated in the free form or in the form of salts. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting one of the free carboxylic acids with a base, such as sodium hydroxide, potassium hydroxide, ammonium hydroxide, triethylamine, procaine, dibenzylamine, 1-ephenamine, N,N'-dibenzylethylenediamine, N-ethylpiperidine or the like.

Likewise, treatment of the salts with a base or acid results in a regeneration of the free amide.

As stated above, the $N^2$-arylsulfonyl-L-argininamides, and the salts thereof of this invention are characterized by their highly specific inhibitory activity in mammals against thrombim as well as by their substantial lack of toxicity, and therefore these compounds are useful in the determination of thrombin in blood as diagnostic reagents, and/or for the medical control or prevention of thrombosis.

The compounds of this invention are also useful as an inhibitor of platelet aggregation.

The antithrombotic activity of the $N^2$-arylsulfonyl-L-argininamide of this invention was compared with that of a known antithrombotic agent, $N^2$-(p-tolylsulfonyl)-L-arginine methyl ester, by determining the fibrinogen coagulation time. The measurement of the fibrinogen coagulation time was conducted as follows:

An 0.8 ml aliquot of a fibrinogen solution; which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath.

Immediately after mixing, the reaction mixture was transferred from the ice bath to a bath maintained at 25° C.

Coagulation times were taken as the period between the time of transference to the 25° C bath and the time of the first appearance of fibrin threads. In the cases where no drug samples were added, the coagulation time was 50–55 seconds. The experimental results are summarized in Table 2. The term "concentration required to prolong the coagulation time by a factor of two" is the concentration of an active ingredient required to prolong the normal coagulation time 50–55 seconds to 100–110 seconds.

The concentration required to prolong the coagulation time by a factor of two for the known antithrombotic agent, $N^2$-(p-tolysulfonyl)-L-arginine methyl ester, was 1,100$\mu$m. The inhibitors are shown in Table 1 by indicating R and Ar in the formula (I) and the addition moiety.

When a solution containing an $N^2$-naphthylsulfonyl-L-argininamide of this invention was administered intravenously into animal bodies, the high antithrombitic activity in the circulating blood was maintained for from one to three hours. The halflife for decay of the anti-thrombotic compounds of this invention in circulating blood was shown to be approximately 60 minutes; the physiological conditions of the host animals (rat, rabbit, dog and chimpanzee) were well maintained. The experimental decrease of fibrinogen in animals caused by infusion of thrombin was satisfactorily controlled by simultaneous infusion of the compounds of this invention.

The acute toxicity values ($LD_{50}$) determined by intraperitoneal administration of substances of formula (I) in mice (male, 20 g) range from about 1,000 to 10,000 milligrams per kilogram of body weight.

Representative $LD_{50}$ values for the compounds of this invention are shown in the following Table.

| Compound | $LD_{50}$ (mg/kg) |
|---|---|
| $N^2$-(7-methyl-2-naphthylsulfonyl)-L-arginyl-N-butylglycine | >1,500 |
| $N^2$-(6,7-dimethoxy-2-naphthylsulfonyl)-L-arginyl-N-(2-methoxyethyl)glycine | 1,900–2,400 |
| $N^2$-(6,7-dimethoxy-2-naphthylsulfonyl)-L-arginyl-N-(2-ethoxyethyl)-$\beta$-alanine | 660–1,000 |
| $N^2$-(4,6-dimethoxy-2-naphthylsulfonyl)-L-arginyl-N-(2-methoxyethyl)glycine | 660–1,000 |
| $N^2$-(7-methoxy-2-naphthylsulfonyl)-L-arginyl-N-(2-methoxyethyl)glycine | 2,000 |
| $N^2$-(5,6,7,8-tetrahydro-1-naphthylsulfonyl)-L-arginyl-N-(2-methoxyethyl)glycine | >1,500 |
| $N^2$-(6,7-dimethyl-1-naphthylsulfonyl)-L-arginyl-N-(2-methoxyethyl)glycine | >1,500 |
| $N^2$-(6,7-dimethoxy-2-naphthylsulfonyl)-L-arginyl-N-(2-ethylthioethyl)glycine | >1,000 |
| $N^2$-(6,7-dimethoxy-2-naphthylsulfonyl)-L-arginyl-N-benzylglycine | >1,000 |
| $N^2$-(4,6-dimethoxy-2-naphthylsulfonyl)-L-arginyl-N-benzylglycine | >1,000 |
| $N^2$-(5-methoxy-1-naphthylsulfonyl)-L-arginyl-N-benzylglycine | >1,000 |
| $N^2$-(6,7-dimethoxy-2-naphthylsulfonyl)-L-arginyl-N-phenethylglycine | >1,500 |

-continued

| Compound | $LD_{50}$ (mg/kg) |
|---|---|
| $N^2$-(6,7-dimethoxy-2-naphthylsulfonyl)-L-arginyl-N-cyclohexylglycine | >1,500 |
| $N^2$-(6,7-dimethoxy-2-naphthylsulfonyl)-L-arginyl-N-cyclohexylmethylglycine | >1,500 |
| $N^2$-(7-methyl-2-naphthylsulfonyl)-L-arginyl-N-tetrahydrofurfurylglycine | 600 |
| $N^2$-(6,7-dimethoxy-2-naphthylsulfonyl)-L-arginyl-N-tetrahydrofurfurylglycine | 620 |
| $N^2$-(6,7-dimethoxy-2-naphthylsulfonyl)-L-arginyl-N-butylalanine | >1,500 |
| $N^2$-(4,6-dimethoxy-2-naphthylsulfonyl)-L-arginyl-N-cyclohexylmethylalanine | >1,500 |
| 1-[$N^2$-(6,7-dimethoxy-2-naphthylsulfonyl)-L-arginyl]-2-piperidinecarboxylic acid | 1,500 |
| Ethyl[1-$N^2$-(7-methoxy-2-naphthylsulfonyl)-L-arginyl]-4-methyl-2-piperidinecarboxylate | 670–1,000 |
| 1-[$N^2$-(4,6-dimethoxy-2-naphthylsulfonyl)-L-arginyl]-4-methyl-2-piperidinecarboxylic acid | 670–1,000 |
| 1-[$N^2$-(1-naphthylsulfonyl)-L-arginyl]-4-methyl-2-piperidinecarboxylic acid | 700–1,000 |
| 1-[$N^2$-(5-dimethylamino-1-naphthylsulfonyl)-L-arginyl]-2-piperidinecarboxylic acid | 700–1,000 |
| 4-[$N^2$-(7-methoxy-2-naphthylsulfonyl)-L-arginyl]-3-morpholinecarboxylic acid | >1,000 |
| 2-[$N^2$-(6,7-dimethoxy-2-naphthylsulfonyl)-L-arginyl]-1,2,3,4-tetrahydroisoquinoline-3-carboxylic acid | >1,000 |
| 2-[$N^2$-(6,7-dimethoxy-2-naphthylsulfonyl)-L-arginyl]-1-isoindolinecarboxylic acid | >1,000 |

On the other hand, $LD_{50}$ values for $N^2$-dansyl-N-butyl-L-argininamide and $N^2$-dansyl-N-methyl-N-butyl-L-argininamide are 75 and 70 milligrams per kilogram, respectively.

The therapeutic agents in this invention may be administered to mammals, including humans, alone or in combination with pharmaecutically acceptable carriers, the proportion of which is determined by the solubility and chemical nature of the compound, chosen route of administration and standard pharmaecutical practice. For example, the compounds may be injected parenterally, that is, intramuscularly, intraveneously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents. Physicians will determine the dosage of the present therapeutic agents which will be most suitable for humans, and dosages vary with the mode of administration and the particular compound chosen. In addition, the dosage will vary with the particular patient under treatment. When the composition is administered orally, a larger quantity of the active agent will be required to produce the same effect as caused with a smaller quantity given parenterally. The therapeutic dosage is generally 10–50 mg/kg of active ingredient parenterally, 10–500 mg/kg orally per day. Having generally described the invention, a more complete understanding can be obtained by reference to certain specific examples, which are included for purposes of illustration only and are not intended to be limiting unless otherwise specified.

It is to be understood that the present invention includes pharmaceutical compositions containing a compound of the invention as an active ingredient. Such compositions may be in the forms described above. In particular, the invention includes such compositions in unit dose form.

EXAMPLE 1

(A) $N^2$-(6,7-dimethoxy-2-naphthylsulfonyl)-L-arginine: To a well stirred solution of 83.6 g of L-arginine in 800 ml of 10% potassium carbonate solution was added 114.7 g of 6,7-dimethoxynaphthalenesulfonyl chloride in 800 ml of benzene. The reaction mixture was stirred at 60° C for 5 hours, during which time the product precipitated. After one hour at room temperature, the precipitate was filtered and washed successively with benzene and water to give 129 g (76 percent) of $N^2$-(6,7-dimethoxy-2-naphthylsulfonyl)-L-arginine, M.P. 252°-5° C.

(B) $N^2$-(6,7-dimethoxy-2-naphthylsulfonyl)-L-arginyl chloride;

A suspension of 2.00 g of $N^2$-(6,7-dimethoxy-2-naphthylsulfonyl)-L-arginine in 20 ml of thionyl chloride was stirred for 2 hours at room temperature. Addition of cold dry diethyl ether resulted in a precipitate which was collected by filtration and washed several times with dry diethyl ether to give $N^2$-(6,7-dimethoxy-2-naphthylsulfonyl)-L-arginyl chloride.

(C) $N^2$-(6,7-dimethyl-2-naphthylsulfonyl)-L-arginyl-N-butylglycine tert-butyl ester: To a stirred solution of 2.64 g of N-butylglycine tert-butyl ester in 20 ml of chloroform was carefully added $N^2$-(6,7-dimethoxy-2-naphthylsulfonyl)-L-arginyl chloride obtained above. The reaction mixture was allowed to stand at room temperature for one hour. At the end of this period, the reaction mixture was washed twice with 20 ml of saturated sodium chloride solution and evaporated to dryness. The residue was triturated with a small amount of water to give a crystalline material. This was collected by filtration and recrystallized from ethanol-ethyl ether to give 2.28 g (82 percent) of $N^2$-(6,7-dimethoxy-2-naphthylsulfonyl)-L-arginyl-N-butylglycine tert-butyl ester, M.P. 164°-166° C, I.R. (KBr): 3,390, 3,165, 1,735, 1,370 $cm^{-1}$.

Analysis - Calcd. for $C_{28}H_{43}O_7N_5S.\frac{1}{2}H_2SO_3$ (percent): C, 52.98; H, 7.00; N, 11.04 Found (percent): C, 52.69; H, 6.98; N, 10.86

(D) $N^2$-(6,7-dimethoxy-2-naphthylsulfonyl)-L-arginyl-N-butylglycine: To a solution of 2.00 g of $N^2$-(6,7-dimethoxy-2-naphthylsulfonyl)-L-arginyl-N-butylglycine tert-butyl ester in 20 ml of chloroform was added 50 ml of 15% HCl-ethyl acetate. The reaction mixture was stirred for 5 hours at room temperature. At the end of this period, the reaction mixture was evaporated to dryness. The residue was washed several times with dry diethyl ether and chromatographed on 80 ml of Daiaion ® SK 102 ion exchange resin (200-300 mesh, $H^+$ form, manufactured by Mitsubishi Chemical Industries Limited) packed in water, washed with water and eluted with 3% ammonium hydroxide solution.

The fraction eluted from 3% ammonium hydroxide solution was evaporated to dryness to give 1.43 g (79 percent) of $N^2$-(6,7-dimethoxy-2-naphthylsulfonyl)-L-arginyl-N-butylglycine as an amorphous solid, I.R. (KBr): 3,360, 3,140, 1,622 $cm^{-1}$.

Analysis - Calcd. for $C_{24}H_{35}N_5O_7S$ (percent): C, 53.62; H, 6.56; N, 13.03 Found (percent): C, 53.48; H, 6.43; N, 12.98

The following compounds are prepared in a similar manner:

$N^2$-(7-methyl-2-naphthylsulfonyl)-L-arginyl-N-butyl-β-alanine $N^2$-(7-methyl-2-naphthylsulfonyl)-N-(2-methoxyethyl)-N-(3-carboxypropyl)-L-argininamide $N^2$-(5-methoxy-1-naphthylsulfonyl)-L-arginyl-N-(2-methylthioethyl)glycine $N^2$-(5-methoxy-1-naphthylsulfonyl)-L-arginyl-N-(2-methylthioethyl)glycine tert-butyl ester $N^2$-(5-methoxy-1-naphthylsulfonyl)-L-arginyl-N-(2-methylthioethyl)-β-alanine $N^2$-(6,7-diethoxy-2-naphthylsulfonyl)-L-arginyl-N-(2-methylthioethyl)glycine $N^2$-(6-methoxy-2-naphthylsulfonyl)-L-arginyl-N-(2-methylthioethyl)glycine $N^2$-(6,7-dimethoxy-2-naphthylsulfonyl)-N-(2-methylthioethyl)-N-(3-carboxypropyl)-L-argininamide $N^2$-(6,7-dimethoxy-2-naphthylsulfonyl)-N-(3-methylthiopropyl)glycine $N^2$-(6,7-dimethoxy-2-naphthylsulfonyl)-L-arginyl-N-(2-ethylthioethyl)-β-alanine $N^2$-(6,7-dimethoxy-2-naphthylsulfonyl)-L-arginyl-N-benzylglycine benzyl ester $N^2$-(6,7-dimethoxy-2-naphthylsulfonyl)-N-benzyl-N-(3-tert-butoxycarbonylpropyl)-L-argininamide $N^2$-(6,7-diethoxy-2-naphthylsulfonyl)-L-arginyl-N-cyclohexylglycine 4-N-[$N^2$-(6,7-dimethoxy-2-naphthylsulfonyl)-L-arginyl]-N-cyclohexylaminobutyric acid $N^2$-(4,6-dimethoxy-2-naphthylsulfonyl)-L-arginyl-N-phenethyl-β-alanine $N^2$-(6-methoxy-2-naphthylsulfonyl)-L-arginyl-N-(3-phenylpropyl)glycine $N^2$-(5-methoxy-1-naphthylsulfonyl)-L-arginyl-N-benzyl-β-alanine $N^2$-(5-nitro-1-naphthylsulfonyl)-L-arginyl-N-tetrahydrofurfurylglycine $N^2$-(7-hydroxy-2-naphthylsulfonyl)-L-arginyl-N-tetrahydrofurfurylglycine $N^2$-(5-cyano-1-naphthylsulfonyl)-L-arginyl-N-tetrahydrofurfurylglycine $N^2$-(6,7-dimethoxy-2-naphthylsulfonyl)-L-arginyl-N-tetrahydrofurfuryl-β-alanine $N^2$-(7-methyl-2-naphthylsulfonyl)-L-arginyl-N-tetrahydrofurfuryl-β-alanine $N^2$-(6,7-dimethoxy-2-naphthylsulfonyl)-L-arginyl-N-tetrahydrofurfurylalanine $N^2$-(7-methoxy-2-naphthylsulfonyl)-N-(3-carboxypropyl)-N-tetrahydrofurfuryl-L-argininamide $N^2$-(7-methoxy-2-naphthylsulfonyl)-L-arginyl-N-butylalanine $N^2$-(7-methoxy-2-naphthylsulfonyl)-L-arginyl-N-pentylalanine $N^2$-(5-methoxy-1-naphthylsulfonyl)-L-arginyl-N-butylalanine $N^2$-(6,7-dimethoxy-2-naphthylsulfonyl)-L-arginyl-N-isobutylalanine $N^2$-(7-methoxy-2-naphthylsulfonyl)-L-arginyl-N-benzylalanine $N^2$-(6,7-dimethoxy-2-naphthylsulfonyl)-L-arginyl-N-(3-phenylpropyl)alanine $N^2$-(5-methoxy-1-naphthylsulfonyl)-L-arginyl-N-benzylalanine $N^2$-(7-methoxy-2-naphthylsulfonyl)-L-arginyl-N-cyclohexylalanine $N^2$-(6,7-dimethoxy-2-naphthylsulfonyl)-L-arginyl-N-cyclohexylmethylalanine $N^2$-(6,7-dimethoxy-2-naphthylsulfonyl)-L-arginyl-N-butylbutyrine $N^2$-(6,7-dimethoxy-2-naphthylsulfonyl)-L-arginyl-N-(3-furylmethyl)glycine $N^2$-(6,7-dimethoxy-2-naphthylsulfonyl)-L-arginyl-N-(tetrahydro-3-furylmethyl)glycine $N^2$-(6,7-dimethoxy-2-naphthylsulfonyl)-L-arginyl-N-(2-thenyl)glycine $N^2$-(7-methoxy-2-naphthylsulfonyl)-L-arginyl-N-(3-thenyl)glycine $N^2$-(6,7-dimethoxy-2-naphthylsulfonyl)-L-arginyl-N-(tetrahydro-2-thenyl)glycine $N^2$-(7-methoxy-2-naphthylsulfonyl)-L-arginyl-N-)Tetrahydro-3-thenyl)glycine $N_2$-(6,7-dimethoxy-2-naphthylsulfonyl)-L-arginyl-N-(2-acetylethyl)glycine $N_2$-(7-methoxy-2-naphthylsulfonyl)-L-arginyl-N-(4-methoxyfuryl)glycine $N_2$-(7-methyl-2-naphthylsulfonyl)-L-arginyl-N-(5-methylfurfuryl)glycine $N_2$-(6,7-dimethoxy-2-naphthylsulfonyl)-L-arginyl-N-(1,4-diacylohexylmethyl)glycine 1-($N_2$-(6,7-dimethoxy-2-naphthylsulfonyl)-L-arginyl)-4-methoxy piperidine-2-carbonxylic acid 1-($N_2$-(6,7-dimethoxy-2-naphthylsulfonyl)-L-arginyl)-5-methylhexamethyleneimine-2-carbonxylic acid 1-($N_2$-(3,7-dimethyl-2-dibenzofluranyl)-L-arginyl)-4,4-dimethyl-2-piperidine carboxylic acid $N_2$-(3-methoxy-5,6,7,8-tetrahydro-2-naphthylsulfonyl)-L-arginyl-N-(tetrahydro-2-pyranylmethyl)glycine

EXAMPLE 2

(A) $N^2$-(6-methoxy-2-naphthylsulfonyl)-L-arginyl chloride. A suspension of 2.5 g of $N^2$-(6-methoxy-2-naphthylsulfonyl)-L-arginine in 20 ml of thionyl chloride was stirred for 2 hours at room temperature. Addition of cold dry ethyl ether resulted in a precipitate which was collected by filtration and washed several times with dry ethyl ether to give $N^2$-(6-methoxy-2-naphthylsulfonyl)-L-arginyl chloride.

(B) Ethyl 1-[$N^2$-(6-methoxy-2-naphthylsulfonyl)-L-arginyl]-2-piperidinecarboxylate To a stirred solution of 2.2 g of ethyl 2-piperidine-carboxylate and 4.1 ml of triethylamine in 50 ml of chloroform, which was cooled in an ice-salt bath, was added in portions $N^2$-(6-methoxy-2-naphthylsulfonyl)-L-arginyl chloride obtained above. The reaction mixture was stirred overnight at room temperature. At the end of this period, 500 ml of chloroform was added and the chloroform solution was washed twice with 50 ml of saturated sodium chloride solution, dried over anhydrous sodium sulfate and evaporated in vacue. The oily residue was washed with ethyl ether to give 2.9 g of powdery ethyl 1-[$N^2$-(6-methoxy-2-naphthyl-sulfonyl)-L-arginyl]-2-piperidinecarboxylate. For analysis of the product, a portion of the product was converted to the flavianate, M.P. 192°-3° C. I.R. (KBr): 3,210, 1,747, 1,638 $cm^{-1}$ Analysis - Calcd. for $C_{25}H_{35}O_6N_5S.C_{10}H_6O_8N_2S$ (percent):

C, 49.58; H, 4.87; N, 11,56 Found (percent): C, 49.24; H, 4.70; N, 11.85

(C) 1-[$N^2$-(6-methoxy-2-naphthylsulfonyl)-L-arginyl]-2-piperidinecarboxylic acid A solution of 2.8 g of ethyl 1-[$N^2$-(6-methoxy-2-naphthylsulfonyl)-L-arginyl]-2-piperidinecarboxylate in 15 ml of methanol and 10 ml of 2N-NaOH solution was warmed to 60° C and held at that temperature for 10 hours. At the end of this period, the reaction mixture was concentrated and chromatographed on 200 ml of Daiaion ® SK 102 ion exchange resin (200 - 300 mesh, $H^+$ form, manufactured by Mitsubishi Chemical Industries Limited) packed in water, washed with ethanol-water (1:4) and eluted with ethanol-water-$NH_4OH$ (10:9:1). The main fraction was evaporated to dryness and washed with ethyl ether to give 2.0 g of 1-[$N^2$-(6-methoxy-2-naphthylsulfonyl)-L-arginyl]-2-piperidinecarboxylic acid as an amorphous solid. I. R. (KBr): 3,200 (broad), 1,620, 1,150 $cm^{-1}$ Analysis - Calcd. for $C_{23}H_{31}O_6N_5S$ (percent): C, 54.64; H, 6.18; N, 13.85 Found (percent): C, 56.88; H, 6.31; N, 13.83

The following compounds are prepared in a similar manner:

$N^2$-(6-chloro-2-naphthylsulfonyl)-L-arginyl-N-butylglycine
$N^2$-(7-methyl-2-naphthylsulfonyl)-L-arginyl-N-(2-ethoxyethyl)-glycine
$N^2$-(7-methoxy-2-naphthylsulfonyl)-L-arginyl-N-(2-methylthioethyl)glycine
$N^2$-(4,6-dimethoxy-2-naphthylsulfonyl)-L-arginyl-N-(2-methylthioethyl)glycine
$N^2$-(4,6-dimethoxy-2-naphthylsulfonyl)-L-arginyl-N-phenethyl-$\beta$-alanine
$N^2$-(6,7-dimethoxy-2-naphthylsulfonyl)-N-benzyl-N-(3-carboxypropyl)-L-arginiamide
$N^2$-(7-methoxy-2-naphthylsulfonyl)-L-arginyl-N-cyclohexylnorleucine
$N^2$-(7-methoxy-2-naphthylsulfonyl)-L-arginyl-N-butylisoleucine
$N^2$-(7-methoxy-2-naphthylsulfonyl)-L-arginyl-N-pentylbutyrine
$N^2$-(6,7-diethoxy-2-naphthylsulfonyl)-L-arginyl-N-butylalanine
$N^2$-(6,7-dimethoxy-2-naphthylsulfonyl)-L-arginyl-N-cycloheptylalanine
$N^2$-(7-methoxy-2-naphthylsulfonyl)-L-arginyl-N-(2-methoxyethyl)alanine
$N^2$-(6,7-dimethoxy-2-naphthylsulfonyl)-L-arginyl-N-(2-ethoxyethyl)alanine
$N^2$-(7-methoxy-2-naphthylsulfonyl)-L-arginyl-N-cyclohexyl-$\beta$-alanine
$N^2$-(7-methoxy-2-naphthylsulfonyl)-L-arginyl-N-(2-methoxyethyl)norvaline
$N^2$-(6,7-dimethoxy-2-naphthylsulfonyl)-L-arginyl-N-benzylleucine
1-[$N^2$-(5-methoxy-1-naphthylsulfonyl)-L-arginyl]-4-ethyl-2-piperidinecarboxylic acid
1-( $N^2$-(6-methoxy-2-naphthylsulfonyl)-L-arginyl]-4-ethyl-2-piperidinecarboxylic acid
1-[$N^2$-(4,6-dimethoxy-2-naphthylsulfonyl)-L-arginyl]-4-ethyl-2-piperidinecarboxylic acid
1-[$N^2$-(5-ethoxy-1-naphthylsulfonyl)-L-arginyl]-4-ethyl-2-piperidinecarboxylic acid
1-[$N^2$-(7ethoxy-2-naphthylsulfonyl)-L-arginyl]-4-ethyl-2-piperidinecarboxylic acid
1-[$N^2$-(6,7-diethoxy-2-naphthylsulfonyl)-L-arginyl]-4-ethyl-2-piperidinecarboxylic acid
1-[$N^2$-(7-methoxy-2-naphthylsulfonyls)-L-arginyl]-4-tert-butyl-2-piperidinecarboxylic acid
Phenyl 1-[$N^2$-(7-methoxy-2-naphthylsulfonyl)-L-arginyl]-4-ethyl-2-piperidinecarboxylate
Benzyl 1-[$N^2$-(7-methoxy-2-naphthylsulfonyl)-L-arginyl]-4-ethyl-2-piperidinecarboxylate
Benzyl 1-[$N^2$-(6,7-dimethoxy-2-naphthylsulfonyl)-L-arginyl]-4-methyl-2-piperidinecarboxylate
1-[$N^2$-(5-nitro-1-naphthylsulfonyl)-L-arginyl]-4-methyl-2-piperidinecarboxylic acid
1-[$N^2$-(7-hydroxy-2-naphthylsulfonyl)-L-arginyl]-4-ethyl-2-piperidinecarboxylic acid
1-[$N^2$-(5-cyano-1-naphthylsulfonyl)-L-arginyl]-4-methyl-2-piperidinecarboxylic acid
1-[$N^2$-(7-methyl-2-naphthylsulfonyl)-L-arginyl]-4-ethyl-2-piperidinecarboxylic acid
1-[$N^2$-(5-dimethylamino-1-naphthylsulfonyl)-L-arginyl]-4-ethyl-2-piperidinecarboxylic acid
1-[$N^2$-(2-naphthylsulfonyl)-L-arginyl]-4-ethyl-2-piperidinecarboxylic acid
1-[$N^2$-(5,6,7,8-tetrahydro-2-naphthylsulfonyl)-L-arginyl]-4-ethyl-2-piperidinecarboxylic acid
1-[$N^2$-(5-dimethylamino-1-naphthylsulfonyl)-L-arginyl]-4-methyl-2-piperidinecarboxylic acid
1-[$N^2$-(7-methyl-2-naphthylsulfonyl)-L-arginyl]-6-methyl-2-piperidinecarboxylic acid
1-[$N^2$-(7-methyl-2-naphthylsulfonyl)-L-arginyl]-4-tert-butyl-2-piperidinecarboxylic acid
1-[$N^2$-(5-nitro-1-naphthylsulfonyl)-L-arginyl]indoline-2-carboxylic acid
2-[$N^2$-(5-cyano-1-naphthylsulfonyl)-L-arginyl]isoindoline-1-carboxylic acid
4-[$N^2$-(7-methyl-2-naphthylsulfonyl)-L-arginyl]thiomorpholine-3-carboxylic acid
4-[$N^2$-(6,7-dimethyl-2-naphthylsulfonyl)-L-arginyl]-morpholine-3-carboxylic acid
4-[$N^2$-(5,6,7,8-tetrahydro-2-naphthylsulfonyl)-L-arginyl]-3-carboxythiomorpholine 1-oxide
4-[$N^2$-(7-methyl-2-naphthylsulfonyl)-L-arginyl]morpholine-3-carboxylic acid
4-[$N^2$-(7-chloro-2-naphthylsulfonyl)-L-arginyl]morpholine-3-carboxylic acid
4-[$N^2$-(7-hydroxy-2-naphthylsulfonyl)-L-arginyl]-morpholine-3-carboxylic acid
4-[$N^2$-(5-nitro-1-naphthylsulfonyl)-L-arginyl]thiomorpholine-3-carboxylic acid
4-[$N^2$-(5-cyano-1-naphthylsulfonyl)-L-arginyl]thiomorpholine-3-carboxylic acid
4-[$N^2$-(5-methoxy-1-naphthylsulfonyl)-L-arginyl]-morpholine-3-carboxylic acid
Ethyl 4-[$N^2$-(4,6-dimethoxy-2-naphthylsulfonyl)-L-arginyl]morpholine-3-carboxylate
4-[$N^2$-(5-ethoxy-1-naphthylsulfonyl)-L-arginyl]morpholine-3-carboxylic acid
4-[$N^2$-(5-dimethylamino-1-naphthylsulfonyl)-L-arginyl]thiomorpholine-3-carboxylic acid
3-[$N^2$-(1-naphthylsulfonyl)-L-arginyl]thiazolidine-4-carboxylic acid
2-[$N^2$-(7-methoxy-2-naphthylsulfonyl)-L-arginyl]-1,2,3,4-tetrahydroisoquinoline-1-carboxylic acid
2-[$N^2$-(7-methoxy-2-naphthylsulfonyl)-L-arginyl-]isoindoline-1-carboxylic acid
2-[$N^2$-(4,6-dimethoxy-2-naphthylsulfonyl)-L-arginyl]-1,2,3,4-tetrahydroisoquinoline-3-carboxylic acid
2-[$N^2$-(5-methoxy-1-naphthylsulfonyl)-L-arginyl-]isoindoline-1-carboxylic acid
2-[$N^2$-(5-ethoxy-1-naphthylsulfonyl)-L-arginyl]-1,2,3,4-tetrahydroisoquinoline-3-carboxylic acid

EXAMPLE 3

(A) $N^G$-nitro-$N^2$-(tert-butoxycarbonyl)-L-arginyl-N-(2-methoxyethyl)glycine ethyl ester:

To a stirred solution of 28.3 g of $N^G$-nitro-$N^2$-(tert-butoxycarbonyl)-L-arginine in 450 ml of dry tetrahydrofuran were added in turn 12.4 ml of triethylamine and 12.4 ml of isobutyl chloroformate while keeping the temperature at $-5°$ C. After 15 minutes, to this was added 14.2 g of N-(2-methoxyethyl)glycine ethyl ester, and the mixture was stirred for 15 minutes at $-5°$ C. At the end of this period, the reaction mixture was warmed to room temperature. The solvent was evaporated and the residue taken up in 400 ml of ethyl acetate, and washed successively with 200 ml of water, 100 ml of 5% sodium bicarbonate solution, 100 ml of 10% citric acid solution and 200 ml of water. The ethyl acetate solution was dried over anhydrous sodium sulfate. Upon evaporation of the solvent, the residue was dissolved in 20 ml of chloroform, and the solution was applied to a column (80 cm × 6 cm) of 500 g of silica gel packed in chloroform. The product was eluted first with chloroform, and then 3% methanol-chloroform. The fraction eluted from 3% methanol-chloroform was evaporated to dryness to give 25.8 g (63 percent) of $N^G$-nitro-$N^2$-(tert-butoxycarbonyl)-L-arginyl-N-(2-methoxyethyl)glycine ethyl ester in the form of a syrup.

I.R. (KBr): 3,300, 1,740, 1,690 $cm^{-1}$ (B) $N^G$-nitro-L-arginyl-N-(2-methoxyethyl)glycine ethyl ester hydrochloride:

To a stirred solution of 29.8 g of $N^G$-nitro-$N^2$-(tert-butoxycarbonyl)-L-arginyl-N-(2-methoxyethyl)glycine ethyl ester in 50 ml of ethyl acetate was added 80 ml of 10% dry HCl-ethyl acetate at 0° C. After 3 hours, to this solution was added 200 ml of dry ethyl ether to precipitate a viscous oily product.

This was filled and washed with dry ethyl ether to give 24.1 g of $N^G$-nitro-L-arginyl-N-(2-methoxyethyl) glycine ethyl ester hydrochloride as an amorphous solid.

(C) $N^G$-nitro-$N^2$-(6,7-dimethoxy-2-naphthylsulfonyl)-L-arginyl-N-(2-methoxyethyl)glycine ethyl ester:

To a stirred solution of 4.0 g of $N^G$-nitro-L-arginyl-N-(2-methoxyethyl)glycine ethyl ester hydrochloride in 20 ml of water and 20 ml of dioxane were added in turn 2.5 g of sodium bicarbonate, and 3.5 g of 6,7-dimethoxy-2-naphthalenesulfonyl chloride in 30 ml of dioxane at 5° C, and stirring was continued for 3 hours at room temperature. At the end of this period, the solvent was evaporated and the residue dissolved in 40 ml of chloroform, and washed with 10 ml of 1N hydrochloric acid solution and 20 ml of water.

The chloroform solution was dried over anhydrous sodium sulfate. Upon evaporation of the solvent, the residue was chromatographed on 50 g of silica gel packed in chloroform, washed with chloroform and eluted with 3% methanol-chloroform. The fraction eluted from 3% methanol-chloroform was evaporated to give 5.3 g (87 percent) of $N^G$-nitro-$N^2$-(6,7-dimethoxy-2-naphthylsulfonyl)-L-arginyl-N-(2-methoxyethyl)glycine ethyl ester in the form of an amorphous solid.

I.R. (KBr): 3,240, 1,740, 1,630 $cm^{-1}$ (D) $N^2$-(6,7-dimethoxy-2-naphthylsulfonyl)-L-arginyl-N-(2-methoxyethyl)glycine ethyl ester:

To a solution of 3.00 g of $N^G$-nitro-$N^2$-(6,7-dimethoxy-2-naphthylsulfonyl)-L-arginyl-N-(2-methoxyethyl)glycine ethyl ester in 50 ml of ethanol and 0.5 ml of acetic acid was added 0.5 g of palladium-black and then the mixture was shaken in a hydrogen atmosphere for 100 hours at room temperature. At the end of this period, the ethanol solution was filtered to remove the catalyst and evaporated to give an oily product. Reprecipitation with ethanol-ethyl ether gave 2.53 g (91%) of $N^2$-(6,7-dimethoxy-2-naphthylsulfonyl)-L-arginyl-N-(2-methoxyethyl)glycine ethyl ester.

For analysis of the product, a portion of the product was converted to the flavianate; M.P. 185° C, I.R. (KBr): 3,375, 3,200, 1,740 $cm^{-1}$.

Analysis - Calcd. for $C_{25}H_{37}N_5O_8S.C_{10}H_6N_2O_8S$ (percent): C, 47.67; H, 4.92; N, 11.12 Found (percent): C, 47.64; H, 4.81; N, 11.12

(E) $N^2$-(6,7-dimethoxy-2-naphthylsulfonyl)-L-arginyl-N-(2-methoxyethyl)glycine:

A solution of 2.5 g of $N^2$-(6,7-dimethoxy-2-naphthylsulfonyl)-L-arginyl-N-(2-methoxyethyl)glycine ethyl ester in 5 ml of ethanol and 7 ml of 1N sodium hydroxide solution was stirred for 30 hours at room temperature. At the end of this period, the solution was concentrated to 5 ml, chromatographed on 80 ml of Daiaion ® SK 102 ion exchange resin (200 - 300 mesh, $H^+$ form manufactured by Mitsubishi Chemical Industries Limited) packed in water, washed with water, and eluted with 3% ammonium hydroxide solution. The fraction eluted from 3% ammonium hydroxide solution was evaporated to dryness, and the residue was purified by reprecipitation with ethanol-ethyl ether to give 1.32 g (72 percent) of $N^2$-(6,7-dimethoxy-2-naphthylsulfonyl)-L-arginyl-N-(2-methoxyethyl)glycine as an amorphous solid. I.R. (KBr): 3,380, 3,180, 1,630 $cm^{-1}$ Analysis - Calcd. for $C_{23}H_{33}N_5O_8S$ (percent): C, 51.20; H, 6.17; N, 12.98 Found (percent): C, 50.93; H, 6.02; N, 12.63

The following compounds are prepared in a similar manner:

$N^2$-(5,6,7,8-tetrahydro-2-naphthylsulfonyl)-L-arginyl-N-(2-ethoxyethyl)glycine $N^2$-(5,6,7,8-tetrahydro-2-naphthylsulfonyl)-L-arginyl-N-(2-methoxyethyl)glycine $N^2$-(7-ethyl-2-naphthylsulfonyl)-L-arginyl-N-(2-methoxyethyl)glycine $N^2$-(5-methoxy-1-naphthylsulfonyl)-L-arginyl-N-cyclohexylglycine $N^2$-(7-methoxy-2-naphthylsulfonyl)-L-arginyl-N-(3-cyclohexyl)propylglycine 2-[$N^2$-(7-methyl-2-naphthylsulfonyl)-L-arginyl]-1,2,3,4-tetrahydroisoquinoline-3-carboxylic acid 2[$N^2$-(7-methyl-2-naphthylsulfonyl)-L-arginyl]isoindoline-1-carboxylic acid 2-[$N^2$-(6,7-dimethyl-2-naphthylsulfonyl)-L-arginyl-]isoindoline-1-carboxylic acid 2-[$N^2$-(2-naphthylsulfonyl)-L-arginyl]isoindoline-1-carboxylic acid 2-[$N^2$-(5,6,7,8-tetrahydro-2-naphthylsulfonyl)-L-arginyl]-1,2,3,4-tetrahydroisoquinoline-3-carboxylic acid 2-[$N^2$-(5,6,7,8-tetrahydro-1-naphthylsulfonyl)-L-arginyl]isoindoline-1-carboxylic acid 2-[$N^2$-(5-chloro-1-naphthylsulfonyl)-L-arginyl]-1,2,3,4-tetrahydroisoquincline-3-carboxylic acid 1-[$N^2$-(5-hydroxy-1-naphthylsulfonyl)-L-arginyl]-1,2,3,4-tetrahydroquinoline-2-carboxylic acid 2-[$N^2$-(5-dimethylamino-1-naphthylsulfonyl)-L-arginyl]isoindoline-1-carboxylic acid 2-[$N^2$-(1-naphthylsulfonyl)-L-arginyl]-1,2,3,4-tetrahydroisoquinoline-3-carboxylic acid

EXAMPLE 4

(A) L-arginyl-N-(2-methoxyethyl)glycine ethyl ester hydrochloride:

To a solution of 4.0 g of $N^G$-nitro-L-arginyl-N-(2-methoxyethyl)glycine ethyl ester hydrochloride in 50 ml of ethanol was added 0.5 g of palladium-black and then the mixture was shaken in a hydrogen atmosphere for 150 hours at room temperature. At the end of this period, the ethanol solution was filtered to remove the catalyst and evaporated to give an oily product. Reprecipitation with ethanol-ethyl ether gave 3.0 g (81%) of L-arginyl-N-(2-methoxyethyl)glycine ethyl ester hydrochloride in the form of a powder.

(B) $N^2$-(4,6-dimethoxy-2-naphthylsulfonyl)-L-arginyl-N-(2-methoxyethyl)glycine ethyl ester:

To a well stirred solution of 2.00 g of L-arginyl-N-(2-methoxyethyl)glycine ethyl hydrochloride and 1.95 g of $K_2CO_3$ in 20 ml of water and 10 ml of dioxane was added dropwise a solution of 2.17 g of 4,6-dimethoxy-2-naphthalenesulfonyl chloride in 30 ml of dioxane over a period of 30 minutes while maintaining the temperature at 0° C. The reaction mixture was stirred for an additional 5 hours at room temperature. At the end of this period, the solvent was evaporated and the residue taken up in 50 ml of chloroform. The chloroform solution was filtered to remove the insoluble material and dried over anhydrous sodium sulfate. Addition of 150 ml of ethyl ether to the chloroform solution resulted in a precipitate which was separated by decantation and purified by reprecipitation with ethanol-ethyl ether to give 2.31 g (72 percent) of $N^2$-(4,6-dimethoxy-2-naphthylsulfonyl)-L-arginyl-N-(2-methoxyethyl)glycine ethyl ester. For analysis of the product, a portion of the product was converted to the flavianate; M.P. 225°-227° C, I.R. (KBr): 3,375, 3,200, 1,742 $cm^{-1}$.

Analysis - Calcd. for $C_{25}H_{37}N_5O_8S.C_{10}H_6N_2O_8S$ (percent): C, 47.67; H, 4.92; N, 11.12 Found (percent): C, 47.62; H, 4.84; N, 11.18

(B) $N^2$-(4,6-dimethoxy-2-naphthylsulfonyl)-L-arginyl-N-(2-methoxyethyl)glycine:

$N^2$-(4,6-dimethoxy-2-naphthylsulfonyl)-L-arginyl-N-(2-methoxyethyl)glycine was obtained in the form of an amorphous solid in a manner similar to that described in Example 3 (E).

I.R. (KBr): 3,360, 3,180, 1,610 $cm^{-1}$.

EXAMPLE 5

(A) $N^2$-(6,7-dimethoxy-2-naphthylsulfonyl)-L-arginyl-N-phenethylglycine:

$N^G$-nitro-$N^2$-(6,7-dimethoxy-2-naphthylsulfonyl)-L-arginyl-N-phenethylglycine benzyl ester was prepared by the procedure described in Example 3, and has a melting point of 133°-5° C. To a solution of 3.00 g of $N^G$-nitro-$N^2$-(6,7-dimethoxy-2-naphthylsulfonyl)-L-arginyl-N-phenethylglycine benzyl ester in 50 ml of ethanol and 0.5 ml of acetic acid was added 0.5 of palladium-black and then the mixture was shaken in a hydrogen atmosphere for 100 hours at room temperature. At the end of this period, the ethanol solution was filtered to remove the catalyst and evaporated to dryness. The residue was washed several times with dry ethyl ether and chromatographed on 80 ml of Daiaion ® SK 102 ion exchange resin (200 - 300 mesh, II+ form, manufactured by Mitsubishi Chemical Industries Limited) packed in water, washed with water, and eluted with 3% ammonium hydroxide solution. The fraction eluted from 3% ammonium hydroxide solution was evaporated to dryness to give 1.71 g (70%) of $N^2$-(6,7-dimethoxy-2-naphthylsulfonyl)-L-arginyl-N-phenethylglycine as an amorphous solid.

I.R. (KBr): 3,360, 3,200, 1,590 $cm^{-1}$ Analysis - Calcd. for $C_{28}H_{35}N_5O_7S$ (percent): C, 57.42; H, 6.02; N, 11.97 Found (percent): C, 57.09; H, 6.06; N, 11.74

EXAMPLE 6

(A) $N^2$-(6,7-dimethoxy-2-naphthylsulfonyl)-L-arginyl-N-(2-methoxyethyl)glycyl chloride hydrochloride:

A suspension of 2.00 g of $N^2$-(6,7-dimethoxy-2-naphthylsulfonyl)-L-arginyl-N-(2-methoxyethyl)glycine in 20 ml of thionyl chloride was stirred for 2 hours at room temperature. Addition of cold dry ethyl ether resulted in a precipitate which was collected by filtration and washed several times with dry ethyl ether to give $N^2$-(6,7-dimethoxy-2-naphthylsulfonyl)-L-arginyl-N-(2-methoxyethyl)glycyl chloride hydrochloride.

(B) $N^2$-(6,7-dimethoxy-2-naphthylsulfonyl)-L-arginyl-N-(2-methoxyethyl)glycine m-tolyl ester hydrochloride:

A mixture of 2.00 g of m-cresol and $N^2$-(6,7-dimethoxy-2-naphthylsulfonyl)-L-arginyl-N-(2-methoxyethyl)glycyl chloride hydrochloride obtained above was heated at 90° C for 50 minutes. At the end of this period, the reaction mixture was cooled, washed several times with dry ethyl ether, and then dissolved in 10 ml of dry ethyl alcohol. Addition of cold dry ethyl ether resulted in a precipitate which was washed several times with dry ethyl ether to give 2.12 g (86 percent) of $N^2$-(6,7-dimethoxy-2-naphthylsulfonyl)-L-arginyl-N-(2-methoxyethyl)glycine m-tolyl ester hydrochloride in the form of a powder.

I.R. (KBr): 3,250, 3,100, 1,740, 1,640 $cm^{-1}$.

The following compounds are prepared in a similar manner:

$N^2$-(6,7-dimethoxy-2-naphthylsulfonyl)-L-arginyl-N-(2-ethylthioethyl)glycine phenyl ester $N^2$-(6,7-dimethoxy-2-naphthylsulfonyl)-L-arginyl-N-(2-ethylthicethyl)glycine benzyl ester $N^2$-(6,7-dimethoxy-2-naphthylsulfonyl)-L-arginyl-N-benzylglycine phenyl ester $N^2$-(6,7-dimethoxy-2-naphthylsulfonyl)-L-arginyl-N-furfurylglycine benzyl ester $N^2$-(6,7-dimethoxy-2-naphthylsulfonyl)-L-arginyl-N-tetrahydrofurfurylglycine phenyl ester Phenyl 1-[$N^2$-(7-methyl-2-naphthylsulfonyl)-L-arginyl]-4-ethyl-2-piperidinecarboxylate Benzyl 1-[$N^2$-(7-methyl-2-naphthylsulfonyl)-L-arginyl]-4-ethyl-2-piperidinecarboxylate Benzyl 1-[$N^2$-(6-chloro-2-naphthylsulfonyl)-L-arginyl]-4-methyl-2-piperidinecarboxylate Ethyl 4-[$N^2$-(7-methyl-2-naphthylsulfonyl)-L-arginyl]morpholine-3-carboxylate Various other $N^2$-arylsulfonyl-L-argininamides or salts thereof were synthesized in accordance with the procedure of the above examples, and the test results are summarized in Table 2.

EXAMPLE 7

Tablets suitable for oral administration

Tablets containing the ingredients indicated below may be prepared by conventional techniques.

| Ingredient | Amount per tablet (mg) |
|---|---|
| $N^2$-(7-methoxy-2-naphthylsulfonyl)-L-arginyl-N-(2-methoxyethyl)glycine | 250 |
| Lactose | 140 |
| Corn starch | 35 |
| Talcum | 20 |

-continued

| Ingredient | Amount per tablet (mg) |
|---|---|
| Magnesium stearate | 5 |
| Total | 450 mg |

EXAMPLE 8

Capsules for oral administration

Capsules of the below were made up by thoroughly mixing together batches of the ingredients and filling hard gelatin capsules with the mixture.

| Ingredient | Amount per capsule (mg) |
|---|---|
| $N^2$-(7-methoxy-2-naphthylsulfonyl)-L-arginyl-N-(2-methoxyethyl)glycine | 250 |
| Lactose | 250 |
| Total | 500 mg |

EXAMPLE 9

Sterile solution for infusion

The following ingredients are dissolved in water for intravenous perfusion and the resulting solution is then sterilized.

| Ingredients | Amount (g) |
|---|---|
| $N^2$-(7-methoxy-2-naphthylsulfonyl)-L-arginyl-N-(2-methoxyethyl)glycine | 25 |
| Buffer system | As desired |
| Glucose | 25 |
| Distilled water | 500 |

APPENDIX

There are now described in greater detail preparation of materials of the kind used in the foregoing examples.

PREPARATION A

Arylsulfonyl Chlorides (A) Sodium 6,7-dimethoxy-2-naphthalenesulfonate

To a well stirred solution of 70.8 g of sodium 6,7-dihydroxy-2-naphthalenesulfonate and 77.2 g of sodium hydroxide in 450 ml of water was added dropwise 230 ml of dimethyl sulfate at 60° C over a period of 1 hour, during which time the product precipitated. To this reaction mixture was added in portions 38.8 g of sodium hydroxide, and stirring was continued for one hour. After one hour at room temperature, the precipitate was filtered, washed with ethanol and dried to give 50 g of sodium 6,7-dimethoxy-2-naphthalenesulfonate.

(B) 6,7-dimethoxy-2-naphthalenesulfonyl chloride

To a stirred suspension of 50 g of finely divided sodium 6,7-dimethoxy-2-naphthalenesulfonate in 100 ml of dimethylformamide was added dropwise 62.2 ml of thionyl chloride at room temperature. After 30 minutes, the reaction mixture was poured into 1 l of ice water, and the precipitate filtered and then dissolved into 250 ml of benzene. The benzene solution was repeatedly washed with water and dried over anhydrous sodium sulfate. The solvent was evaporated to dryness in vacuo, and the residue was recrystallized from benzene-n-hexane (1 : 1) to give 32 g of 6,7-dimethoxy-2-naphthalenesulfonyl chloride, M.P. 127.5° - 129.5° C Analysis - Calcd. for $C_{12}H_{11}O_4SCl$ (percent): C, 50.26; H, 3.87; Cl, 12.37 Found (percent): C, 50.45; H, 4.00; Cl, 12.33

The following arylsulfonyl chlorides not previously reported in the chemical literature were synthesized by the aforementioned procedure which is essentially that as described in E. H. Rodd, "Chemistry of Carbon Compounds", Elsevier Publishing Company, 1954, Vol III, P. 441–469.

| No. | Arylsulfonyl Chloride | M.P. (° C) |
|---|---|---|
| 1 | 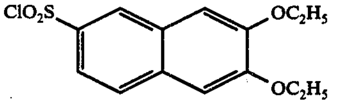 | 118–119.5 |
| 2 | 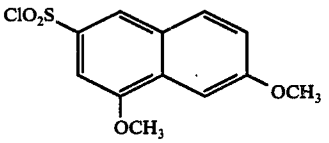 | 136.5–138.5 |
| 3 | 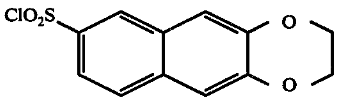 | 137–139 |

PREPARATION B (A) N-butylglycine tert-butyl ester

To 36.5 g of butylamine was added with stirring 15.05 g of tert-butyl chloroacetate over a period of 30 minutes, while maintaining the temperature at 30°–70° C. The reaction mixture was held at 70° C for an additional one hour. At the end of this period, the excess butyl amine was evaporated in vacuo, and the residue was taken up in 40 ml of 2N NaOH solution and 50 ml of benzene, transferred into a separatory funnel and well shaken. The benzene solution was separated, washed with water, dried over anhydrous sodium sulfate and filtered. After evaporation of benzene, the residue was distilled under reduced pressure to give 17.0 g (90.9 percent) of N-butylglycine tert-butyl ester, B.P. 76° C/4 mmHg.

The following amino acid tert-butyl esters not previously reported in the chamical literature were synthesized by the aforementioned procedure which is essentially that as taught by A. J. Speziale et al., J. Org. Chem. 25 731 (1960).

| No. | Amino Acid Derivative | B.P. |
|---|---|---|
| 1 | 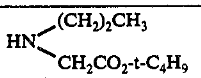 | 95° C/20 mmHg |
| 2 | 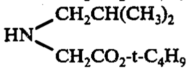 | 65° C/5 mmHg |
| 3 | 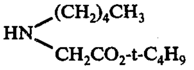 | 89–90° C/2.5 mmHg |
| 4 | 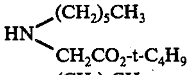 | 83–5° C/1.5 mmHg |
| 5 | 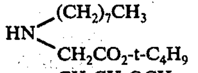 | 125–130° C/4 mmHg |
| 6 | 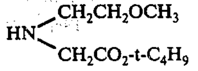 | 61–2° C/2 mmHg |

-continued

| No. | Amino Acid Derivative | B.P. |
|---|---|---|
| 7 | 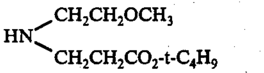 | 94° C/3 mmHg |
| 8 | 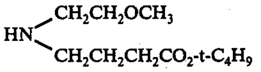 | 60-3° C/3 mmHg |
| 9 | 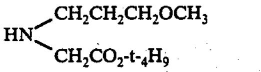 | 95-7° C/5 mmHg |
| 10 | 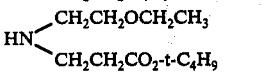 | 102° C/4 mmHg |
| 11 | 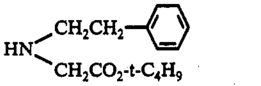 | 166° C/10 mmHg |
| 12 | 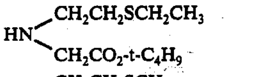 | 106-9° C/1.5 mmHg |
| 13 | 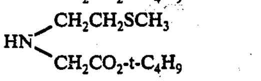 | 97° C/2.5 mmHg |
| 14 | 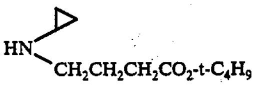 | 101° C/5 mmHg |
| 15 | 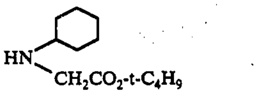 | 101° C/5 mmHg |
| 16 | 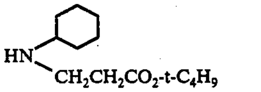 | 105° C/4 mmHg |
| 17 | 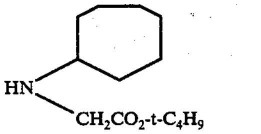 | 129-130° C/8 mmHg |
| 18 | 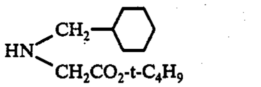 | 145° C/15 mmHg |
| 19 | 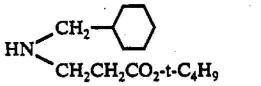 | 156° C/10 mmHg |
| 20 | 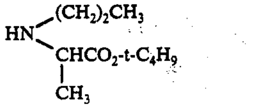 | 93° C/26 mmHg |
| 21 | 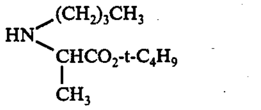 | 110° C/27 mmHg |
| 22 | 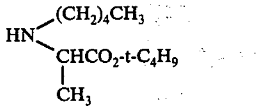 | 124° C/26 mmHg |
| 23 | 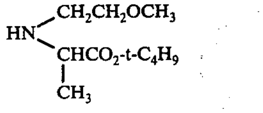 | 88-90° C/6 mmHg |
| 24 | 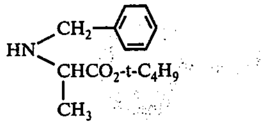 | 116-8° C/2 mmHg |

-continued

| No. | Amino Acid Derivative | B.P. |
|---|---|---|
| 25 | 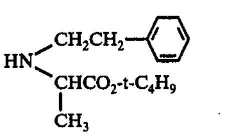 | 167° C/16 mmHg |
| 26 | 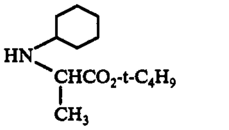 | 125° C/16 mmHg |
| 27 | 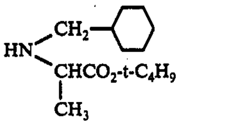 | 141° C/15 mmHg |
| 28 | 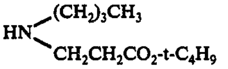 | 89° C/3 mmHg |
| 29 | 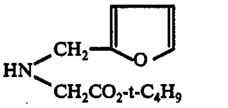 | 111° C/1 mmHg |
| 30 | 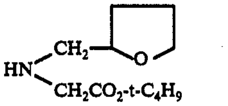 | 91-2° C/1 mmHg |
| 31 | 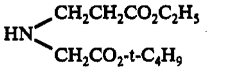 | 115° C/2 mmHg |
| 32 | 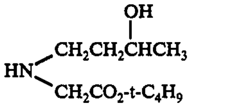 | 82-84° C/2 mmHg |
| 33 | 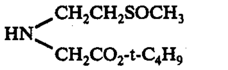 | 150° C/0.5 mmHg |
| 34 | 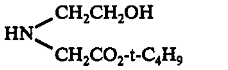 | 95-6° C/2 mmHg |
| 35 | 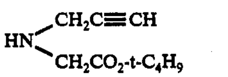 | |

(B) N-(2-methoxyethyl)glycine ethyl ester

To a stirred solution of 165.2 g of 2-methoxyethylamine and 202.4 g of triethylamine in 1 *l* of benzene was added dropwise a solution of 334.0 g of ethyl bromoacetate in 200 ml of benzene in one hour at room temperature. At the end of this period, the mixture was heated at reflux for 2 hours to complete the reaction. Upon chilling, the triethylamine hydrobromide was removed by filtration and washed with benzene. After removal of the solvent, the product was distilled in vacuo to yield 242.8 g (75.3 percent) of N-(2-methoxyethyl)glycine ethyl ester, B.P. 73°-5° C/4 mmHg.

The following amino acid ethyl esters not previously reported in the chemical literature were synthesized by the aforementioned procedure which is essentially that as taught by A. J. Speziale et al., J. Org. Chem., 25 731 (1960).

| No. | Amino Acid Ethyl Ester | M.P. (° C) or B.P. (° C/mmHg) |
|---|---|---|
| 1 | 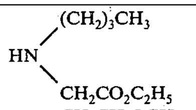 | 57-8° C/3 mmHg |
| 2 | 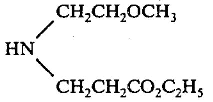 | 63-4° C/3 mmHg |

| No. | Amino Acid Ethyl Ester | M.P. (° C) or B.P. (° C/mmHg) |
|---|---|---|
| 3 | 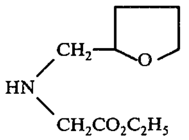 | 91-3° C/2 mmHg |
| 4 | 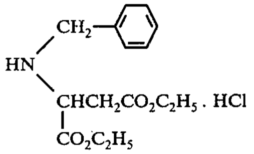 | 101-2° C |
| 5 | 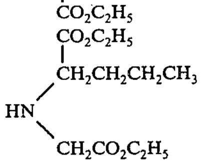 | 113-6° C/3 mmHg |
| 6 | 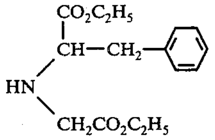 | 116-7° C/1 mmHg |
| 7 | 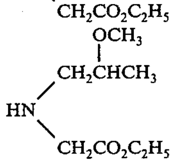 | 78-80° C/2 mmHg |
| 8 | 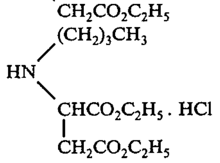 | 63-4° C |

(C) N-(2-methoxyethyl)glycine benzyl ester p-toluenesulfonate

To a solution of 55.8 g of N-(2-methoxyethyl)glycine tert-butyl ester in 200 ml of benzene was added 63.8 g of benzyl alcohol and 72.9 g of p-toluenesulfonic acid monohydrate. The mixture was heated at reflux for 10 hours with the continuous removal of water through a Dean-Stark water trap. At the end of this period, the solution was concentrated in vacuo, and to the residue was added 300 ml of dry ethyl ether. After 2 hours at room temperature, the formed precipitate was filtered, washed with dry ethyl ether and then recrystallized from ethyl acetate to yield 99.2 g (85 percent) of N-(2-methoxyethyl)glycine benzyl ester p-toluenesulfonate, M.P. 95°-6° C.

The following amino acid benzyl ester p-toluenesulfonate not previously reported in the chemical literature were synthesized by the aforementioned procedure.

| No. | Amino Acid Benzyl Ester p-Toluenesulfonate | M.P. (° C) |
|---|---|---|
| 1 | 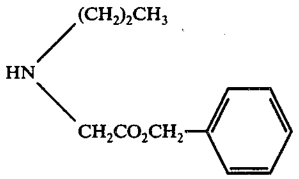 | 97 - 9 |
| 2 | 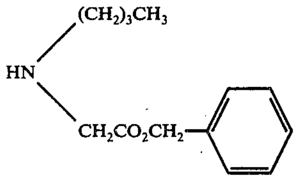 | 122 - 4 |
| 3 | 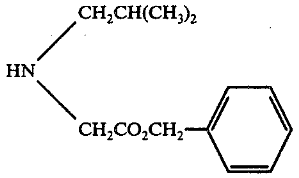 | 94 - 5 |
| 4 | 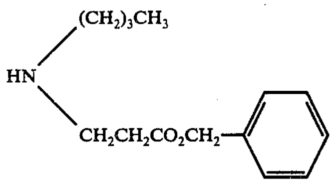 | 66 - 8 |

| No. | Amino Acid Benzyl Ester p-Toluenesulfonate | M.P. (° C) |
|---|---|---|
| 5 | 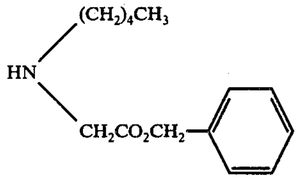 | 101-2 |
| 6 | 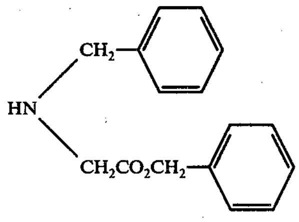 | 140-3 |
| 7 | 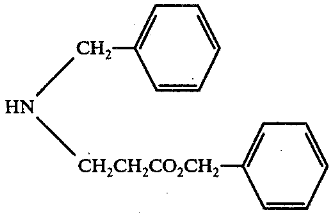 | 154-6 |

-continued

| No. | Amino Acid Benzyl Ester p-Toluenesulfonate | M.P. (° C) |
|---|---|---|
| 8 | 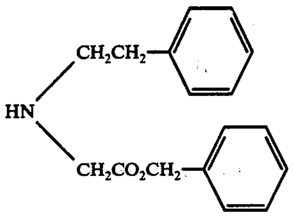 | 133-5 |
| 9 | 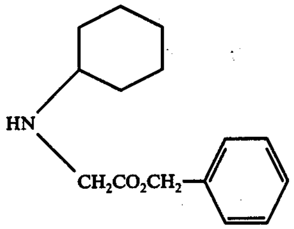 | 133-5 |
| 10 | 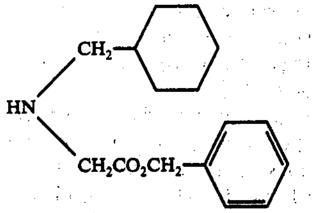 | 133-8 |
| 11 | 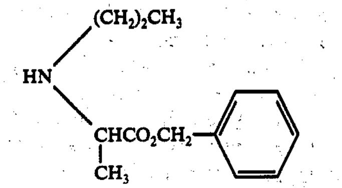 | 103-6 |
| 12 | 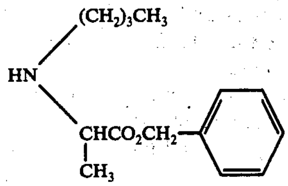 | 92-4 |

| No. | Amino Acid Benzyl Ester p-Toluenesulfonate | M.P. (° C) |
|---|---|---|
| 13 | 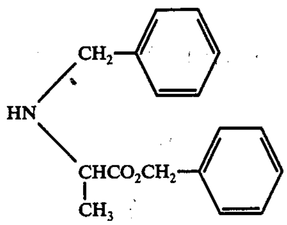 | 123-6 |
| 14 | 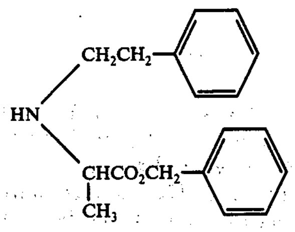 | 119-123 |

-continued

| No. | Amino Acid Benzyl Ester p-Toluenesulfonate | M.P. (° C) |
|---|---|---|
| 15 | 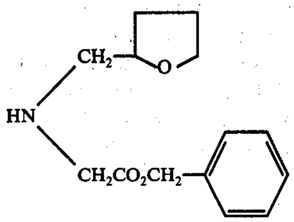 | 130-1 |

PREPARATION C

2-Piperidinecarboxylic acids and esters thereof (A) 4-methyl-2-piperidinecarbonitrile To 500 g of 10% sodium hypochlorite solution cooled in an ice bath, there was added dropwise a solution of 33.6 g (0.21 mole) of 4-methylpiperidine acetate in 10 ml of water over a period of 1 hour. At the end of this period, the reaction product was extracted twice with 500 ml of ethyl ether and dried over anhydrous sodium sulfate. After evaporation of ethyl ether, the residue was added dropwise to a solution of 11.8 g (0.21 mole) of potassium hydroxide in 100 mls of 96% ethanol under reflux Refluxing was continued for an additional 10 minutes. Ethanol was evaporated, and the residue was dissolved into 50 ml of 2N sodium hydroxide solution and then extracted with ether.

The ether layer was dried over anhydrous sodium sulfate and then ether evaporated. The residue was added to an ice-cooled solution of 27 g (1 mole) of hydrogen cyanide and 25 ml of concentrated hydrochloric acid in 300 ml of water. The solution was stirred at a temperature of 10 to 20° C for 4 hours and thereafter made basic by the addition of solid sodium hydroxide. The reaction product was extracted with ether, dried over anhydrous sodium sulfate and then distilled under reduced pressure to give 17 g (66%) of 4-methyl-2piperidinecarbonitrile, B.P. 96°-97° C/10 mmHg.

The following 2-piperidinecarbonitriles not previously reported in the chemical literature were synthesized by the aforementioned procedure which is essentially that as taught by Grundon et al., J. Chem. Soc., 1963, 3898, Grundon et al., J. Chem. Soc., 1964, 2448, R. Bonnett et al., J. Chem. Soc., 1959, 2092 and II. Bohme et al., Ber., 92 1613 (1959).

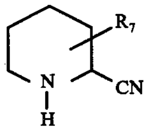

| No. | $R_7$ | B.P. |
|---|---|---|
| 1 | $4-CH_2CH_3$ | 105-106° C/9 mmHg. |
| 2 | $4-CH_2CH_2CH_3$ | 116° C/8 mmHg. |
| 3 | 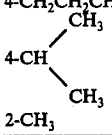 | 104° C/4 mmHg. |
| 4 | $2-CH_3$ | |

(B) 4-Methyl-2-piperidinecarboxylic acid hydrochloride

A solution of 16 g of 4-methyl-2-piperidinecarbonitrile in 250 ml of 6N hydrochloric acid was refluxed for 6 hours. After evaporation of the solvent, the residue was recrystallized from water to give 13 g of 4-methyl-2-piperidinecarboxylic acid hydrochloride.

(C) Ethyl 4-methyl-2-piperidinecarboxylate

A solution of 13 g (0.072 mole) of 4-methyl-2-piperidinecarboxylic acid hydrochloride and 50 ml of thionyl chloride in 300 ml of ethanol was refluxed for 4 hours. At the end of this period, the solvent was evaporated under reduced pressure, and the residue was extrated with a solution of chloroform and saturated potassium carbonate solution.

The chloroform layer was dried over anhydrous sodium sulfate and then chloroform was evaporated. Distillation of the residue gave 7.4 g (60%) of ethyl 4-methyl-2-piperidinecarboxylate, B.P. 76°-77° C/3 mmHg.

(D) Benzyl 4-methyl-2-piperidinecarboxylate p-toluenesulfonate

A solution of 20 g (0.112 mole) of 4-methyl-2-piperidinecarboxylic acid hydrochloride, 24 g (0.224 mole) of benzyl alcohol and 25.6 g (0.134 mole) of p-toluenesulfonic acid monohydrate in 100 ml of benzene was refluxed for 5 hours with the continuous removal of water through a Dean-Stark water trap. At the end of this period, the solvent was distilled off, and the residue was washed with ether-n-hexane and recrystallized to give 10 g (22%) of benzyl 4-methyl-2-piperidinecarboxylate p-toluenesulfonate, M.P. 160°-163° C.

The following 2-piperidinecarboxylates not previously reported in the chemical literature were synthesized by the aforementioned procedure.

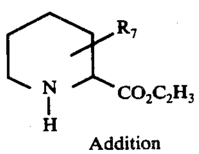

| No. | $R_7$ | Addition moiety | B.P. |
|---|---|---|---|
| 1 | $4-CH_2CH_3$ | — | 82-4° C/3.5 mmHg |
| 2 | $4-CH_2CH_2CH_3$ | HCl | |
| 3 | $4-CH(CH_3)_2$ | — | 95-6° C/2 mmHg |
| 4 | $2-CH_3$ | — | 57° C/3 mmHg |

Morpholine-3-carboxylic acid hydrochloride was prepared by the procedure described above, and has a melting point of 200°-2° C.

The following starting materials for the preparation of the $N^2$-arylsulfonyl-L-argininamides were prepared by the procedures described in the following literatures:

| Compound | Literature |
|---|---|
| 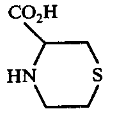 | J. Org. Chem., 29 2203 (1964) |
| 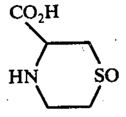 | J. Org. Chem., 29 2203 (1964) |
| 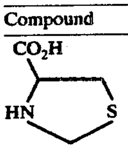 | J. Am. Chem. Soc., 59 200 (1937) |
| 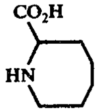 | Zh. Obshch. Khim., 9 2245 (1973) |
| 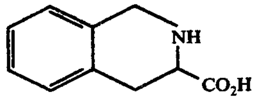 | Ber., 44 2034 (1911) |
| 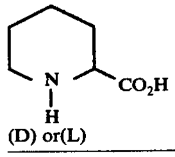 (D) or(L) | Ber., 65 927 (1932) |

The methyl or ethyl ester of the aforementioned compounds were prepared by the conventional esterification procedure. Ethyl thiomorpholine-3-carboxylate has a boiling point of 108° C/4 mmHg.

Diethyl piperidine-2,6-dicarboxylate hydrochloride was prepared by the conventional esterification of piperidine-2,6-dicarboxylic acid and has a melting point of 184°-6° C. Isoindoline-1-carboxylic acid was prepared by a procedure similar to that for the preparation of isoquinoline-3-carboxylic acid described in Ber., 44 2034 (1911). Ethyl isoindoline-1-carboxylate hydrochloride was prepared by the conventional esterification of isoindoline-1-carboxylic acid and has a melting point of 139°-140.5° C. Having now fully described the invention, it will be apparent to one of ordinary skill in the art that many changes and modifications can be made thereto without departing from the spirit of the invention as set forth herein.

What is claimed as new and desired to be secured by letters patent of the United States is:

1. An $N^2$-arylsulfonyl-L-argininamide having the formula

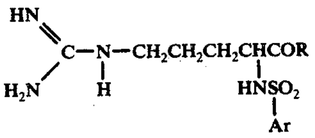

or a pharmaceutically acceptable salt thereof, wherein R is

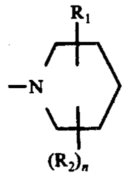

wherein $R_1$ is $—COOR_3$ wherein $R_3$ is hydrogen, $C_1$-$C_{10}$ alkyl, $C_6$-$C_{10}$ aryl, $C_7$-$C_{12}$ aralkyl or 5-indanyl; each $R_2$ independently is hydrogen, $C_1$-$C_{10}$ alkyl, phenyl, $C_1$-$C_5$ alkoxy, $C_2$-$C_6$ alkoxycarbonyl, or carboxy; n is an integer of 1 to 4, $R_1$ is substituted into the piperidine ring at the 2 or 3 position; and $R_2$ is substituted into the piperidine ring at the 2, 3, 4, 5 or 6 position;

and Ar is 1, 2, 3, 4-tetrahydroquinolyl or 1, 2, 3, 4-tetrahydroisoquinolyl, either of which may be substituted with one or more groups selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$-$C_{12}$ aralkyl, carboxy, $C_2$-$C_{10}$ alkoxycarbomyl, $C_2$-$C_{10}$carboxyalkyl, $C_1$-$C_{10}$acylamino, $C_2$-$C_{10}$ alkylcarbomyl, $C_1$-$C_{10}$ hydroxyalkyl, $C_1$-$C_{10}$ haloalkyl, oxo and phenyl optionally substituted with at least one hydroxy, $C_1$-$C_5$alkoxy from the group consisting of halo, nitro, cyano, hydroxy, $C_1$-$C_{10}$ alkyl, $C_1$-$C_{10}$ alkoxy, $C_2$-$C_{20}$ dialkylamino, sulfoamino, carbamoyl, $C_3$-$C_{10}$ N,N-dialkyl-carbamoyl, amino, $C_1$-$C_{10}$alkylamino, mercapto, $C_1$-$C_{10}$ alkylthio, $C_7$-$C_{12}$ aralkyl, carboxyl, $C_2$-$C_{10}$ alkoxycarbonyl, $C_2$-$C_{10}$ carboxyalkyl, $C_1$-$C_{10}$ acylamino, $C_2$-$C_{10}$ alkylcarbonyl, $C_1$-$C_{10}$ hydroxyalkyl, $C_1$-$C_{10}$ haloalkyl and phenyl optionally substituted with at least one hydroxy, $C_1$-$C_5$ alkoxy or mixtures thereof.

2. The compound of claim 1, wherein said Ar group is substituted with at least one $C_1$-$C_5$ alkoxy, $C_1$-$C_5$ alkyl group or mixtures thereof.

3. The compound of claim 1 wherein Ar is selected from the group consisting of

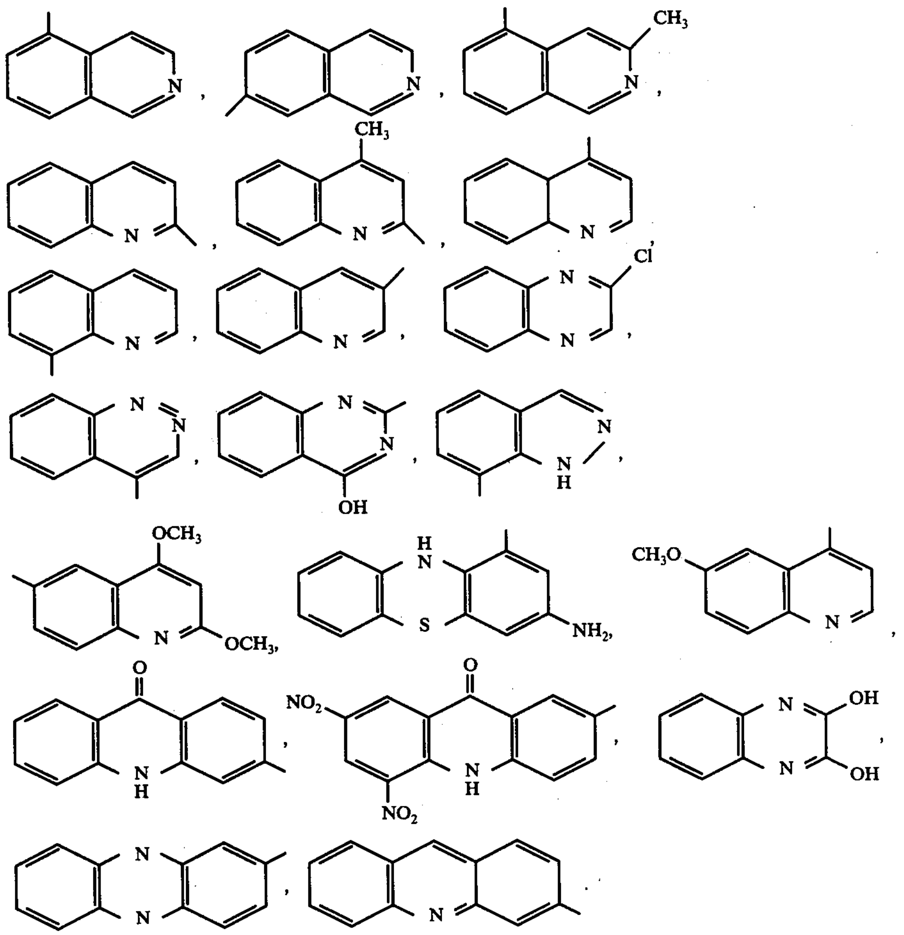

or mixtures thereof;

quinolyl, isoquinolyl, phthalozinyl, quinoxalinyl, quinazolinyl, cinnolinyl, acridinyl, phenazinyl, phenothiazinyl or phenoxazinyl, any of which may be substituted with one or more groups selected 4. A method of inhibiting activity and suppressing activation of thrombin in vivo which comprises administering to a mammal a pharmaceutically effective amount of a compound of claim 1.

* * * * *